US008980295B2

(12) United States Patent
Kao et al.

(10) Patent No.: US 8,980,295 B2
(45) Date of Patent: Mar. 17, 2015

(54) MULTIFUNCTIONAL IN SITU POLYMERIZED NETWORK VIA THIOL-ENE AND THIOL-MALEIMIDE CHEMISTRY

(75) Inventors: Weiyuan J. Kao, Middleton, WI (US); Yao Fu, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 95 days.

(21) Appl. No.: 13/411,387

(22) Filed: Mar. 2, 2012

(65) Prior Publication Data

US 2012/0225101 A1 Sep. 6, 2012

Related U.S. Application Data

(60) Provisional application No. 61/448,543, filed on Mar. 2, 2011.

(51) Int. Cl.
| | |
|---|---|
| *A61K 31/7088* | (2006.01) |
| *A61K 35/00* | (2006.01) |
| *A61K 38/22* | (2006.01) |
| *A61K 38/43* | (2006.01) |
| *A61K 47/36* | (2006.01) |
| *C08J 3/24* | (2006.01) |
| *A61L 15/26* | (2006.01) |
| *A61L 15/44* | (2006.01) |
| *A61L 15/58* | (2006.01) |
| *A61L 27/18* | (2006.01) |
| *A61L 27/26* | (2006.01) |
| *A61L 27/52* | (2006.01) |
| *A61L 27/54* | (2006.01) |
| *C08H 1/06* | (2006.01) |
| *C08L 1/04* | (2006.01) |
| *C08L 1/28* | (2006.01) |
| *C08L 5/04* | (2006.01) |
| *C08L 5/08* | (2006.01) |
| *C08L 89/00* | (2006.01) |
| *A61K 38/00* | (2006.01) |

(52) U.S. Cl.
CPC .............. *C08J 3/246* (2013.01); *A61L 15/26* (2013.01); *A61L 15/44* (2013.01); *A61L 15/585* (2013.01); *A61L 27/18* (2013.01); *A61L 27/26* (2013.01); *A61L 27/52* (2013.01); *A61L 27/54* (2013.01); *C08H 1/06* (2013.01); *C08L 1/04* (2013.01); *C08L 1/286* (2013.01); *C08L 5/04* (2013.01); *C08L 5/08* (2013.01); *C08L 89/00* (2013.01); *A61K 38/00* (2013.01); *C08J 2371/02* (2013.01); *C08J 2389/00* (2013.01)
USPC .......... 424/422; 424/93.1; 424/94.1; 514/1.1; 514/9.7; 514/44 R; 514/773; 514/774; 524/21; 524/22; 527/200; 528/373

(58) Field of Classification Search
CPC . A61K 31/716; A61K 31/722; A61K 31/795; A61K 47/48; A61K 47/34; A61K 47/36; A61K 47/42; A61K 47/4823; A61K 47/48215; A61K 47/48007; A61K 47/48246; A61K 38/02; A61K 38/22; A61K 38/39; A61K 38/43; C08L 5/08; C08L 71/02; C08L 89/00

USPC ........ 424/422, 93.1, 94.1; 514/1.1, 9.7, 44 R, 514/773, 774; 524/21, 22; 527/200; 528/373
See application file for complete search history.

(56) References Cited

U.S. PATENT DOCUMENTS

| | | | |
|---|---|---|---|
| 4,390,519 A | 6/1983 | Sawyer | |
| 2009/0117078 A1* | 5/2009 | Prestwich et al. | ........... 424/93.1 |

OTHER PUBLICATIONS http://en.wikipedia.org/wiki/Hydrogen_bond, pp. 1-11, accessed Jun. 5, 2013.*
Ahluwalia A., et al., "Critical role of hypoxia sensor-HIF-1αin VEGF gene activation. Implication for angiogenesis and tissue injury healing," Curr Med Chem., 2012, 19(1), pp. 90-7.
Allen-Hoffmann B.L., et al., "Normal growth and differentiation in a spontaneously immortalized near-diploid human keratinocyte cell line, NIKS," J Invest Dermatol, 2000, 114(3), pp. 444-455.
Boyce S.T., "Comparative assessment of cultured skin substitutes and native skin autograft for treatment of full-thickness burns," Ann Surg, 1995, 222(6), pp. 743-752.
Boyce S.T., "Cultured skin substitutes combined with Integra® to replace native skin autograft and allograft for closure of full-thickness burns," J Burn Care Rehab, 1999, 20(6), pp. 453-461.
Boyce S.T., "Skin anatomy and antigen expression after burn wound closure with composite grafts of cultured skin cells and biopolymers," Plast Reconstr Surg, 1993, 91(4), pp. 632-641.
Burmania J.A. et al., "Synthesis and physcochemical analysis of interpenetrating networks containing modified gelatin and poly(ethylene glycol) diacrylate," *Journal of Biomedical Materials Research A.*, (2003),vol. 67, No. 1, pp. 224-234.
Chang H.I., "Cell response to surface and architecture of tissue engineering scaffolds. Regenerative Medicine and Tissue Engineering," Cells and Biomaterials. Daniel Eberli (Ed.) InTech, 2011, p. 569.
Chiou, B, et al., "Cold water fish gelatin films: Effects of crosslinking on thermal, mechanical, barrier, and biodegradation properties," *European Polymer Journal*, (2008), vol. 44, pp. 3748-3753.
Clark R.A., et al., "Tissue engineering for cutaneous wounds," J Invest Dermatol, 2007, 127(5), pp. 1018-1029.
Clark R.A., "Wound repair: basic biology to tissue engineering. In principles of tissue engineering," (R. Lanza, R Langer, J.P. Vacanti, 2nd edition) 2000, Elsevier/Academic Press. pp. 857-878.

(Continued)

*Primary Examiner* — Richard Schnizer
*Assistant Examiner* — Alma Pipic
(74) *Attorney, Agent, or Firm* — Foley & Lardner LLP

(57) ABSTRACT

Biomaterials that support cell attachment and growth are provided. In one aspect, biomaterials are provided comprising a first polymer matrix comprising reactive amino moieties and a second polymer matrix that interpenetrates with the first polymer matrix, where the second polymer matrix comprises a poly(alkylene oxide) comprising two or more alkylene oxide oligomers joined by gamma-thioether carbonyl linkages. In another aspect, biomaterials are provided comprising at least one biopolymer comprising amino groups, thiol groups, and bifunctional modifiers connecting at least some of the amino groups to at least some of the thiol groups; and at least one poly(alkylene oxide) cross-linked to at least two thiol groups of the biopolymer. The biomaterials may further comprise a pharmacologically active agent or cells. Methods of administering such biomaterials to a patient in need thereof are also provided.

20 Claims, 29 Drawing Sheets

(56) References Cited

OTHER PUBLICATIONS

Delli Carpini J., "Vascular endothelial growth factors and its relationship to the prognosis and treatment of breast, ovarian, and cervical cancer," Angiogenesis., 2010, 13(1), pp. 43-58.

Detmar M., "Keratinocyte-derived vascular permeability factor (vascular endothelial growth factor) is a potent mitogen for dermal microvascular endothelial cells," J Invest Dermatol, 1995, 105(1), pp. 44-50.

Di Raimondo F., et al., Elevated vascular endothelial growth factor (VEGF) serum levels in idiopathic myelofibrosis. Leukemia., 2001, 15(6), pp. 976-980.

Eaglstein W.H., et al., "Tissue engineering and the development of Apligraf, a human skin equivalent," Clin Ther., 1997, 19(5), pp. 849-905.

Fu, Y. et al., "3D cell entrapment in crosslinked thiolated gelatin-poly(ethylene glycol) diacrylate hydrogels," *Biomaterials*, (2012), vol. 33, pp. 48-58.

Gangatirkar P., et al., "Establishment of 3D orgnaotypic cultures using human neonatal epidermal cells," Nature Protocols., 2007, 2(1), pp. 178-186.

Griffiths M, et al., "Survival of Apligraf in acute human wounds," Tissue Eng., 2004, 10(7-8), pp. 1180-1195.

Guo S, et al., "Factors affecting wound healing," J Dent Res., 2010, 89(3), pp. 219-229.

Hwang et al., "Chemical Modification Strategies for Synthesis of Protein-Based Hydrogel," *J. Agric. Food. Chem.*, Mar. 19, 1996, vol. 44, pp. 751-758.

Jacobi J., "Discordant effects of a soluble VEGF receptor on wound healing and angiogenesis," Gene Ther., 2004, 11(3), pp. 302-309.

Langer A., et al., "Systematic review of economic evaluations of human cell-derived wound care products for the treatment of venous leg and diabetic foot ulcers," BMC Health Serv Res., 2009, 9, 14 pages.

Lee E.Y., et al. Hypoxia-enhanced wound-healing function of adipose-derived stem cells: increase in stem cell proliferation and upregulation of VEGF and bFGF, Wound Repair Regen., 2009, 17(4), pp. 540-547.

Lutolf, M. P. et al., "Synthesis and Physicochemical Characterization of End-Linked Poly(ethylene glycol)-co-peptide Hydroeis Formed by Michael-Type Addition," *Biomacromolecules*, (2003), vol. 4, pp. 713-722.

Marston W.A., et al., "The efficacy and safety of Dermagraft in improving the healing of chronic diabetic foot ulcers: results of a prospective randomized trial," Diabetes Care, 2003, 26(6), pp. 1701-1705.

Miron, T. et al., "A Simplified Method for the Preparation of Succinimidyl Carbonate Polyethylene Glycol for Coupling to Proteins," *Bioconjug. Chem.*, (1993), vol. 4, pp. 568-569.

Ofner, III, Clyde M., et al., "Chemical and Swelling Evaluations of Amino Group Cross Linking in Gelatin and Modified Gelatin Matrices," *Pharmaceutical Research*, (1996), vol. 13, No. 12, pp. 1821-1827.

Pounder, Ryan J. et al., "Metal free thiol-maleimide 'Click' reaction as a mild functionalisation strategy for degradable polymers," *Chem. Commun.*, (2008), pp. 5158-5160, available on-line at www.rsc.org/chemcomm.

Schmidt D.R., et al., "Monocyte activation in response to polyethylene glycol hydrogels grafted with RGD and PHSRN separately by interpositional spacers of various lengths," J Biomed Mater Res A, 2007, 83(3), pp. 617-625.

Schoop V.M., et al., "Epidermal organization and differentiation of HaCaT keratinocytes in organotypic coculture with human dermal fibroblasts," J Invest Dermatol., 1999, 112(3), pp. 343-353.

Schurr M.J., et al., "Phase 1/2 clinical evaluation of StrataGraft: A consistent, pathogen-free human skin substitute," J Trauma., 2009, 66(3), pp. 866-873.

Shevchenko R.V., et al., "A review of tissue-engineered skin bioconstructs available for skin reconstruction," J R Soc Interface., 2010, 7(43), pp. 229-258.

Tingstrom A., "Regulation of fibroblast-mediated collagen gel contraction by platelet-derived growth factor, interleukin-1 alpha and transforming growth factor-beta 1," J Cell Sci., 1992, 102(2), pp. 315-322.

Van de Wetering, P. et al., "Poly(ethylene glycol) hydrogels formed by conjugate additional with controllable swelling, degradation, and release of pharmaceutically active proteins," *Journal of Controlled Release*, (2005), vol. 102, pp. 619-627; available online at www.sciencedirect.com.

Wang L., et al., "Chemical and physical modifications to poly(dimethylsloxane) surface affect adhesion of Caco-2 cells," J Biomed Mater Res A., 2010, 93(4), pp. 1260-1271.

Werner, S., et al., "Keratinocyte—Fibroblast Interactions in Wound Healing," *J. Invest. Dermatol*, (2007), vol. 127, pp. 998-1008.

Ghosh, K, et al., "Wound Repair," Principles of Tissue Engineering, $3^{rd}$ Edition, 2007, pp. 1149-1166.

Waknine, Yael, "Diabetic Ulcer Gel Gets Black Box Warning," Medscape Medical News, Jun. 9, 2008, 1 page.

Xu K, Fu Y, Chung W, Zheng XX, Cui Y, Hsu IC, Kao WJ. "Thiol-Ene based biologic/synthetic hybrid biomatrix for 3-D living cell culture," Acta Biomaterialia, 2012, 8, pp. 2504-2516. PMID: 22484717. NIHMSID: NIHMS429532.

* cited by examiner

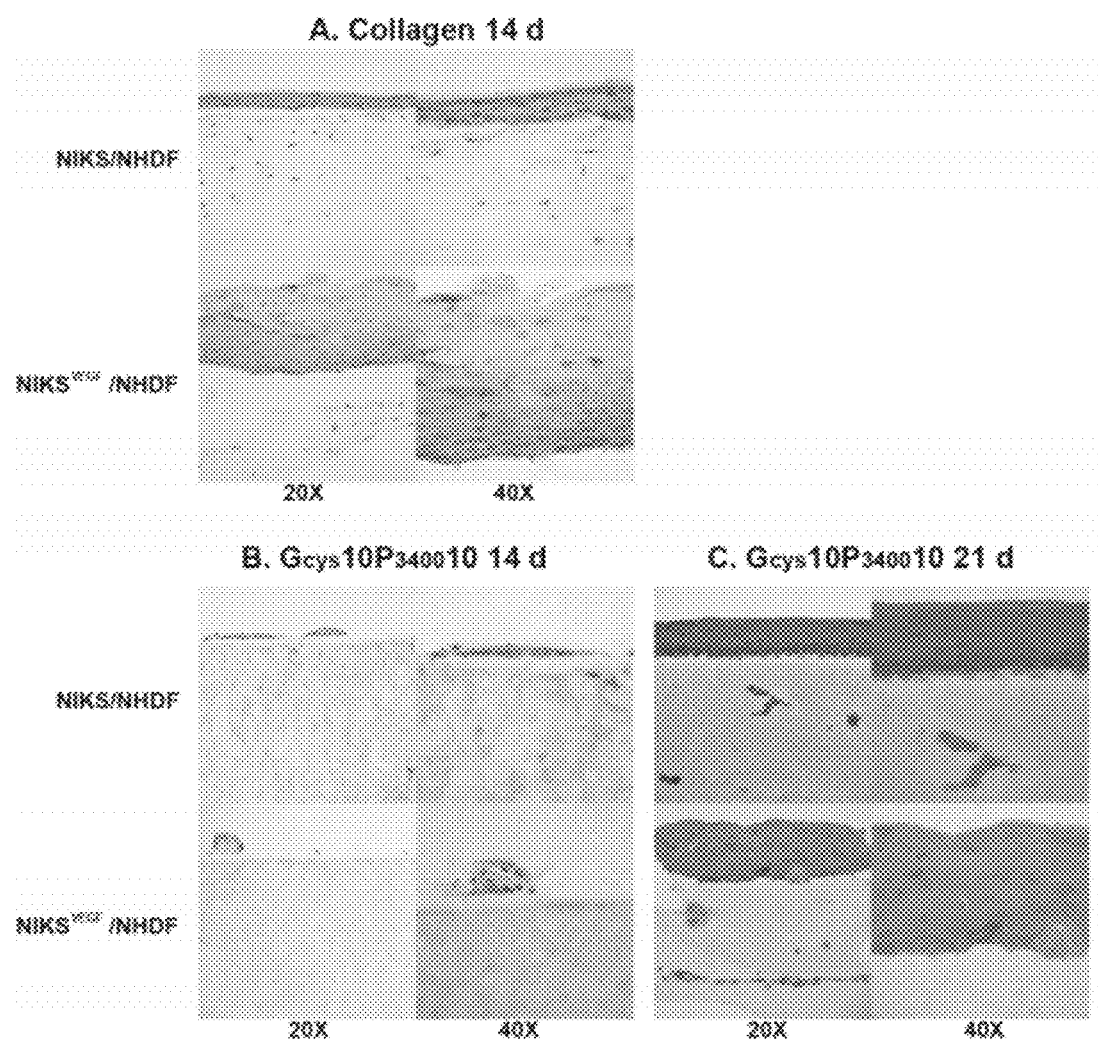

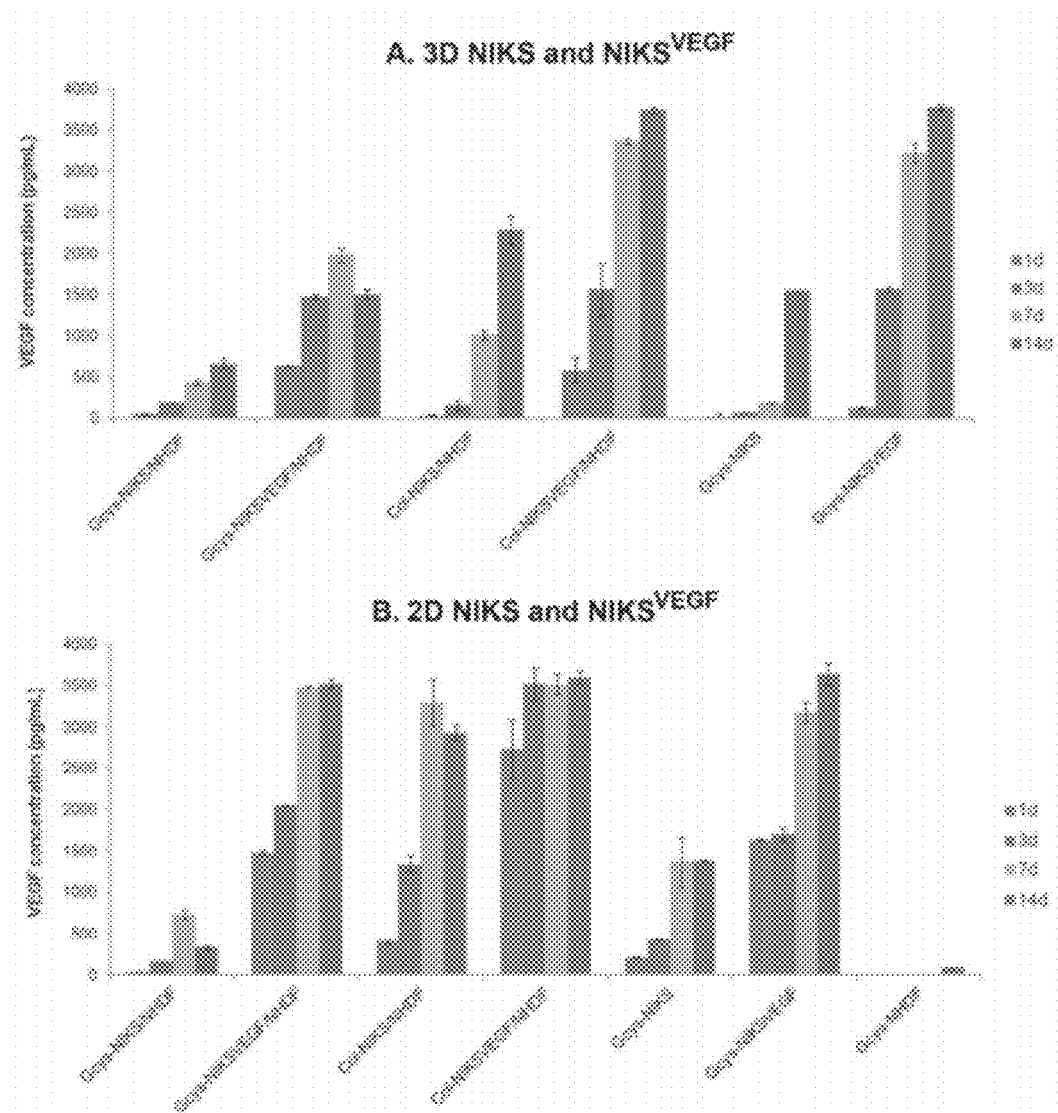

MULTIFUNCTIONAL IN SITU POLYMERIZED NETWORK VIA THIOL-ENE AND THIOL-MALEIMIDE CHEMISTRY

CROSS-REFERENCE TO RELATED APPLICATIONS

This application claims priority to U.S. Provisional Application No. 61/448,543 filed Mar. 2, 2011, which is incorporated herein by reference in its entirety.

GOVERNMENT RIGHTS

This invention was made with government support under EB006613 awarded by the National Institutes of Health. The government has certain rights in the invention.

SUMMARY

In one aspect, the present technology relates to biomaterials comprising interpenetrating polymer matrices, as well as methods of using such biomaterials. More specifically, the biomaterials include a first polymer matrix including reactive amino moieties and second polymer matrix that interpenetrates with the first polymer matrix. The second polymer matrix includes a poly(alkylene oxide), having two or more alkylene oxide oligomers. The alkylene oxide oligomers are joined through gamma-thioether carbonyl linkages.

As disclosed herein, a variety of reactive amine-functionalized polymers may be employed as the first polymer matrix, including, but not limited to, gelatin, collagen, alginate salts, cellulose derivatives, whey protein, chitosan, hyaluronic acid or combinations thereof. The first polymer matrix may be further functionalized with homo- or heterobifunctional polyalkylene glycol modifiers. Such bifunctional modifiers serve as covalent grafts to modify the physical, chemical, and biological properties of the resultant biomaterials. For example, bifunctional agents conjugated with pharmacologically-active agents may be grafted to the first polymer matrix, and thus incorporated into the biomaterial. The first polymer matrix may also be modified through cross-linking or treated with an appropriate reagent as to install new chemical functional groups as desired.

As further described in the Examples herein, the biomaterials of the present technology are prepared by in situ polymerization of appropriately functionalized alkylene oxide oligomers in the presence of the first polymer matrix. In one aspect, the alkylene oxide oligomers may be modified as to include thiol and reactive olefinic groups, such that upon polymerization, the resultant poly(alkylene oxide) comprises gamma-thioether carbonyl linkages via. Michael addition of thiol groups to the reactive olefins (i.e., a thiol-ene reaction). Because the polymerization reaction proceeds in the presence of the first polymer matrix, the second polymer matrix interpenetrates with the first polymer matrix within the biomaterial. Notably, the thiol-ene polymerization proceeds in the absence of an external energy source such as UV light. Thus the clinical applicability of the technology is greatly enhanced, particularly if therapeutics or viable cells are to be incorporated into the biomaterial. Moreover, the polymerization proceeds under mild conditions compatible with physiological conditions (e.g., in air, in aqueous solvents, at moderate pHs, and at rapid rates between room and physiological temperatures).

In another aspect of the present technology, biomaterials are provided that include at least one biopolymer comprising amino groups, thiol groups, and bifunctional modifiers connecting at least some of the amino groups to at least some of the thiol groups; and at least one poly(alkylene oxide) cross-linked to at least two thiol groups of the biopolymer. Such hybrid biomaterials reliably provide the strength and mechanical stability of synthetic matrices and the biofunctionality needed to actively support cell growth, differentiation and migration. Hence, the biomaterials of the present technology all contain multi-parametric factors that can easily be controlled to modulate the chemical, physical, and biological properties of the materials for soft tissue scaffolding and cell presentation, and allow the materials to recapitulate lost tissue architecture and physical functionality.

Biomaterials of the present technology may comprise a pharmaceutically active agent either entrained within the biomaterial or covalently attached to the first polymer matrix. In the latter case, the covalent attachment may be through the bifunctional modifier. Additionally or alternatively, living cells may be entrained in the biomaterial. Thus, such biomaterials of the present technology may be implanted into a patient in need of such pharmaceutically active agent and/or cells.

BRIEF DESCRIPTION OF THE DRAWINGS

FIG. 15A: complex shear modulus (G*) value of type A gelatin-PEG hydrogels with swollen status (black bars) versus un-swollen status (white bars). FIG. 15B: complex shear modulus of type A gelatin-PEG hydrogels (white bars) and type B gelatin-PEG hydrogel (black bars) with completely swollen status. FIG. 15C: complex shear modulus of cell encapsulated type A gelatin-PEG hydrogels after 14 days culture (black bars) versus cell free samples (white bars). ** $p<0.01$, * $p<0.05$.

FIG. 16A: Swelling profiles of gelatin-PEG hydrogels with type A Gel-PEG-Cys (◆:GA5P5, ■: GA10P5, ▲: GA15P5, □: GA10P7.5, ○: GA10P10). FIG. 16B: Swelling profiles of gelatin-PEG hydrogels with type B Gel-PEG-Cys (◆:GB5P5, ■: GB10P5, ▲: GB15P5, □: GB10P7.5, ○: GB10P10).

FIG. 17A: gelatin dissolution behavior of type A gelatin-PEG hydrogels (◆:GA5P5, ■: GA10P5, ▲: GA15P5, □: GA10P7.5, ○: GA10P10). FIG. 17B: gelatin dissolution behavior of type B gelatin-PEG hydrogels (◆: GB5P5, ■: GB10P5, ▲: GB15P5, □: GB10P7.5, ○: GB10P10).

FIG. 18A: 4,000 Da; FIG. 18B: 70,000 Da; FIG. 18C: 500,000 Da.

FIG. 22A: F-actin morphology of cells entrapped in type A or type B gelatin-PEG hydrogels. FIG. 22B: Cell morphology in GA10P10 and GA15P5 hydrogel. Images were taken from four different depths of the hydrogel with 50 μm intervals between each depth. FIG. 22C: fibroblasts spread inside the GB15P3 hydrogel. Scale bar=200 μm.

(FIG. 27B) 2D NIKS and NIKS$^{VEGF}$ morphology on 3D cocultured NHDF encapsulated matrices 14 d after seeding: (a), $G_{cys}10P_{3400}10$, top scan; (b), $G_{cys}10P_{3400}10$, bottom scan; and (c) NHDF encapsulated in $G_{cys}10P_{3400}10$ hydrogel. Cell cytoskeleton was stained with Alex-488 conjugated phalloidin. (Magnification, 20×)

FIGS. 28A, 28B and 28C Histologic sections of the 2D NIKS/NIKS$^{VEGF}$ in 3D coculture with NHDF encapsulated in (FIG. 28A) collagen, (FIG. 28B) thiolated gelatin-PEGdA hydrogel $G_{cys}10P_{3400}10$, 14 days after coculturing, and (FIG. 28C) thiolated gelatin-PEGdA hydrogel $G_{cys}10P_{3400}10$, 21 days after coculturing. Samples were fixed, sectioned and stained with hematoxylin and eosin. Sections were viewed and photographed.

FIGS. 29A and 29B VEGF expression from 3D NIKS/NIKS$^{VEGF}$ and 3D NHDF organotypic coculture (FIG. 29A) and 2D NIKS/NIKS$^{VEGF}$ and (FIG. 29B) 3D NHDF organotypic coculture. Data represented as mean±S.D. (n=3).

DETAILED DESCRIPTION

Figure 1:
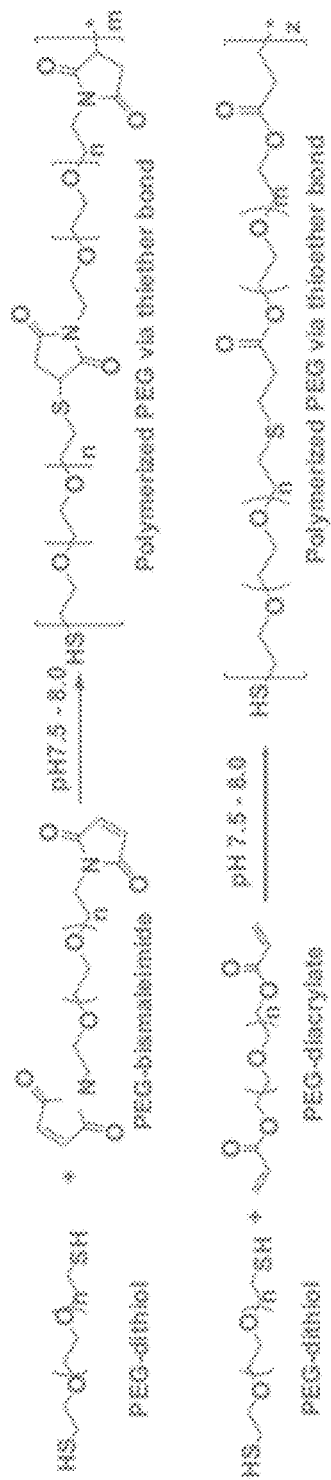
FIG. 1 shows synthetic schemes for preparation of PEG biomaterials via (a) reaction of PEG-dithiol with PEG-diacrylate through addition of thiol groups to acrylate carbon-carbon double bonds (i.e., thiol-ene addition) and (b) reaction of PEG-dithiol with PEG-dimaleimide through addition of the thiol groups to maleimide carbon-carbon double bonds (i.e., thiol-maleimide addition). In either case, the two ethylene oxide oligomers are joined by gamma-thioether carbonyl linkages after a thiol-ene or thiol-maleimide reaction.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

ABBREVIATIONS AND DEFINITIONS

"AC"=acrylate
"Da"=Dalton
"DPBS"=Dulbecco's phosphate buffered saline
"DPBSE"=Dulbecco's phosphate buffered saline, modified with EDTA
"ddH$_2$O"=double distilled water
"FBS"=fetal bovine serum
"IMDM"=Iscove's modified Dulbecco's media
"KGM"=keratinocyte growth medium
"PBS"=phosphate buffered saline
"PEG" and "PEG-diol"=polyethylene glycol
"PEG2K"=polyethylene glycol with a molecular weight of ~2,000 Da
"PEG-diacrylate" and "PEGdA"=polyethylene glycol diacrylate
"PEG-dithiol" and "SH-PEG-SH"=polyethylene glycol dithiol
"PEG-ditosylate" and "Tos-PEG-Tos"=polyethylene glycol di-p-toluenesulfonate
"PEG-dimaleimide" and "Mal-PEG-Mal"=polyethylene glycol dimaleimide
"sIPN"=semi-interpenetrating network(s)
"TCPS"=tissue culture polystyrene
"THF"=tetrahydrofuran
"TEOA"=triethanolamine The term "alkyl," by itself or as part of another substituent, means, unless otherwise stated, a fully saturated, straight, branched chain, or cyclic hydrocarbon radical, or combination thereof, and can include di- and multi-valent radicals, having the number of carbon atoms designated (e.g., $C_1$-$C_{10}$ means from one to ten carbon atoms, inclusive). A cyclic alkyl group may also be referred to as a "cycloalkyl." Examples of alkyl groups include, without limitation, methyl, ethyl, n-propyl, isopropyl, n-butyl, t-butyl, isobutyl, sec-butyl, cyclohexyl, (cyclohexyl)ethyl, cyclopropylmethyl, and homologs and isomers thereof, for example, n-pentyl, n-hexyl, n-heptyl, n-octyl, and the like. The term "alkyl," unless otherwise noted, also includes those derivatives of alkyl defined in more detail below as "heteroalkyl" and "cycloheteroalkyl."

The term "alkenyl" means an alkyl group as defined above containing one or more double bonds. Examples of alkenyl groups include vinyl, 2-propenyl, crotyl, 2-isopentenyl, 2-(butadienyl), 2,4-pentadienyl, 3-(1,4-pentadienyl), etc., and the higher homologs and isomers.

The term "alkynyl" means an alkyl or alkenyl group as defined above containing one or more triple bonds. Examples of alkynyl groups include ethynyl, 1- and 3-propynyl, 3-butynyl, and the like, including the higher homologs and isomers.

The terms "alkylene," "alkenylene," and "alkynylene," alone or as part of another substituent means a divalent radical derived from an alkyl, alkenyl, or alkynyl group, respectively, as exemplified by —CH$_2$CH$_2$CH$_2$CH$_2$—.

Typically, alkyl and alkylene groups will have from 1 to 24 carbon atoms, while alkenyl, alkynyl, alkenylene, and alkynylene groups will have from 2 to 24 carbon atoms. Those groups having 10 or fewer carbon atoms are preferred in the present technology. The term "lower" when applied to any of these groups, as in "lower alkyl" or "lower alkylene," designates a group having eight or fewer carbon atoms.

The term "heteroalkyl," by itself or in combination with another term, means, unless otherwise stated, a stable, saturated or unsaturated, straight, branched chain, or cyclic hydrocarbon radical, or combinations thereof, consisting of the stated number of carbon atoms and from one to three heteroatoms selected from the group consisting of O, N, Si, and S, and wherein the nitrogen and sulfur atoms may optionally be oxidized and the nitrogen heteroatom(s) may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —CH$_2$—CH$_2$—O—CH$_3$, —CH$_2$—CH$_2$—NH—CH$_3$, N(CH$_3$)—CH$_3$, —CH$_2$—S—CH$_2$—CH$_3$, —CH$_2$—O—CH$_2$—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as in —CH$_2$—NH—O—CH$_3$ and —CH$_2$—O—Si(CH$_3$)$_3$. Explicitly included within the term "heteroalkyl" are those radicals that could also be described as "heteroalkylene" (i.e., a divalent radical, see below), and "cycloheteroalkyl" (i.e., containing a cyclic group in which at least one ring member is a heteroatom). The term "heteroalkyl" also explicitly includes unsaturated groups (i.e., heteroalkenyls and heteroalkynyls).

The term "cycloheteroalkyl," includes aromatic (also referred to as heteroaryl) and non-aromatic ring compounds containing 3 or more ring members, of which one or more is a heteroatom such as, but not limited to, N, O, and S. In some embodiments, the cycloheteroalkyl group contains 1, 2, 3 or 4 heteroatoms. In some embodiments, cycloheteroalkyl groups include mono-, bi- and tricyclic rings having 3 to 16 ring members, whereas other such groups have 3 to 6, 3 to 10, 3 to 12, or 3 to 14 ring members. Cycloheteroalkyl groups encompass aromatic, partially unsaturated and saturated ring systems, such as, for example, imidazolyl, imidazolinyl and imidazolidinyl groups. Thus, the term "cycloheteroalkyl" also includes cycloheteroalkenyl ring species. The term "cycloheteroalkyl" also includes fused ring species including those comprising fused aromatic and non-aromatic groups, such as, for example, benzotriazolyl, 2,3-dihydrobenzo[1,4]dioxinyl, and benzo[1,3]dioxolyl. The term also includes bridged polycyclic ring systems containing a heteroatom such as, but not limited to, quinuclidyl. Other cycloheteroalkyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups.

The term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini. Still further, for alkylene and heteroalkylene linking groups, no orientation of the linking group is implied.

The term "aryl" is used herein to refer to an aromatic substituent, which may be a single aromatic ring or multiple (typically 2 or 3) aromatic rings which are fused together, linked covalently, or linked to a common group such as a diazo, methylene or ethylene moiety. The common linking group may also be a carbonyl as in benzophenone. The aromatic ring(s) may include, for example phenyl, naphthyl, biphenyl, diphenylmethyl and benzophenone, among others. The term "aryl" encompasses "arylalkyl" and "substituted aryl." For phenyl groups, the aryl ring may be mono-, di-, tri-, tetra-, or penta-substituted. Larger rings may be unsubstituted or bear one or more substituents.

"Substituted" refers to a chemical group as described herein that further includes one or more substituents, such as lower alkyl (including substituted lower alkyl such as haloalkyl, hydroxyalkyl, aminoalkyl), aryl (including substituted aryl), acyl, halogen, hydroxy, amino, alkoxy, alkylamino, acylamino, thioamido, acyloxy, aryloxy, aryloxyalkyl, carboxy, thiol, sulfide, sulfonyl, oxo, both saturated and unsaturated cyclic hydrocarbons (e.g., cycloalkyl, cycloalkenyl), cycloheteroalkyls and the like. These groups may be attached to any carbon or substituent of the alkyl, alkenyl, alkynyl, aryl, cycloheteroalkyl, alkylene, alkenylene, alkynyleue, arylene, hetero moieties. Additionally, the substituents may be pendent from, or integral to, the carbon chain itself.

The term "acyl" is used to describe a carbonyl-containing substituent, —C(O)R, where R is —H or substituted or unsubstituted alkyl, alkenyl, alkynyl, or aryl as defined herein.

The term "alkoxy" is used herein to refer to the —OR group, where R is monovalent or divalent alkyl, alkenyl, alkynyl, or a substituted analog thereof. Suitable alkoxy radicals include, for example, methoxy, ethoxy, t-butoxy, etc. The term "alkoxyallyl" refers to ether substituents, monovalent or divalent, e.g., —$CH_2$—O—$CH_3$ and —$CH_2$—O—$CH_2$—.

The term "aryloxy" is used herein to refer to —O-aryl groups where the aryl is substituted or unsubstituted as defined above and may be mono or divalent. Examples of aryloxy groups include but are not limited to phenoxy, naphthyloxy, tolyloxy, and 2-chlorophenyloxy.

The term "amino" is used to designate NRR', wherein R and R' are independently H, alkyl, alkenyl, alkynyl, aryl or substituted analogs thereof. Thus, "amino" includes primary, secondary and tertiary amines, and "acylamino" describing the group RC(O)NR'.

The term "carbonyl" is used to describe a C═O substituent. "Oxo" refers to the double bonded oxygen in a carbonyl.

The term "carboxy" refers to an ester substituent or carboxylic acid, i.e., RC(O)O—, —C(O)OR, or —C(O)—OH. The R group can be a substituted or unsubstituted alkyl, alkenyl, alkynyl, aryl, or cycloheteroalkyl group.

The term "halogen" or "halo" is used herein to refer to fluorine, bromine, chlorine and iodine atoms.

The term "hydroxy" is used herein to refer to the group —OH.

The term "sulfonate" is used herein to refer to —$SO_3H$, $RSO_2O$— or —$SO_2OR$ groups. The R group can be a substituted or unsubstituted alkyl, alkenyl, alkynyl, aryl, or cycloheteroalkyl group.

The term "thiol" is used herein to refer to —SH groups, while sulfides include —S— groups.

The term "gelatin" as used herein means any and all kinds of gelatin, of any type (e.g., Type A from pork, with an isoelectric point between about 7.0 and 9.0, and Type B from beef with an isoelectric point of approximately 5.0), from any source, of any bloom value, acid- or alkaline-treated, etc., without limitation. The "bloom strength" of a gelatin is defined as the force required for a plunger of defined shape and size to make a 4 mm depression in a gel that has been prepared at 6.67% w/w concentration and chilled at 10° C. in a bloom jar for 16-18 hours. The force is recorded in grams. Commercially, gelatin is available from a host of commercial suppliers. At commodity amounts and prices, gelatin is generally available with bloom strengths ranging from about 50-300 bloom. Such gelatins are available from, for example, Leiner Davis Gelatin, a wholly-owned subsidiary of Goodman Fielder Ingredients of Sydney, Australia. Gelatins having bloom values outside this range are also available as specialty chemicals and are included within the scope of the term "gelatin." For example a zero bloom (non-gelling) gelatin is available from Great Lakes Gelatin Co., Grayslake, Ill.

Likewise, the term "collagen" as used herein means any and all kinds of collagen, of any type, from any source, without limitation. Cross-linked collagen, esterified collagen, and chemically-modified collagen, such as that taught by U.S. Pat. No. 4,390,519, are included with the term "collagen."

The term "oligomer" as used herein means a short polymer or macromonomer made up of from 2 to about 500 subunits or monomers.

The term "polymer matrix" encompasses any type of polymer matrix that can function as a biomaterial, e.g., a hydrogel, including, without limitation, gelatin, calcium alginate, calcium/sodium alginate, collagen, oxidized regenerated cellulose, carboxymethylcellulose, amino-modified celluloses, such as 6-deoxy-6-(4-aminophenyl)-amino-2(3)-O-tosylcellulose, whey protein gels, chitosan, hyaluronic acid and the like.

The term "semi-interpenetrating polymer network" or "sIPN" as used herein means a polymer comprising one or more networks and one or more linear or branched polymer(s) characterized by the penetration on a molecular scale of at least one of the networks by at least some of the linear or branched macromolecules. Semi-interpenetrating polymer networks are distinguished from interpenetrating polymer networks because the constituent linear or branched polymers can, in principle, be separated from the constituent polymer network(s) without breaking chemical bonds.

The present technology provides for biomaterials which include a first polymer matrix which includes reactive amino moieties and second polymer matrix which interpenetrates with the first polymer matrix. The second polymer matrix includes a poly(alkylene oxide) which is comprised of two or more alkylene oxide oligomers joined by gamma-thioether carbonyl linkages. Thus, the second polymer matrix, interpenetrates and is physically entrapped and/or entangled within the first polymer matrix. The second polymer matrix may be entrapped with, or entangle with, the first polymer matrix because of the manner in which the second polymer matrix is formed. For example, if the second polymer matrix is formed by an in situ polymerization in the presence of a first polymer matrix, the second polymer matrix may interpenetrate with the first polymer matrix. A further aspect of the present technology is that the biomaterials may be in the form of hydrogels. Hydrogels are three-dimensional networks capable of absorbing copious amounts of water. Hydrogels have been explored for many uses, including drug delivery devices, wound dressing materials, contact lenses, and cell transplantation matrices. Edible hydrogels, such as gelatin, find extensive use in various food-related applications, such as texture modification, gelling, clarification of beers and wines, and as medicine capsules.

In accordance with one aspect of the present technology, the first polymer matrix includes reactive amino moieties. While there is no requirement that the first polymer matrix be naturally occurring, there are numerous examples of natural polymers and modified natural polymers possessing reactive amino groups. Examples include but are not limited to gelatin, calcium alginate, calcium/sodium alginate, collagen, oxidized regenerated cellulose, carboxymethylcellulose, amino-modified cellulose, whey protein, chitosan, hyaluronic acid and combinations of any two or more thereof. In one embodiment of the present technology, gelatin and/or collagen are used for the first polymer matrix.

In one aspect of the present technology, the first polymer matrix optionally includes a homo- or heterobifunctional modifier of the following formula:

$$-A-[(CR^1R^2)_m-O]_n-Z-. \qquad I$$

In such modifiers, at least one of A or Z is covalently bonded to the reactive amino moieties of the first polymer matrix; such that at least one of A and Z is a divalent moiety selected from the group consisting of —O—, —S—, $C_{2-24}$-alkenyl, $C_{2-24}$-alkynyl, $C_{1-24}$-heteroalkyl, $C_{2-24}$-heteroalkenyl, $C_{2-24}$-heteroalkynyl, cyano-$C_{1-24}$-alkyl, $C_{3-10}$-cycloalkyl, $C_{3-10}$-cycloalkenyl, $C_{3-10}$-cycloheteroalkyl, $C_{3-10}$-cycloheteroalkenyl, acyl, acyl-$C_{1-24}$-alkyl, acyl-$C_{1-24}$-alkenyl, acyl-$C_{1-24}$-alkynyl, carboxy, $C_{1-24}$-alkylcarboxy, $C_{1-24}$-alkenylcarboxy, $C_{1-24}$-alkynylcarboxy, carboxy-$C_{1-24}$-alkyl, carboxy-$C_{2-24}$-alkenyl, carboxy-$C_{1-24}$-alkynyl, aryl, aryl-$C_{1-24}$-alkyl, aryl-$C_{1-24}$-alkenyl, aryl-$C_{2-24}$-alkynyl, heteroaryl, heteroaryl-$C_{1-24}$-alkyl, heteroaryl-$C_{2-24}$-alkenyl, heteroaryl-$C_{1-24}$alkynyl, sulfonate, arylsulfonate, and heteroarylsulfonate; at each occurrence $R^1$ and $R^2$ is independently selected from the group consisting of H, methyl, and ethyl; m is an integer from 2 to 8; and n is an integer equal to or greater than 30.

In another embodiment, one of A and Z of formula I is a monovalent moiety selected from the group consisting of halo, hydroxy, thiol, amino, $C_{1-24}$-alkyl, $C_{2-24}$-alkenyl, $C_{1-24}$-alkoxy, $C_{1-24}$-heteroalkyl, $C_{1-24}$-heteroalkenyl, $C_{1-24}$-heteroalkynyl, cyano-$C_{1-24}$-alkyl, $C_{3-10}$-cycloalkyl, $C_{3-10}$-cycloalkenyl, $C_{3-10}$-cycloheteroalkyl, $C_{3-10}$-cycloheteroalkenyl, acyl, alkyl, acyl-$C_{1-24}$-alkenyl, acyl-$C_{1-24}$-alkynyl, carboxy, $C_{1-24}$-allylcarboxy, $C_{1-24}$-alkenylcarboxy, $C_{1-24}$-alkynylcarboxy, carboxy-$C_{1-24}$-allyl, carboxy-$C_{2-24}$-alkenyl, carboxy-$C_{2-24}$-alkynyl, aryl, aryl-$C_{1-24}$-alkyl, heteroaryl, heteroaryl-$C_{1-24}$-alkyl, heteroaryl-$C_{2-24}$-alkenyl, heteroaryl-$C_{2-24}$-alkynyl, sulfonate, arylsulfonate, and heteroarylsulfonate.

In yet a further embodiment, both A and Z of formula I are divalent moieties selected from the group consisting of —O—, —S—, —NH—, $C_{1-24}$-alkyl, $C_{2-24}$-alkenyl, $C_{1-24}$-alkoxy, $C_{1-24}$-heteroalkyl, $C_{2-24}$-heteroallcenyl, $C_{2-24}$-heteroalkynyl, cyano-$C_{1-24}$-alkyl, $C_{3-10}$-cycloalkyl, $C_{3-10}$-cycloalkenyl, $C_{3-10}$-cycloheteroalkyl, $C_{3-10}$-cycloheteroalkenyl, acyl, acyl-$C_{1-24}$-alkyl, acyl-$C_{1-24}$-alkenyl, acyl-$C_{1-24}$-alkynyl, carboxy, $C_{1-24}$-alkylcarboxy, $C_{1-24}$-alkenylcarboxy, $C_{1-24}$-alkynylcarboxy, carboxy-$C_{1-24}$-alkyl, carboxy-$C_{7-74}$-alkenyl, carboxy-$C_{1-24}$-alkynyl, aryl, aryl-$C_{1-24}$-alkyl, aryl-$C_{2-24}$-alkenyl, aryl-$C_{2-24}$-alkynyl, heteroaryl, heteroaryl-$C_{1-24}$-alkyl, heteroaryl-$C_{2-24}$-alkenyl, heteroaryl-$C_{1-24}$-alkynyl, sulfonate, arylsulfonate, and heteroarylsulfonate.

As noted above, m is an integer from 2 to 8. In some embodiments m is 2, 3, 4, 5, 6 or 7. In certain embodiments, in is 2, 3, or 4. In some embodiments, at each occurrence and $R^2$ are independently H or methyl, while in others $R^1$ and $R^2$ are both H. Thus, for example, the poly(alkylene oxide) portion of formula I may be, but is not limited to, poly(ethylene glycol) or poly(propylene glycol).

In a further embodiment, n of formula I is equal to or greater than 200, or is equal or greater than 2,000, or is equal or greater than 20,000. Examples of n of formula I include but are not limited to 1, 5, 10, 20, 30, 50, 100, 200, 300, 400, 500, 1,000, 2,000, 4,000, 10,000, 15,000, 20,000, and any range between and/or including two or more of these values. Thus, n may be, e.g., an integer from 1 to 20,000 or 10 to 2,000, and so forth.

By incorporation of such bifunctional modifiers into the first polymer matrix, the properties of the biomaterial, such as hydrophilicity, porosity, swelling, degradation, mechanical properties, loading capacity for a pharmacologically-active agent, release kinetics of a pharmacologically-active agent, etc. may be adjusted through tuning of the physical and chemical properties of the bifunctional modifier. For example, bifunctional PEG modifiers may improve hydrophilicity and solubility of gelatin (a non-limiting example of a first polymer matrix), which will further influence swelling, degradation, and mechanical properties of the semi-interpenetrating polymer network once formed. Linear PEG modifiers may serve as hydrophilic brushes associated on the gelatin backbone, which may reduce the potential electrostatic interactions between ionized gelatin and solutes and thus facilitate the release of hydrophilic solutes. Bifunctional modifiers including a PEG-poly(lactic acid)-PEG segment may impart the ability to degrade (e.g., in vivo) to the first polymer matrix, and may also vary the hydrophilicity/hydrophobicity of the first polymer matrix. The molecular weight of the bifunctional modifier may be tuned to adjust the degree of exposure of biofunctional ligands and/or probes at the surface of the biomaterial.

The aforementioned properties may be also adjusted through incorporation of cross-links within the tint polymer matrix or by treating the first polymer matrix with an appropriate reagent as to include additional chemical functionalities within the matrix. For example, the first polymer matrix may be cross-linked with about 0.001 wt % to about 10 wt. % of a cross-linking agent known in the art. Examples of amounts of cross-linking agents that may be used include about 0.001 wt %, about 0.005 wt %, about 0.01 wt %, about 0.05 wt %, about 0.1 wt %, about 0.2 wt %, about 0.5 wt %, about 1 wt %, about 2 wt %, about 5 wt %, about 7 wt %, about 10 wt %, and ranges between and including any two of these values. Where the first polymer matrix is gelatin, cross-linking agents including but not limited to glutaraldehyde, a carbodiimide (e.g., EDC, DCC, DIC, and the like), formaldehyde, transglutaminase, genipin, glyoxal, ferrulic acid, and tannic acid may be used effectively ((a) *European Polymer Journal* (2008), 44, 3748-3753; (b) Pharmaceutical Research (1996), 13, 1821-1827).

Alternatively, the first polymer matrix may be treated with a reagent which will introduce additional chemical functionality within the matrix. For example, in one embodiment of the present technology, the first polymer matrix is gelatin and the lysyl residues of gelatin are modified with an ampholytic moiety such as ethylenediaminetetracetic dianhydride (EDTAD). Modification of gelatin with EDTAD results in the introduction of polyanionic molecules into the gelatin chain, thereby improving the swelling capability of the gelatin-based biomaterials. Further, EDTAD has low toxicity and the reaction of gelatin with EDTAD is a fast and facile process (Hwang & Damodaran *J. Agric. Food. Chem.* (1996), 44, 751-758). In another embodiment, the first polymer matrix is gelatin and the lysyl residues of gelatin are modified to introduce free thiol groups via a bifunctional linker.

In accordance with another aspect of the present technology, the second polymer matrix includes a poly(alkylene oxide) polymer which includes two or more alkylene oxide oligomers joined by gamma-thioether carbonyl linkages. In a broad form, a gamma-thioether carbonyl linkage takes the form of the general structure in formula II, below.

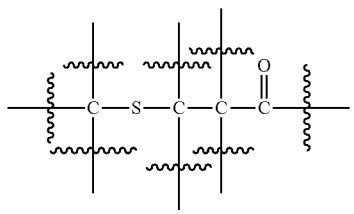

II

Generally, gamma-thioether carbonyl linkages may be readily prepared through a thiol-ene reaction of a thiol-containing compound with an α,β-unsaturated carbonyl compound via Michael-type addition (7-15). Examples of suitable α,β-unsaturated carbonyl compounds include α,β-unsaturated esters (e.g., acrylate esters and derivatives thereof), amides, imides, and ketones. Where the gamma-thioether carbonyl linkages are prepared through the reaction of thiol group with a maleimide group (an unsaturated cyclic imide) as the Michael acceptor, such a reaction is referred herein as a thiol-maleimide reaction. Notably, thiol-ene and thiol-maleimide reactions of the present technology are high-yielding, clean, and do not require the an external radiation source such as UV light. Thiol-ene and thiol-maleimide reactions may also be catalyzed by base. However, it has been discovered that simple dithiols such as ethanedithiol do not readily link poly(alkylene oxide) oligomers or polymers bearing Michel acceptors; larger dithiols, e.g., oligomeric dithiols, e.g., oligomeric alkylene oxides are used instead.

Thiol groups and α,β-unsaturated carbonyl groups may be easily introduced into alkylene oxide oligomers by functionalizing such oligomers with an appropriate reagent. For example alkylene oxide oligomers such as poly(ethylene glycol), i.e., PEG-diol or simply PEG, possess terminal hydroxy groups which may be functionalized. As used herein, it is understood that the term alkylene oxide oligomer includes functionalized poly(alkylene glycol). In one embodiment of the present technology, the alkylene oxide oligomer is a functionalized poly(ethylene glycol). In another embodiment, the alkylene oxide oligomer is a functionalized poly(propylene glycol).

Functionalization of PEG-diol is described in Examples 1 and 2. Briefly, reaction of PEG-diol with p-toluenesulfonyl chloride provides PEG-ditosylate. Treatment of PEG-ditosylate with sodium hydrosulfide results in displacement of the tosyl groups to give PEG-dithiol. PEG-diol may also be derivatized with acryloyl chloride to provide acrylate functionalized PEG-diacrylate (Example 2). PEG-diacrylate, PEG-dimaleimide, and PEG dithiol are commercially available at certain molecular weights.

As illustrated in FIG. 1 and further described in Example 3A1, in the presence of base, PEG-dithiol reacts with PEG-diacrylate via a thiol-ene reaction to give a hydrogel with gamma-thioether carbonyl linkages. Likewise, PEG-dithiol reacts with PEG-dimaleimide via a thiol-maleimide reaction to give a hydrogel also including gamma-thioether carbonyl linkages (FIG. 1 and Example 3B1).

The above described hydrogels can be used as a second polymer matrix that interpenetrates with a first polymer matrix which includes reactive amino moieties. In this aspect of the technology, the thiol-ene or thiol-maleimide reaction is allowed to proceed in the presence of the first polymer matrix via an in situ polymerization reaction, thereby forming a second polymer matrix that interpenetrates the first polymer matrix. Thus, the second polymer matrix is physically, but not covalently, bound within the first polymer matrix. When the first polymer matrix includes reactive amino moieties, the resultant material is a biomaterial of the present technology. For instance, as described in Example 3A2 and illustrated in FIG. 3, a biomaterial may be prepared by the reaction of PEG-dithiol with PEG-diacrylate in the presence of gelatin. Similarly, biomaterials may be obtained by reaction of PEG-dithiol with PEG-dimaleimide in the presence of gelatin (Example 3B2, FIG. 3). Notably, neither of these examples require an external radiation source (e.g., infrared, visible, or ultraviolet light) to initiate the in situ polymerization reaction to prepare the biomaterial. Thus, by removing the need for a light source (and associated equipment) as well as the possible need for highly toxic photoinitiators, the clinical applicability of such a biomaterial is greatly enhanced. Moreover, the biomaterials described herein may be prepared at or near physiological conditions, i.e., in aqueous solution and at moderate temperatures.

In one embodiment of the technology, the biomaterial includes a second polymer matrix which comprises alkylene oxide oligomers selected from poly(ethylene glycol) and polypropylene glycol). Examples 3A2 and 3B2 describe biomaterials where the second polymer matrix is comprised only of polyethylene glycol units joined by gamma-thioether linkages since the starting oligomeric reactants are each functionalized PEGs of similar molecular weight. However, it is not only possible, but potentially desirable to prepare biomaterials using multiple alkylene oxide oligomers with different repeating units or with different molecular weights. For instance, a poly(propylene glycol)-dithiol may be reacted with a poly(ethylene glycol)-diacrylate in the presence of collagen to give a biomaterial of the present technology. Alternatively, a first PEG-dithiol may be reacted with a second PEG-diacrylate, where the second alkylene oxide oligomer (i.e., PEG-diacrylate) has a different molecular weight than that of the first. In another embodiment, the gamma-thioether carbonyl linkages of the joined alkylene oxide oligomers within the biomaterial may be gamma-thioether esters, gamma-thioether amides, gamma-thioether imides, and/or gamma-thioether ketones. In a further embodiment, the second polymer matrix of the biomaterial comprises a compound of formula III, below:

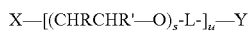

where X is HS— or Y'—(O—CHRCHR')$_s$-L-;

Y is —OC(O)CH=CH$_2$,

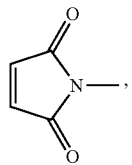

or —(CHRCHR'—O)$_s$—X';

X' is —CHRCHR'—SH;

Y' is —C(O)CH=CH$_2$ or

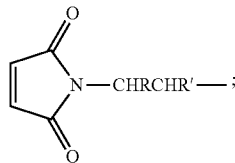

L is a gamma thioether carbonyl linkage

R and R' are independently H or methyl;

s at each occurrence is independently an integer from 5 to 20,000; and u is an integer from 1 to 1000.

In some embodiments, L is —CHRCHR'—S—CH$_2$CH$_2$—C(O)—O— or

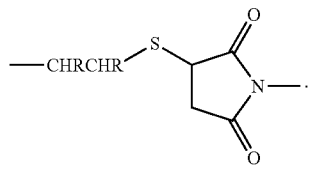

In a further embodiment, gamma-thioether carbonyl linkage in formula III above is —S—CH$_2$CH$_2$—C(O)—O— or the moiety shown in formula IV below.

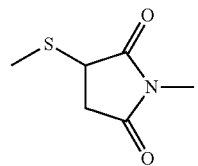

In accordance with another aspect, the present technology provides biomaterials which include at least one biopolymer and a poly(alkylene oxide) that cross-links the biopolymer. In some embodiments, the biomaterials are hydrogels. In certain embodiments, the biopolymer includes amino groups, thiol groups, and bifunctional modifiers connecting at least some of the amino groups to at least some of the thiol groups, and at least one poly(alkylene oxide) cross-linked to at least two thiol groups of the biopolymer. The term "biopolymer" is used herein to refer to polymers comprising amino acids and/or carbohydrates such as those found in or derived from biological systems. For example, biopolymers that may be used in the present biomaterials include but are not limited to gelatin, calcium alginate, calcium/sodium alginate, collagen, oxidized regenerated cellulose, carboxymethylcellulose, amino-modified cellulose, whey protein, chitosan, hyaluronic acid and combinations of any two or more thereof. In some embodiments, the biopolymer comprises gelatin and/or collagen. In certain embodiments, the biopolymer comprises Type A gelatin, Type B gelatin or both.

The biopolymers of the present technology include amino groups, a bifunctional modifier, and thiol groups. For example, each bifunctional modifier may have the formula I:

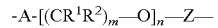

wherein one of A or Z is a divalent moiety covalently bonded to the amino groups of the biopolymer and one of A and Z is a monovalent moiety comprising a thiol group;

wherein the divalent moiety is selected from the group consisting of —O—, —S—, —NH—, C$_{1-24}$-alkyl, C$_{2-24}$-alkenyl, C$_{2-24}$-alkynyl, C$_{1-24}$-alkoxy, C$_{1-24}$-heteroalkyl, C$_{2-24}$-heteroalkenyl, C$_{2-24}$-heteroalkynyl, cyano-C$_{1-24}$-alkyl, C$_{3-10}$-cycloalkyl, C$_{3-10}$-cycloalkenyl, C$_{3-10}$-cycloheteroalkyl, C$_{3-10}$-cycloheteroalkenyl, acyl, acyl-C$_{1-24}$-alkyl, acyl-C$_{1-24}$-alkenyl, acyl-C$_{1-24}$-alkynyl, carboxy, C$_{1-24}$-alkylcarboxy, C$_{1-24}$-alkenylcarboxy, C$_{1-24}$-alkynylcarboxy, carboxy-C$_{1-24}$-alkyl, carboxy-C$_{2-24}$-alkenyl, carboxy-C$_{1-24}$-alkynyl, aryl, aryl-C$_{2-24}$-alkenyl, heteroaryl, heteroaryl-C$_{1-24}$-alkyl, heteroaryl-C$_{1-24}$-alkenyl, heteroaryl-C$_{1-24}$-alkynyl, sulfonate, arylsulfonate, and heteroarylsulfonate;

at each occurrence R$^1$ and R$^2$ is independently selected from the group consisting of H, methyl, and ethyl;

m is an integer from 2 to 8; and n is an integer ranging from 1 to 20,000.

In some embodiments of the biomaterials, one of A and Z is a monovalent moiety selected from the group consisting of thiol, cysteine, homocysteine, cysteamine, cystamine, C$_{1-24}$-alkenylthiol, C$_{2-24}$-alkynylthiol, C$_{1-24}$-heteroalkylthiol, C$_{2-24}$-heteroalkenylthiol, C$_{2-24}$-heteroalkynylthiol, C$_{3-40}$-cycloalkylthiol, C$_{3-10}$-cycloalkenylthiol, C$_{3-10}$-cycloheteroalkylihiol, C$_{3-10}$-cycloheteroalkenylthiol, —C(O)—C$_{1-24}$-alkylthiol, —C(O)—C$_{1-24}$-alkynylthiol, —OC(O)—C$_{1-24}$-alkylthiol, —OC(O)—C$_{1-24}$-alkenylthiol, arylthiol, C$_{1-24}$-alkenyl-arylthiol, C$_{2-24}$-alkynyl-arylthiol, heteroarylthiol, C$_{1-24}$-alkyl-heteroarylthiol, C$_{2-24}$-alkenyl-heteroarylthiol, C$_{1-24}$-alkynyl-heteroarylthiol. Such monovalent moieties may be attached to the amino groups of the biopolymer at any atom with a free valence, other than the sulfur of the thiol group.

As noted above, m is an integer from 2 to 8. In some embodiments in is 2, 3, 4, 5, 6 or 7. In certain embodiments, in is 2, 3, or 4. In some embodiments at each occurrence $R^1$ and $R^2$ is independently H or methyl, while in others $R^1$ and $R^2$ are both H. Thus, for example, the poly(alkylene oxide) portion of formula I may be, but is not limited to, poly(ethylene glycol) or poly(propylene glycol).

In some embodiments, n is an integer from 1 to 2,000, or 1 to 200, or 1 to 100. Examples of n of formula I include but are not limited to 1, 5, 10, 20, 30, 50, 100, 200, 300, 400, 500, 1,000, 2,000, 4,000, 10,000, 15,000, 20,000, and any range between and/or including two or more of these values.

In some embodiments of the biomaterials, the poly(alkylene oxide), the alkylene oxide repeating unit has 2, 3, 4, 5, 6, 7, or 8 carbons. In certain embodiments, the alkylene oxide repeating unit has 2, 3, or 4 carbons. For example, the poly(alkylene oxide) may be selected from the group consisting of polyethylene glycol), poly(propylene glycol), and mixtures thereof.

The biopolymer may be a combination of any of the materials described above. Thus, in some embodiments, the biopolymer includes gelatin, poly(ethylene glycol) and cysteine.

Biomaterials including a biopolymer may be readily prepared as shown in the examples herein. Thus, in one aspect, the present technology provides a method of making biomaterials that includes reacting a poly(alkylene oxide)-diacrylate with at least one biopolymer comprising amino groups, thiol groups, and bifunctional modifiers connecting at least some of the amino groups to at least some of the thiol groups, to provide a biomaterial in which the at least one poly(alkylene oxide) is cross-linked to at least two thiol groups of the biopolymer. The crosslinking of the biopolymer and the poly(alkylene oxide) may be carried out by photopolymerization, e.g., with long wavelength UV, or Michael addition. For example, PEG-diacrylate may be used as the poly(alkylene oxide) and photopolymerized with the biopolymer, gelatin-PEG-cysteine (Gel-PEG-Cys).

The individual polymer matrices as well as the biomaterials or hydrogels can then be characterized using standard physical and morphological characterization techniques known in the art, such as swelling analysis, FITC-dextran release profiles, gelatin dissolution profiles, collagenase effect on hydrogel degradation, etc. Cell culture and adhesion studies with the biomaterials or hydrogels can be conducted using standard methods known in the art, such as two dimensional cell seeding on material surface, three dimensional cell encapsulation into material matrix, cell viability assay, cell proliferation, immunofluorescence staining for morphological characterization, cytokine release quantification as an evaluation of cell function.

The biomaterials of the present technology can be used in any application where biomaterials are currently employed. In this aspect, the biomaterials find use as wound dressing materials, diapers, catamenial devices, drug delivery devices, implants, biosensors, contact lenses, tissue scaffolds, cell transplantation matrices, and the like. In some embodiments, the biomaterial comprises a poly(alkylene oxide) that includes two or more alkylene oxide oligomers joined by gamma-thioether carbonyl linkages. In some embodiments of the present technology, the biomaterial is a hydrogel.

Figure 3:
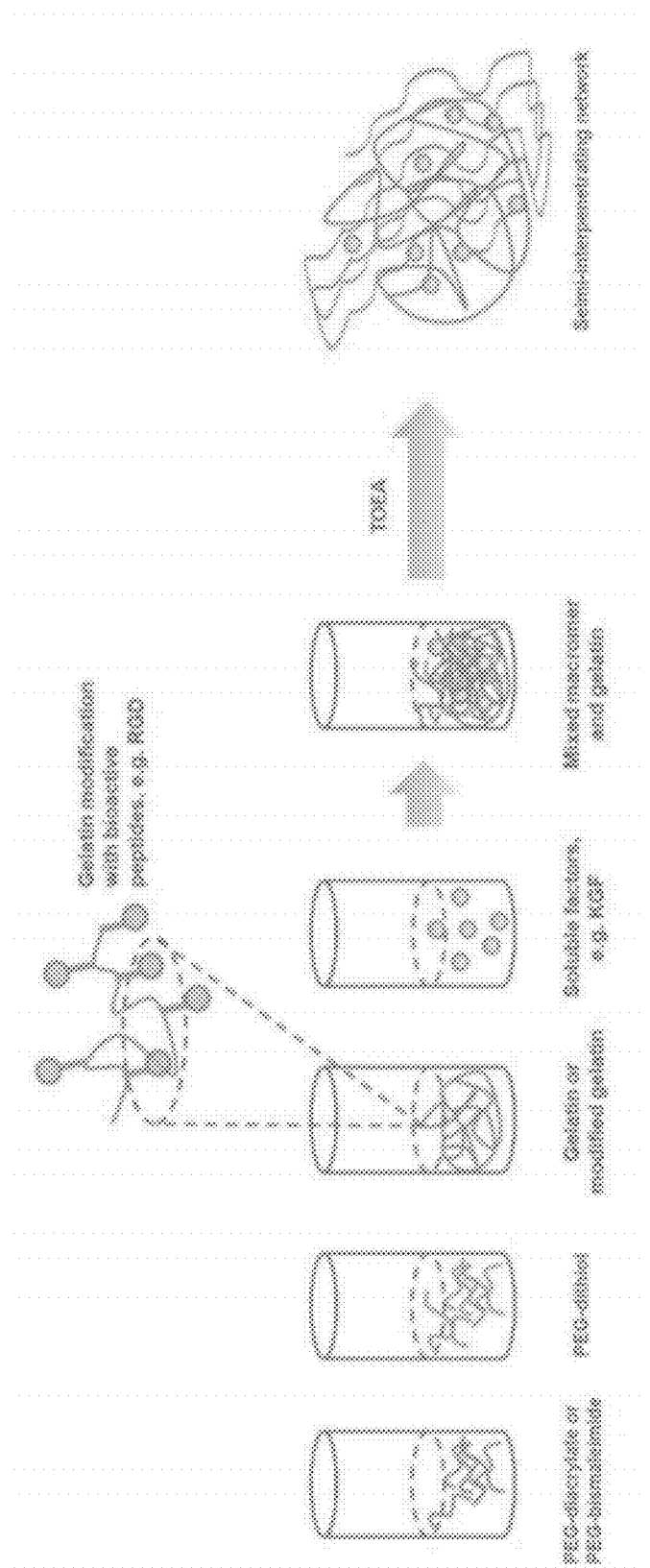
FIG. 3 is an illustration of the procedure for preparation of semi-interpenetrating network (sIPN) biomaterials employing the reaction of PEG-dithiol with either PEG-diacrylate or PEG-dimaleimide in the presence of gelatin. Optionally, soluble factors such as KGF may be added.

All of the biomaterials according to the present technology may further include a pharmacologically active agent within the biomaterial. Such pharmacologically-active agent may be entrained within the biomaterial, or it may be covalently attached to the first polymer matrix. For example, the pharmacologically-active agent KGF may be either covalently conjugated via a bifunctional modifier to the first polymer matrix, or may be incorporated within the first polymer matrix as a free solute (FIG. 3). Likewise, the pharmacologically active agent may be entrained within the cross-linked biopolymer or covalently attached to the biopolymer. In one embodiment, the pharmacologically-active material is covalently attached to the first polymer matrix through one terminus of a bifunctional modifier which is not attached to the first polymer matrix. In another embodiment, the pharmacologically-active material is not covalently attached to the first polymer matrix (or biopolymer). In another embodiment, the Pharmacologically-active material may include vulnerary agents, hemostatic agents, antibiotics, antithelmintics, antifungal agents, hormones, anti-inflammatory agents, proteins, polypeptides, oligonucleotides, cytokines, enzymes, and the like. In a further embodiment, the biomaterials are used to administer a pharmacologically-active agent to a patient in need of the pharmacologically-active agent. In this use, the biomaterial is administered to the patient, as by packing it into a surgical or traumatic wound.

Likewise, the biomaterials according to the present technology may be useful as scaffolds to support living cells. Thus, in one aspect, the biomaterials can be used as biomechanical devices. The biomaterials will support living cells within the bulk of the material, e.g., hydrogel, thereby providing a three-dimensional support network in which the cells can grow and proliferate. Such cells may be entrained within the biomaterial. Biomaterials according to the present technology that contain cells can be implanted into a patient in need of such cells. Thus, in another aspect, the present technology provides a biomaterial in which or on which living cells are supported, e.g., monocytes, fibroblasts, keratinocytes, chondrocytes, myoblasts, endothelial progenitor cells, and stem cells.

The living cells may also be in a diseased state, such as cancer cells. Thus, in this aspect, the present technology provides a biomaterial in which or on which diseased living cells are supported. Such a biomaterial serves as a platform for the study of the cell biology of diseased cells. The biomaterial may include any of the biomaterials described herein, including but not limited to a poly(alkylene oxide) that includes two or more alkylene oxide oligomers joined by gamma-thioether carbonyl linkages. In some embodiments of the present technology, the biomaterial is a hydrogel.

In some embodiments, the biomaterials of the present technology are used as two-dimensional (2D) or three-dimensional (3D) scaffolds to culture or encapsulate living cells. The biomaterials of the present technology provide stable scaffolds with tunable mechanical properties, long-term integrin binding sites and support cell attachment and proliferation in a 2D or 3D environment. In some embodiments, a biomaterial with at least two layers is provided. Each layer may be distinguished either by a different composition of the biomaterial or by containing a different cell type and/or pharmacological agent. For example, in one embodiment the biomaterial includes at least two layers in which fibroblasts are present in one layer and keratinocytes in a second layer. Each layer may be readily optimized to support a specific cell type. Such layered biomaterials may be administered to a subject for repair and/or replacement of damaged or missing skin. In another embodiment, a biomaterial is provided with cells entrained within the biomaterial and the same or different type(s) of cells seeded on an external surface of the biomaterial.

EXAMPLES

The present technology is further illustrated by the following examples, which should not be construed as limiting in any way.

Materials and methods. PEG-dimaleimide (PEG: ~2000 Da) was purchased from Nanocs Inc. PEG-diol (PEG: ~2000 Da), gelatin (type A, bloom 300), triethylamine, triethanolamine (TEOA), p-toluenesulfonyl chloride, lithium aluminum hydride, and sodium hydrosulfide hydrate (NaSH) were obtained from Sigma-Aldrich. Dichloromethane ($CH_2Cl_2$), tetrahydrofuran (THF), toluene, diethyl ether, and anhydrous magnesium sulfate ($MgSO_4$) were provided by Fisher Scientific. PEG-diacrylate was synthesized from PEG-diol (PEG: ~2000 Da, Sigma-Aldrich) following an established procedure. All chemicals were used as received unless otherwise specified. $^1$H NMR spectra were obtained on a Varian 400 MHz instrument. FTIR spectra were recorded on a Bruker Equinox 55 ATR-FTIR spectrometer (single reflection, ZnSe crystal, 20 scans per spectrum) in a N7 atmosphere. Hydrogel samples were dried under vacuum overnight prior to FTIR analysis.

For studies involving modified gelatin-PEG hydrogels: Poly (ethylene glycol) (PEG)-diol (average molecular weight 2,000 Da and 3,400 Da), acryloyl chloride, triethylamine (TEA), N'-disuccinimidyl carbonate (DSC), 4-(dimethylamino) pyridine (DMAP), N,N'-diisopropylethylamine (DIPEA), sodium azide, L-cysteine, gelatin type A (300 bloom, from porcine skin), gelatin type B (75 bloom, from bovine skin), collagenase type I (from *Clostridium histolyticum*) and dimethyformamide (DMF) were purchased from Sigma-Aldrich (ST. Louis, Mo., USA). Irgacure® 2959 was obtained from Ciba Specialty Chemicals (NY; USA). Collagen (Type L front rat tail) was purchased from BD Bioscience (Franklin Lakes, N.J.). Polystyrene beads with carboxyl surface groups (diameter 1.87 μm) and beads without specific surface groups (diameter 1.09 μm) were purchased from Spherotech Inc. (Lake Forest, Ill., USA).

Statistics. Where applicable, data is shown as mean±standard deviation (S.D.) of samples in independent experiments. Cell density data were analyzed by unpaired Student-t test using SigmaStat 2.03. A value of $p<0.05$ was considered statistically significant.

Example 1

Synthesis of PEG-Dithiol

PEG-diol (10.0 g, PEG: ~2000 Da, 5 mM) was dissolved in dry $CH_2Cl_2$ (50 mL). p-Toluenesulfonyl chloride (7.2 g) was dissolved in $CH_2Cl_2$ (20 mL) and added drop-wise to the PEG-diol solution upon stirring. Triethylamine (1.4 mL) was subsequently added to the mixed solution. The reaction was kept at room temperature and stirred overnight. The crude mixture was filtered twice, concentrated via rotary evaporation, and dissolved in toluene (50 mL) and filtered. Filtrates were collected and precipitated in cold diethyl ether while stirring. The precipitates were collected and dried under vacuum. Yield: 9.6 g (96%). $^1$H NMR ($CDCl_3$): δ2.45, s, $CH_3$-aromatic; δ 3.65, in, PEG backbone; δ 7.5, d, 2Hs ortho to sulfonate; δ 7.8, d, 2Hs meta to sulfonate. PEG-ditosylate (5 g, 2.5 mM) in dd$H_2O$ (100 mL) was treated with NaSH hydrate (1.12 g, 20 mM). The reaction was stirred for 5 h at room temperature and then 1 h at 60° C. The crude mixture was neutralized with concentrated $H_2SO_4$, and extracted with $CH_2Cl_2$. The organic layer was collected and dried over anhydrous $MgSO_4$ and precipitated in dry cold diethyl ether. The precipitated product was collected and dried in vacuum overnight (2.8 g, yield 56%). $^1$H NMR ($D_2O$): δ2.68, t, —SH; δ 2.76, —O$CH_2CH_2$SH; δ 2.92, t, —O$CH_2CH_2$SH; δ 3.65, in, PEG backbone. The products obtained from the above reaction were treated with lithium aluminum hydride (1.2 eq) in THF for 1 hr at room temperature under argon protection and then 20 mL of dd$H_2O$ was added to stop the reaction. Reduced PEG-dithiol was extracted with $CH_2Cl_2$, dried with anhydrous $MgSO_4$, and precipitated in cold diethyl ether. The final products were dried in vacuum overnight and stored in argon at −20° C. (2.2 g, 80% yield). Ellman's test was used to determine the level of free sulfhydryl (—SH) groups in the final product, which indicated 20.6±0.5% of free —SH after reduction compared to 6.1±1.2% of free —SH prior to the reduction.

Example 2

Synthesis of PEG-Diacrylate

PEG-diacrylate was synthesized from PEG-diol (PEG: ~2000 Da) following an established procedure. Briefly, PEG-diol was dissolved in dried THF at a ratio of 1 g:5 mL of PEG-diol:THF with heating to facilitate dissolution. Acryloyl chloride and triethylamine were added in a 1:4:6 molar ratio of PEG-diol:acryloyl chloride:triethylamine and the solution was stirred in the dark, at room temperature, for 3 h. The solution was then filtered twice, slowly added drop-wise to a large volume of cold hexanes (100 mL hexanes per 1 g starting PEG-diol) to get precipitate, and filtered again. The precipitate was collected and vacuum dried overnight (90% yield). The resulting PEG-diacrylate product was pale yellow in color. $^1$H NMR ($D_2O$): δ5.9d, 6.4d, 2Hs, $CH_2$=CH—; δ 6.1, t, 1H, $CH_2$—CH—; δ3.65, m, PEG backbone.

Example 3

Synthesis of PEG Hydrogels and sIPN Biomaterials

General. PEG hydrogels were prepared according to the synthetic scheme in shown in FIG. 1, employing either thiol-ene or thiol-maleimide addition reactions of PEG-dithiol with either PEG-diacrylate or PEG-dimaleimide. The procedure for preparation of thiol-ene and thiol-maleimide derived PEG hydrogels is further illustrated in FIG. 2. FIG. 3 illustrates the procedure for the preparation of semi-interpenetrating network biomaterials, employing the reaction of PEG-dithiol with either PEG-diacrylate or PEG-dimaleimide in the presence of gelatin.

A1. PEG Hydrogels Via Thiol-Ene Reaction of PEG-Dithiol and PEG-Diacrylate

Figure 2:
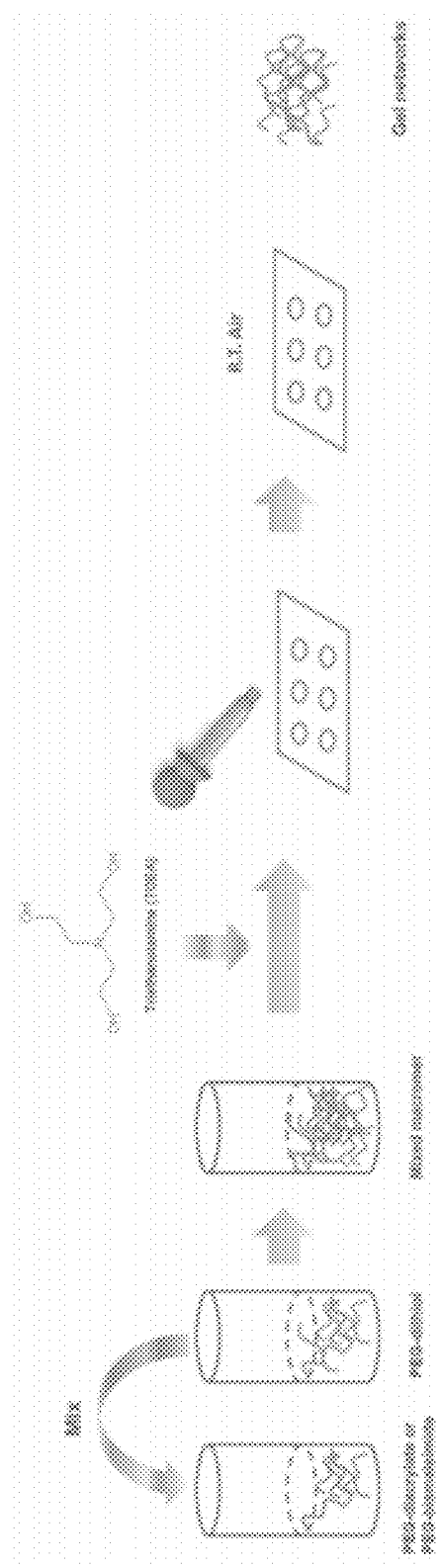
FIG. 2 is an illustration of the procedure for the preparation of thiol-ene or thiol-maleimide PEG biomaterials.

As shown indicated in Table 1, thiol-ene PEG hydrogels in varying weight percentages were prepared at pH 7.5 from aqueous solutions of PEG-diacrylate and PEG-dithiol. The total percent polymer by weight was varied by employing different concentrations of the PEG-diacrylate and PEG-dithiol macromers in PBS. As illustrated in FIG. 2, PEG-diacrylate and PEG-dithiol were separately dissolved in aqueous buffered saline in vials. The PEG-dithiol solution was transferred to the PEG-diacrylate solution, and the macromers were mixed via vortexing. Addition of triethanolamine (0.3 M) to the mixed macromer solution resulted in the formation of a thiol-ene PEG hydrogel which was cured at room temperature in air.

As further shown in Table 1, thiol-ene PEG hydrogels were similarly prepared from PEG-diacrylate and PEG-dithiol at varying pH.

In all cases, the addition of aqueous solutions of PEG-dithiol to PEG-diacrylate resulted in the rapid formation of PEG hydrogels, with gelation times (as measured by the vial inversion method to observe the time when the contents stopped flowing) ranging from seconds (Table 1, Entries 1 and 2) to minutes (Entry 3). The total polymer weight percentage showed a significant effect on gelation, with increasing polymer weight percentages leading to decreasing gelation times. The effect of pH on gelation time at a constant polymer weight percent (17%) was less significant within the pH ranges tested.

TABLE 1

Thiol-ene PEG hydrogels prepared by reaction of PEG-dithiol (PEG: ~2 kDa) with PEG-diacrylate (PEG: ~2 kDa) at varying (a) macromer concentrations and (b) pH.

a) Varying macromer concentrations

| Entry | PEG-dithiol (g) | PEG-diacrylate (g) | 1x PBS (mL) | 0.3M TEOA (mL) | Total polymer % (w/w) | Gelation Time |
|---|---|---|---|---|---|---|
| 1 | 0.05 | 0.032 | 0.1 | 0.1, pH 7.5 | 29 | 30 s |
| 2 | 0.05 | 0.032 | 0.2 | 0.2, pH 7.5 | 17 | 120 s |
| 3 | 0.05 | 0.032 | 0.3 | 0.3, pH 7.5 | 12 | >30 min* | b) Varying pH

| Entry | PEG-dithiol (g) | PEG-diacrylate (g) | 1x PBS (mL) | 0.3M TEOA (mL) | Gelation Time |
|---|---|---|---|---|---|
| 1 | 0.05 | 0.032 | 0.2 | 0.2, pH 7.5 | 120 s |
| 2 | 0.05 | 0.032 | 0.2 | 0.2, pH 8.0 | 120 s |
| 3 | 0.05 | 0.032 | 0.2 | 0.2, pH 10 | 90 s |

*Formulation from Entry 3 is in gel form, but remains flowing after 1 h.

A2. sIPN Biomaterials Via Thiol-Ene Reaction of PEG-Dithiol and PEG-Diacrylate in the Presence of Gelatin Thiol-ene sIPN biomaterials were prepared by through simple modification of the procedure described in Example 3A1. As further shown in FIG. 3., the PEG-dithiol, PEG-diacrylate, and gelatin were separately dissolved in phosphate buffered saline. The solutions were placed in a water bath at 37° C. prior to mixing. The gelatin solution was first mixed quickly with the PEG-dithiol solution and the resultant combined solution was subsequently mixed with the PEG-diacrylate solution via vortexing. The well-mixed prepolymer solution (i.e., the solution of the mixed macromers and gelatin) was kept at 37° C. TEOA was added to prepolymer and curing was allowed to proceed at 37° C. in air. As shown in Table 2, several thiol-ene sIPN biomaterials were prepared in separate experiments by using gelatin solutions of varying concentrations. After reaction with TEOA, each of the three formulations indicated gave thiol-ene sIPN biomaterials as flowing gels (to varying degrees) after 2 hours at 37° C.

TABLE 2

Thiol-ene sIPN biomaterials prepared by reaction of PEG-dithiol (PEG: ~2 kDa) with PEG-diacrylate (PEG: ~2 kDa) in the presence of gelatin.*

| Entry | PEG-dithiol (g) | PEG-diacrylate (g) | Gelatin solution (w/v) (mL) | 1x PBS (mL) | pH 7.5 TEOA (mL) | Total polymer % (w/w) | Gelation Time |
|---|---|---|---|---|---|---|---|
| 1 | 0.05 | 0.032 | 30%, 0.2 | 0.2 | 0.2 | 19 | ~2 h[a] |
| 2 | 0.05 | 0.032 | 15%, 0.2 | 0.2 | 0.2 | 16 | —[b] |
| 3 | 0.05 | 0.032 | 10%, 0.2 | 0.2 | 0.2 | 14 | —[b] |

*Curing temperature: 37° C.

[a] slightly flowing

[b] failed to achieve complete gelation

B1. PEG Hydrogels Via Thiol-Maleimide Reaction of PEG-Dithiol and PEG-Dimaleimide As shown indicated in Table 3, thiol-maleimide PEG hydrogels according to the synthetic scheme indicated in FIG. 1 were prepared in varying weight percentages at constant pH from aqueous solutions of PEG-dithiol and PEG-dimaleimide. The total percent polymer by weight was varied by employing different concentrations of the PEG-dithiol and PEG-dimaleimide macromers in PBS. As illustrated in FIG. 2, PEG-dithiol and PEG-dimaleimide were separately dissolved in aqueous buffered saline in vials. The PEG-dithiol solution was transferred to the PEG-dimaleimide solution, and the macromers were mixed via vortexing (~30 sec). Addition of triethanolamine (0.3 M) to the mixed macromer solution resulted in the formation of a thiol-maleimide PEG hydrogel which was cured at room temperature in air-tight molds (or vials). Gelation time, determined by visual inspection, ranged from minutes to days (Table 3). Increasing the macromer concentration led to a significant decrease in the gelation time. Among the various conditions tested, the PEG hydrogel showed the shortest gelation time at a total polymer concentration of 31% (w/w) in pH 7.5 phosphate buffer saline with 0.3 M TEOA.

As further shown in Table 3, thiol-maleimide PEG hydrogels were similarly prepared from PEG-dithiol and PEG-maleimide at varying pH (pH 6.5, pH 7.5, and pH, 8.0). The results indicate that the PEG hydrogel was significantly affected by pH values, with more rapid gel formation observed under basic conditions.

TABLE 3

Thiol-maleimide PEG hydrogels prepared by reaction of PEG-dithiol (PEG: ~2 kDa) with PEG-dimaleimide (PEG: ~2 kDa) at varying macromer concentrations and pH.

a) Varying macromer concentrations

| Entry | PEG-dithiol (g) | PEG-dimaleimide (g) | pH 7.5 PBS w/ 0.3M TEOA | pH 7.4 PBS (μl) | Total polymer % (w/w) | Gelation time |
|---|---|---|---|---|---|---|
| 1 | 0.05 | 0.042 | 100 | 100 | 31 | ~40 min |
| 2 | 0.05 | 0.042 | 200 | 200 | 18 | ~90 min |
| 3 | 0.05 | 0.042 | 300 | 300 | 13 | >20 h | b) Varying pH

| Entry | PEG-dithiol (g) | PEG-dimaleimide (g) | PBS w/ 0.3M TEOA (mL) | Gelation time |
|---|---|---|---|---|
| 1 | 0.05 | 0.042 | 0.4, pH 6.5 | >24 h |
| 2 | 0.05 | 0.042 | 0.4, pH 7.5 | ~90 min |
| 3 | 0.05 | 0.042 | 0.4, pH 8.0 | ~90 min |

B2. sIPN Biomaterials Via Thiol-Maleimide Reaction of PEG-Dithiol and PEG-Dimaleimide in the Presence of Gelatin The procedure for preparation of thiol-maleimide sIPN biomaterials was analogous to that described in Example 3A1, except that PEG-dimaleimide was used rather than PEG-diacrylate (see FIG. 3). The results in Table 4 indicate that complete gelation was observed after 24 h curation at 37° C. with formula #2 and #3.

TABLE 4

Thiol-maleimide sIPN biomaterials prepared by reaction of PEG-dithiol (PEG: ~2 kDa) with PEG-dimaleimide (PEG: ~2 kDa) in the presence of gelatin.

| # | PEG-dithiol (g) | PEG-dimaleimide (g) | Gelatin solution (w/v) (mL) | 1x PBS (mL) | pH 7.5 TEOA (mL) | Total polymer % (w/w) | Gelation Time |
|---|---|---|---|---|---|---|---|
| 1 | 0.05 | 0.042 | 10%, 0.2 | 0.2 | 0.2 | 15.7 | —* |
| 2 | 0.05 | 0.042 | 15%, 0.2 | 0.2 | 0.2 | 17 | ~1 d |
| 3 | 0.05 | 0.042 | 30%, 0.2 | 0.2 | 0.2 | 20 | ~1 d |

*Formulation from Entry 1 showed slight fluidity after 3 days of curation.

Example 4

Fourier Transform Infrared Spectroscopy (FTIR) of PEG Hydrogels

Figure 4:
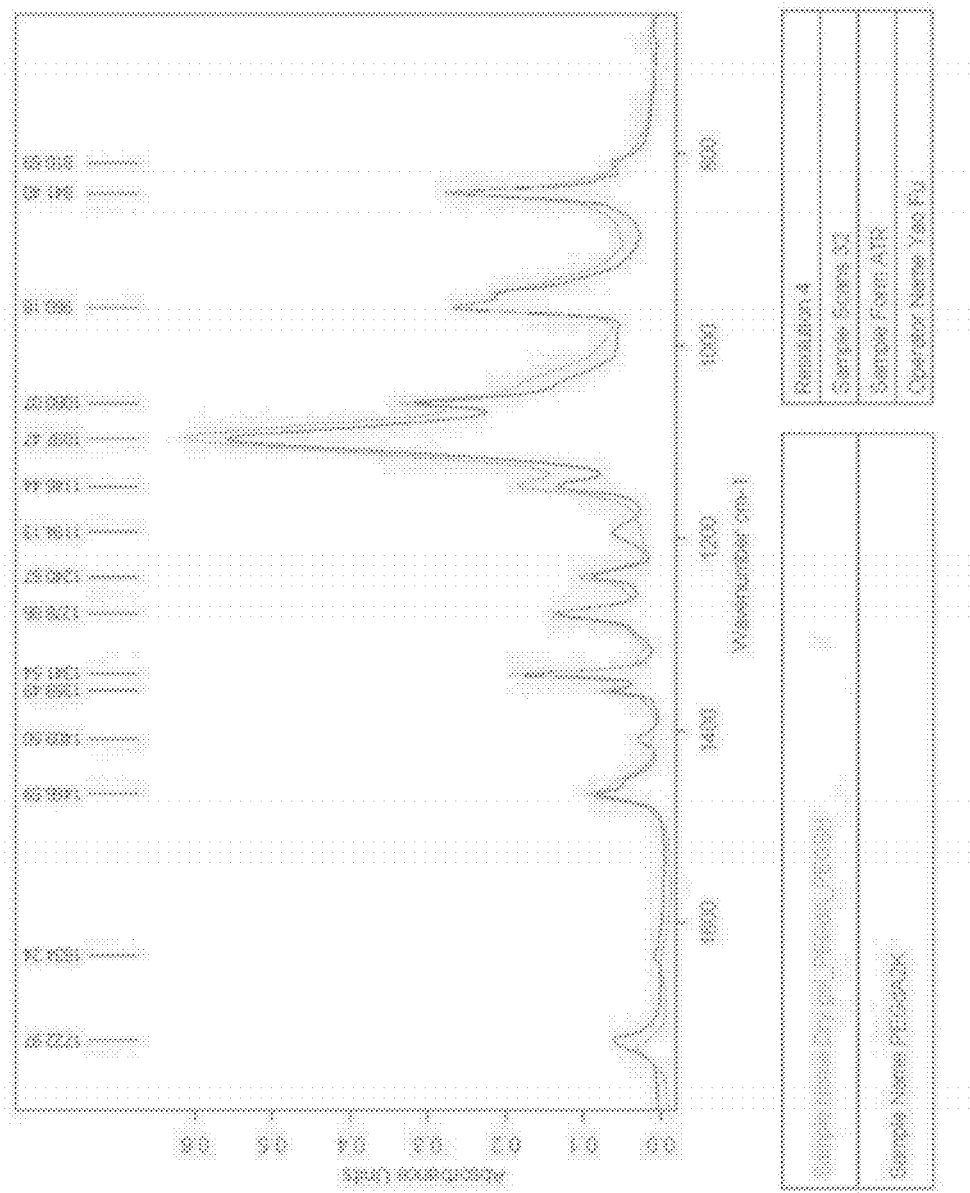
FIG. 4 is an FTIR spectrum of a thiol-ene PEG hydrogel after curing, in comparison to PEG-diacrylate starting material.
Figure 5:
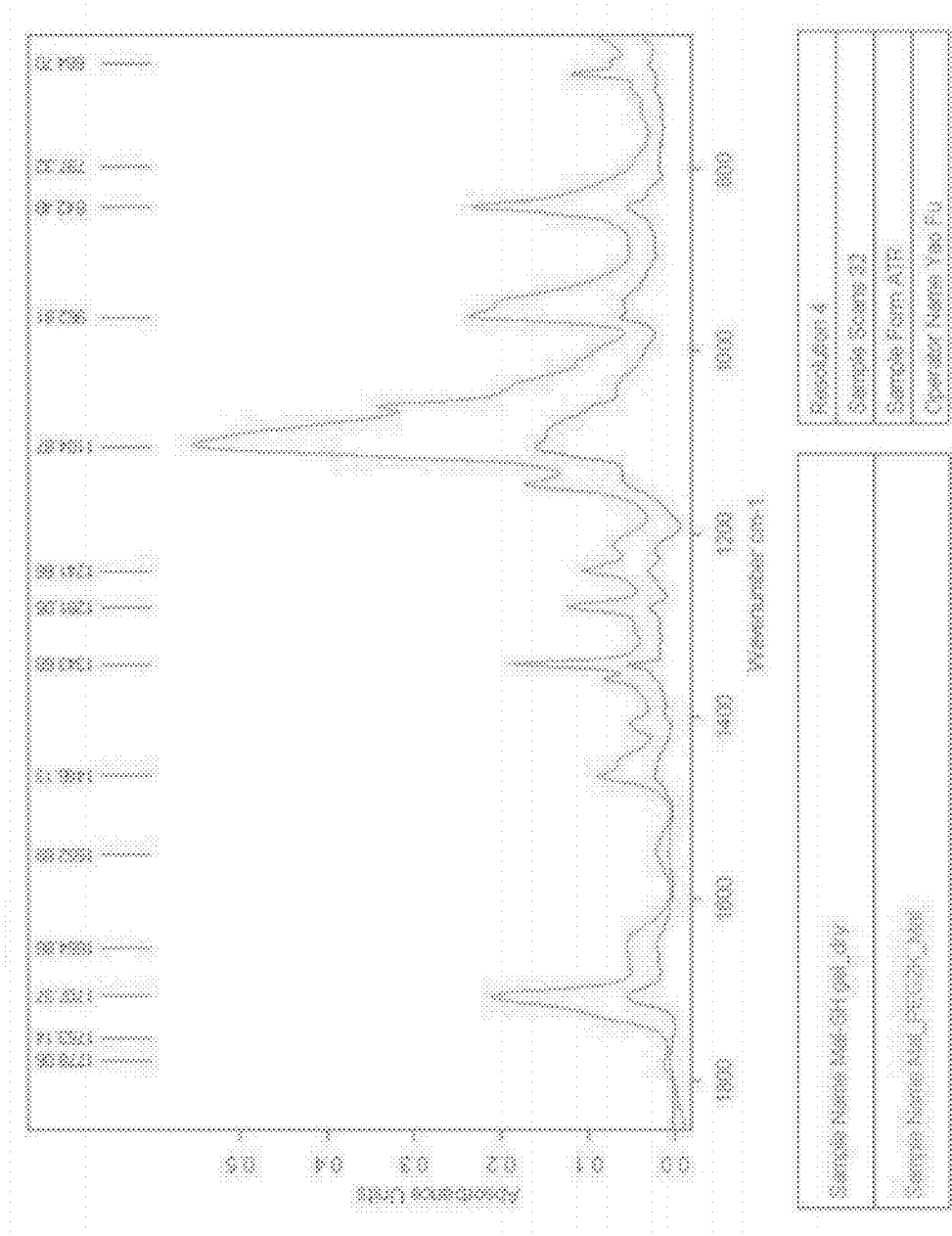
FIG. 5 is an FTIR spectrum of a thiol-maleimide PEG hydrogel after curing, in comparison to PEG-dimaleimide starting material.

FTIR proved to be a convenient technique for monitoring the progress of the reaction of PEG-dithiol with PEG-diacrylate or PEG-dimaleimide to form their respective thiol-diacrylate or thiol-dimaleimide PEG hydrogels. As shown in FIG. 4, the characteristic absorption bands at 810 cm$^{-1}$ (v, =C—H acrylate) for PEG-diacrylate disappeared after complete gel formation. In a similar fashion, the characteristic absorption band at 695 cm$^{-1}$ (v, =C—H in maleimide) for PEG-dimaleimide also disappeared after gel formation (FIG. 5).

Figure 6:
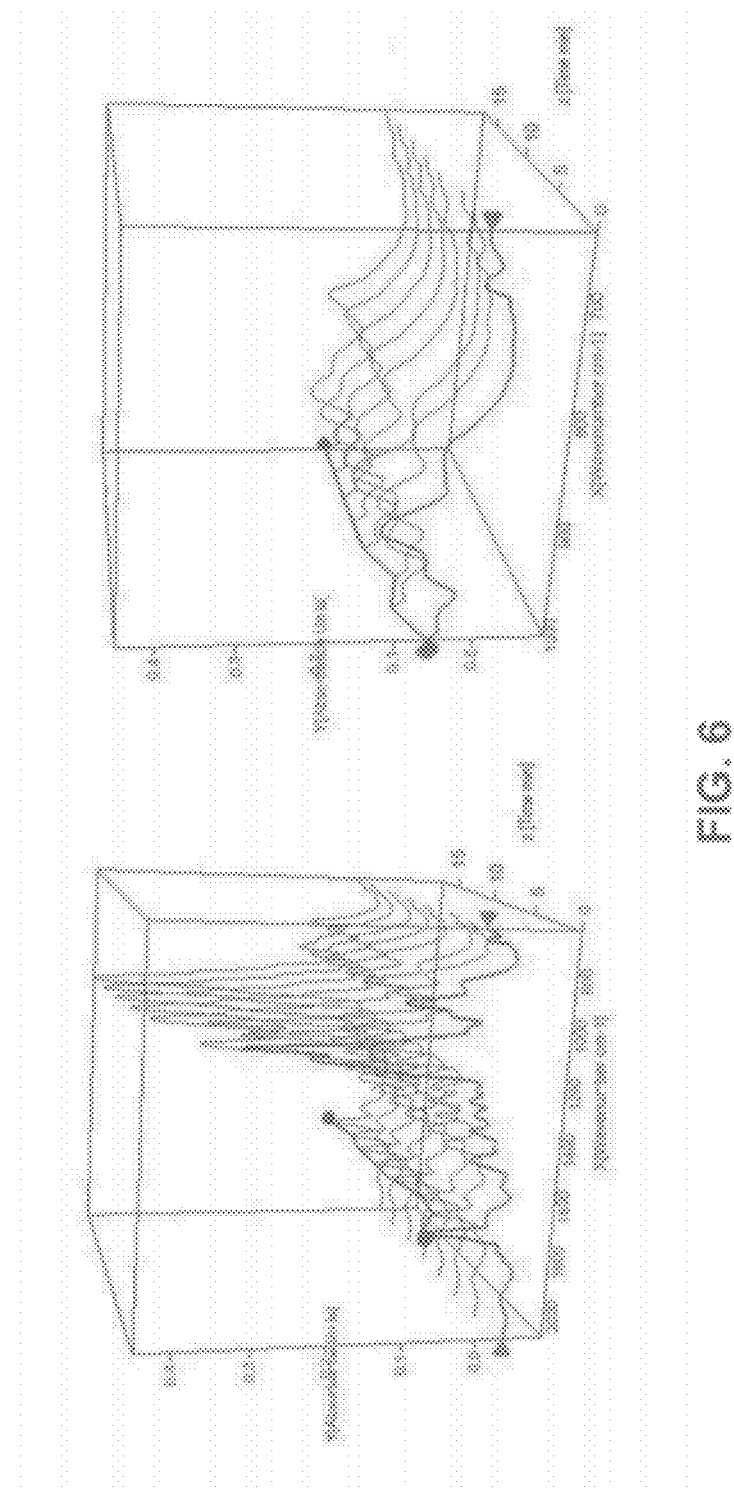
FIG. 6 is stacked FTIR spectra showing the reaction of PEG-dithiol with PEG-dimaleimide in THF to form a thiol-maleimide PEG hydrogel as a function of time.
Figure 7:
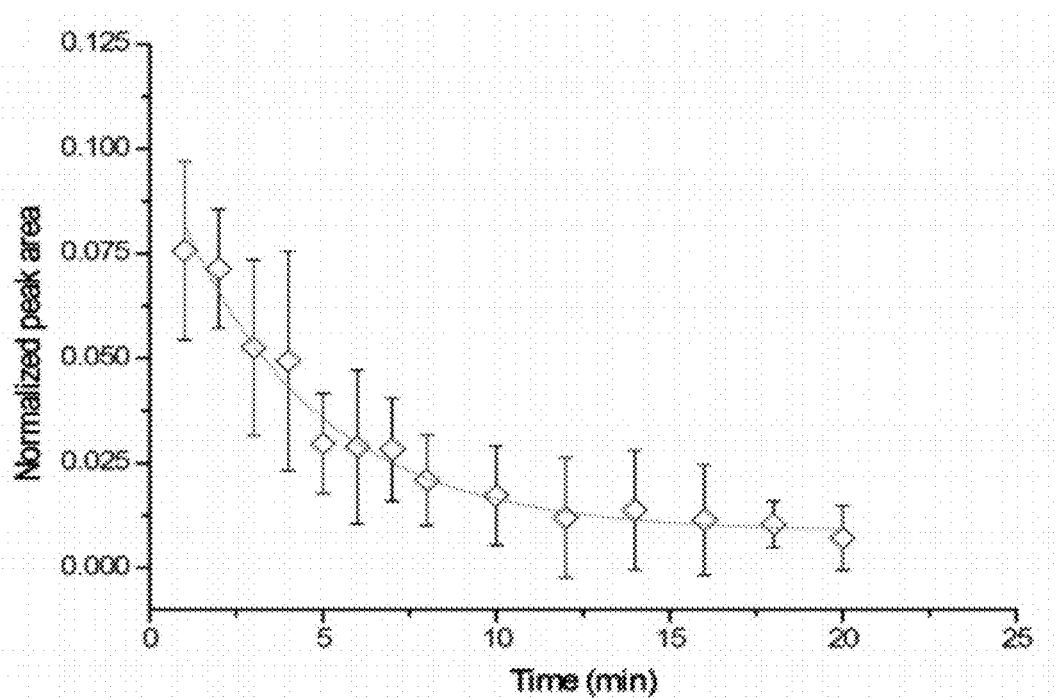
FIG. 7 is a graph illustrating the reaction kinetics of the reaction of PEG-dithiol with PEG-dimaleimide via normalized peak integration at 695 cm$^{-1}$ using absorption peak at 1707 cm$^{-1}$ as an internal reference. Data is presented as mean±S.D., n=3.
Figure 8:
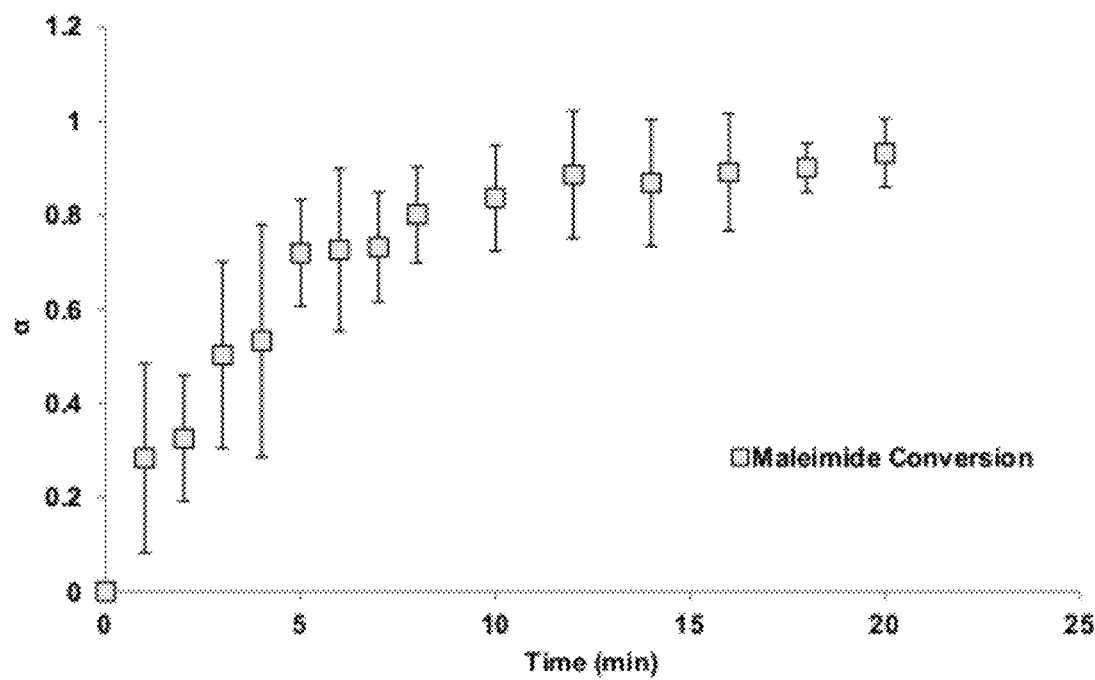
FIG. 8 is a graph illustrating PEG-dimaleimide conversion during the curing of a thiol-maleimide PEG hydrogel in THF as a function of time in either PBS or PBS with TEOA. Data is presented as mean±S.D., n=3.

As shown in FIG. 6, a more detailed kinetics study was performed by obtaining multiple FTIR spectra for the reaction of PEG-dithiol with PEG-dimaleimide in THF during the cure period (20 min). A decrease in the IR absorption peak at 695 cm$^{-1}$ (attributed to the =C—H bending vibration of maleimide group) was observed over time. By using the C=O stretch (1724 cm$^{-1}$) of the maleimide group as an internal reference, the conversion of maleimide C=C bonds (=C—H bend, 695 cm$^{-1}$) as a function of time can be calculated (FIG. 7 and FIG. 8). Specifically, integration of absorption peak areas at 695 cm$^{-1}$ and 1724 cm$^{-1}$ (OPUS version 4.2 software provided with the spectrometer), allows for the calculation of the degree of maleimide groups that have reacted at a certain time. A. Thus, the conversion of unsaturated maleimide groups, α, has been calculated by the following equation:

$$\alpha = 1 - \left( \frac{(A_{695\,cm^{-1}}/A_{1724\,cm^{-1}})_t}{(A_{695\,cm^{-1}}/A_{1724\,cm^{-1}})_{t=0}} \right)$$

where $A_t$ is the area of the vibration band at tune t.

FIG. 7 and FIG. 8, show the conversion profile of the maleimide C=C bond as a function time. The conversion reached steady state around 10 min, indicating a near complete conversion of the C=C group.

Example 5

Swelling and Degradation Studies of PEG Hydrogel and sIPN Biomaterial Samples The PEG hydrogel and sIPN biomaterial samples previously synthesized were dried under vacuum overnight. The dried PEG hydrogel and sIPN biomaterial samples were accurately weighed prior to the swelling study. A sample disk of either the PEG hydrogel or the sIPN biomaterial was immersed in PBS (10 mL of pH 7.4) in a Petri dish at 37° C. At predetermined time points, the sample was carefully removed from the Petri dish and blotted with Kim-wipes® to remove the excess water on the sample surfaces and weighed. Equilibrium weight swelling ratio ($Q_s$) was defined as follows:

$$Q_s = \frac{(w_t - w_d)}{w_d}$$

where $w_t$ is the gel weight at the time t, and $w_d$ is the dried gel weight.

Figure 9:
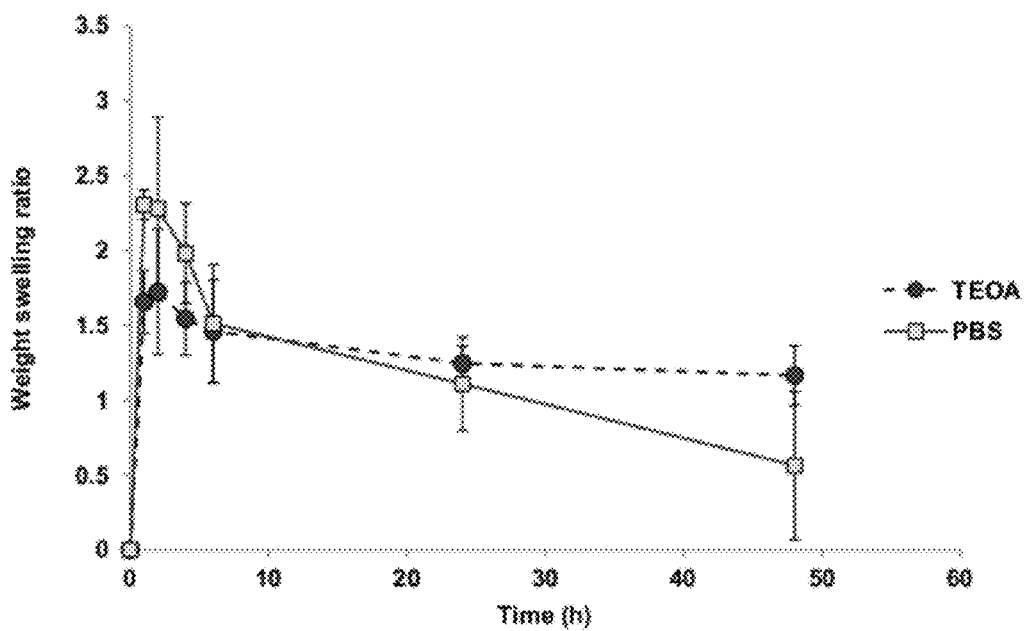
FIG. 9 is a graph illustrating the average weight swelling ratio of a thiol-ene PEG hydrogel (total polymer wt % during gel formation: ~17% w/w) as a function of time. Data is presented as mean±S.D., n=3.
Figure 10:
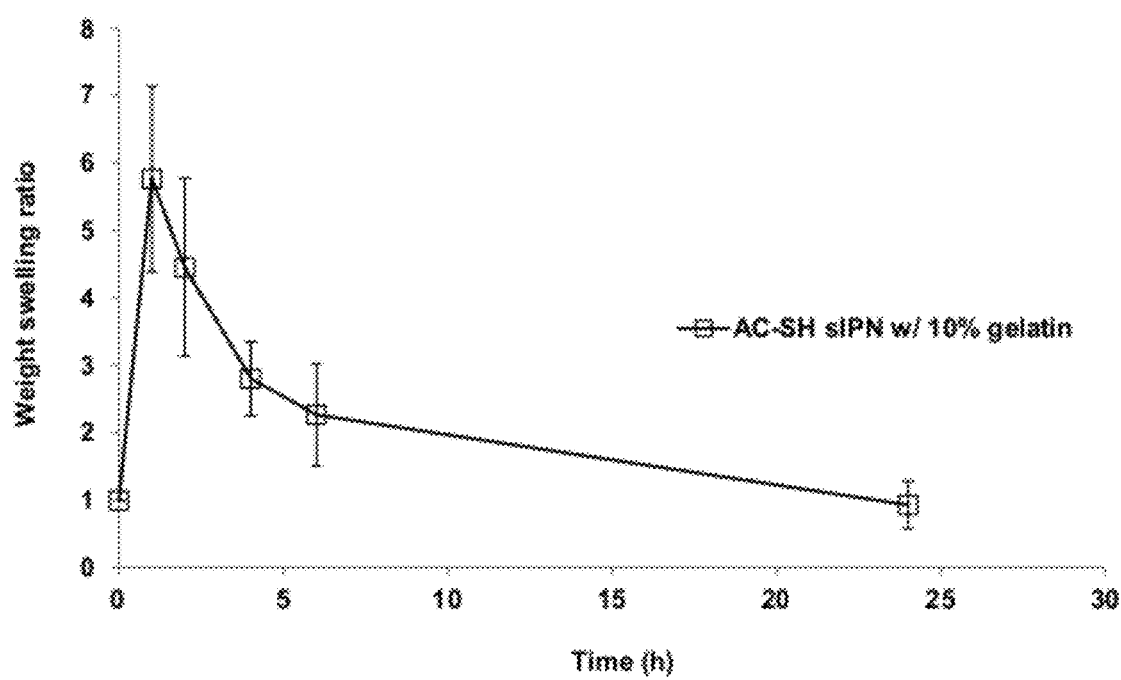
FIG. 10 is a graph illustrating the average weight swelling ratio of a thiol-ene sIPN hydrogel (total polymer wt % during gel formation, ~19% w/w) as a function over time. Data presented as mean±S.D., n=3.

As shown in FIG. 9, thiol-ene PEG hydrogels reached a maximum weight swelling ratio within an hour, but gradual mass loss was observed after reaching maximum swelling. No significant difference was observed in the swelling and degradation behavior of the thiol-ene PEG hydrogels between PBS buffer and PBS buffer containing TEOA. The sIPN biomaterial prepared via thiol-ene addition (employing 10% gelatin w/v) displayed similar swelling and degradation pattern compared to PEG hydrogel via thiol-ene addition, i.e., rapid swelling within an hour following by gradual degradation (FIG. 10).

Figure 11:
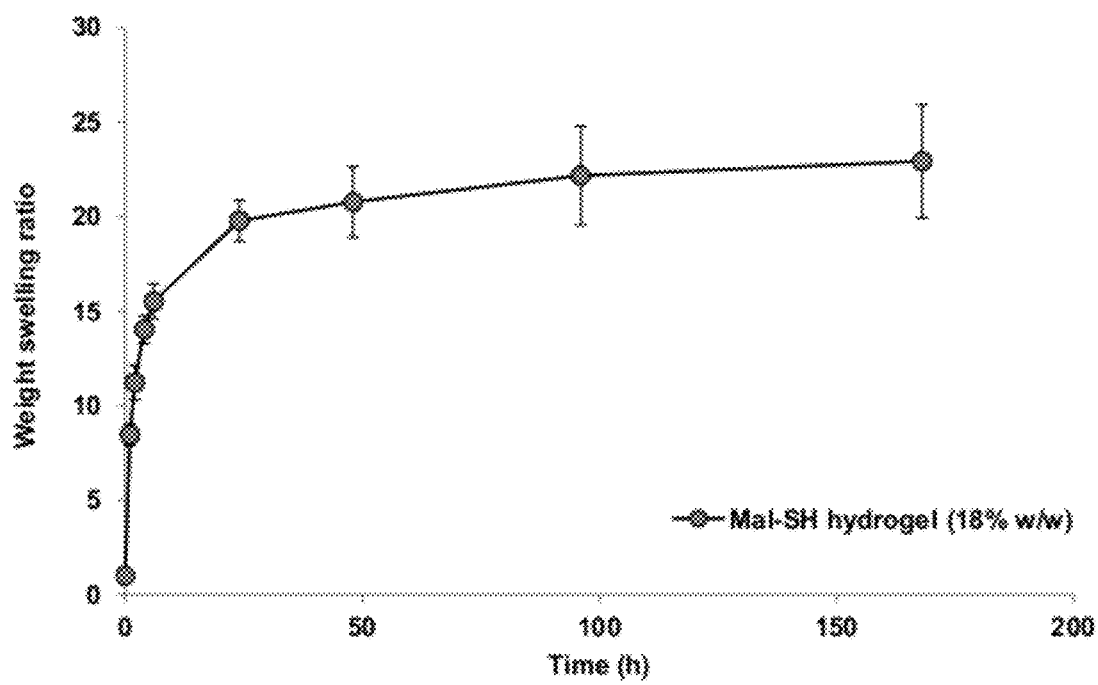
FIG. 11 is a graph illustrating the average weight swelling ratio of a thiol-maleimide PEG hydrogel (synthesized with 0.3 M TEOA at pH 7.5; total polymer wt % during gel formation: ~18% w/w) as a function of tune. Data is presented as mean±S.D., n=3.
Figure 12:
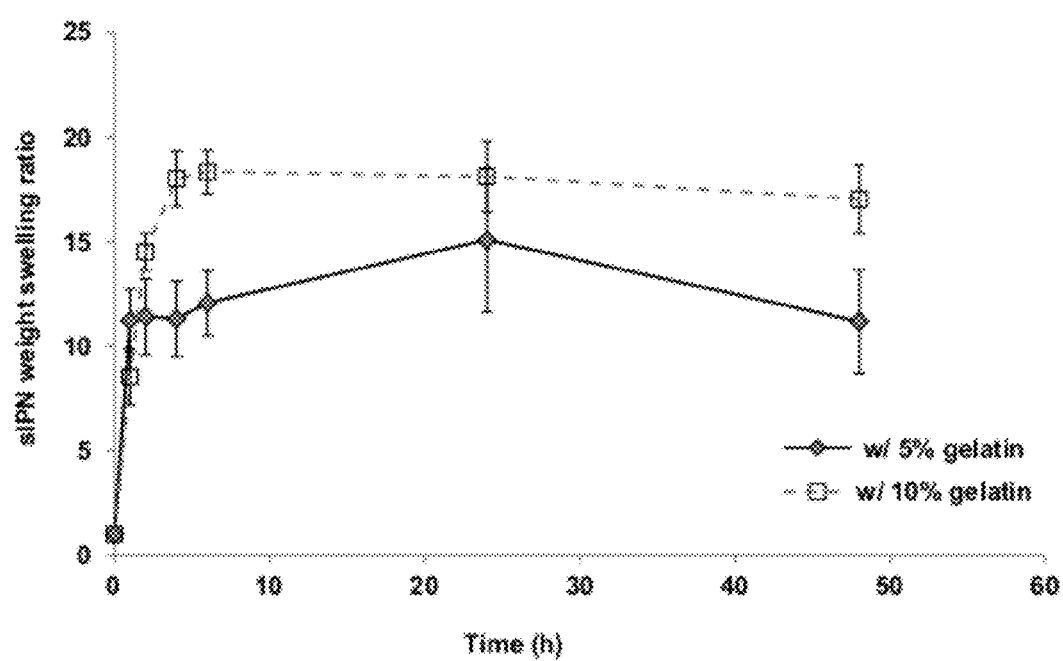
FIG. 12 is a graph illustrating the average weight swelling ratio of two thiol-maleimide sIPN hydrogels as function of time. Total polymer wt % during gel formation: 17% w/w for the sIPN hydrogel with 5% gelatin and 20% w/w for the sIPN hydrogel with 10% gelatin. Data presented as mean±S.D., n=3.

Thiol-maleimide PEG hydrogels displayed consistent and increasing swelling through 7 days (168 h), with a maximum average swelling weight ratio of (23±3) (FIG. 11) and no significant mass loss was observed during 7-day period, indicating the relative robustness of the PEG hydrogel structure. The weight swelling ratio reached a steady state around 48 h, which indicated an equilibrium swelling state of the PEG hydrogel. The thiol-maleimide sIPN biomaterial with 10% gelatin showed a maximum average swelling weight ratio of (18±1) around 4 h (FIG. 12), while sIPN biomaterial with 5% gelatin reached maximum average swelling weight ratio of (15±3.4) in about 24 h (FIG. 12). sIPN samples in both formulation groups started to degrade after 24 h and the gels fell apart completely after 48 h. Therefore, the thiol-maleimide sIPN biomaterial structures were less stable than their PEG hydrogel counterparts. However, the swelling and degradation study was conducted in an excess amount of buffer solution, while different swelling and degradation profiles are expected when applied as a wound dressing material in a physiological wound environment.

Example 6

Surface Hydrophilicity

The surface hydrophilicity of thiol-ene and thiol-dimaleimide PEG hydrogels, their sIPN biomaterial counterparts, as well as sIPN prepared via photopolymerization, were quantified with a modified, computerized, underwater air-captured surface contact angle system (VCA2500; AST products, Inc. Billerica, Mass.). Fully swollen samples were secured to a glass slide with cyanoacrylate glue and placed in a water chamber. Air bubbles were placed on the exposed and submerged surface of the sample via syringe. Two angles per bubble were measured. The study was conducted in triplicates.

With respect to the underwater air-captured surface contact angle analysis, a larger surface contact angle signifies higher surface hydrophilicity of the material. PEG hydrogels and sIPN biomaterials prepared via thiol-ene addition showed contact angle values similar to photopolymerized sIPN (cf. Table 5 and Table 7), indicating similar surface hydrophilicity of the material. In contrast, PEG hydrogels and sIPN biomaterials prepared via thiol-maleimide addition showed higher contact angle values, probably due to the increasing hydrophilicity of the material surfaces (Table 6).

TABLE 5

Contact angles of thiol-ene PEG hydrogels and sIPN biomaterials.

| Samples | Contact angle (left) | Contact angle (right) | Average ± S.D. |
|---|---|---|---|
| sIPN biomatehal (12%, w/w) | 136.0<br>139.3<br>136.7 | 136.0<br>139.6<br>138.4 | 137.6 ± 1.6 |
| Hydrogel (29%, w/w) | 127.3<br>133.4<br>132.4 | 130.5<br>134.8<br>135.9 | 132.4 ± 3.1 |
| Hydrogel (17%, w/w) | 143.9<br>140.3<br>136.0 | 142.9<br>140.3<br>136.4 | 140.0 ± 3.2 |

TABLE 6

Contact angles of thiol-maleimide PEG hydrogels and sIPN biomaterials.

| Samples | Contact angle (left) | Contact angle (right) | Average ± S.D. |
|---|---|---|---|
| Hydrogel (18%, w/w) | 154.2<br>152.3<br>150.4 | 154.3<br>152.5<br>149.2 | 152.1 ± 2.0 |
| sIPN biomaterial (17%, w/w) | 154.6<br>162.6<br>160.9 | 156.1<br>163.1<br>160.6 | 159.6 ± 3.5 |

TABLE 7

Contact angles of photopolymerized sIPN (via photopolymerization of PEG-diacrylate).*

| sIPN formulation | Contact angle | Total polymer w/w % |
|---|---|---|
| 4G6P2K | 141 ± 0.8 | 50 |
| 6G4P2K | 135.9 ± 1.0 | 50 |

*sIPN were prepared via photopolymerization. Reference: Burmania J A, Martinez-Diaz G J, Kao W J. Synthesis and physicochemical analysis of interpenetrating networks containing modified gelatin and poly(ethylene glycol) diacrylate. J Biomed Mater Res A. 2003, 67(1), 224-34.

Example 7

Cell Culture and Adhesion

General. PEG hydrogels prepared from thiol-maleimide addition were tested (total polymer wt % during preparation=18% w/w).

A. Monocytes

Monocytes were isolated following an established procedure. Briefly, 60 mL citrate whole blood was collected from a fasted, unmedicated, healthy volunteer. The whole blood was diluted in DPBSE (DPBS, 1 mmol/L EDTA; Ca/Mg-free), spun in an underlayered Ficoll-Paque Premium density gradient, and the buffy coat was collected. The buffy coat was resuspended in DPBSE and pelleted with centrifugation. Following two pellet and resuspension steps, the mononuclear cells were diluted in complete medium (CM: IMDM+ $NaHCO_3$, L-glutamine, 25 mM HEPES, without phenol red) to a cell concentration of $1-2\times10^6$ cells/mL and this suspension was slowly underlayered with 25 mL 46% iso-osmotic Percoll (46 mL (9.25 mL Percoll:0.75 mL 10×DPBS)+54 mL CM with phenol red) using an 18 gauge spinal needle. The resulting solution was centrifuged and a band of monocytes was collected from the interface of the CM with phenol red and the CM without phenol red. The monocytes were washed with cold DPBSE, pelleted, and washed once more in cold RPMI 1640 for a final pellet/resuspension cycle. The final pellet was resuspended in 2 mL cold RPMI 1640 and the cell concentration was calculated using a hemocytometer. Typically $12-20\times10^6$ monocytes were isolated from 60 mL whole blood. Cells were statically seeded on four thiol-maleimide PEG hydrogel films directly cast into the 48-well plate, four photopolymerized PEG hydrogel films, and four tissue culture polystyrene (TCPS, Becton Dickinson Labware, N.J.) wells at a concentration of $10^6$ cells/mL, suspended in RPMI 1640 media with 10% autologous serum. Cell cultures were maintained at 37° C. and 5% $CO_2$.

B. Fibroblasts

Neonatal human dermal fibroblasts were obtained from Lonza and cultured in fibroblast growth medium-2 (FGM-2, Lonza) containing FBM, 0.1% insulin, 0.1% recombinant human fibroblast growth factor-B, 0.1% GA-1000, and 2% fetal bovine serum (FBS). Fibroblasts for adhesion study were derived from the same cell stock at passage 5 and were harvested and split into each experimental group at about 90% confluence. As in 7A above, cells were seeded on thiol-maleimide PEG hydrogel, photopolymerized PEG hydrogel, and TCPS surfaces at a seeding density of $4\times10^4$ cells/mL.

C. Keratinocytes

Normal human epidermal keratinocytes from neonatal foreskin (NHEK; Lonza, Allendale, N.J., USA) were cultured in keratinocyte growth medium (KGM; Lonza) supplemented with 5% fetal bovine serum (FBS; Atlantic Biologics, Miami, Fla., USA). Similarly, cells were seeded onto four thiol-maleimide PEG hydrogel, four photopolymerized PEG hydrogel and four TCPS surfaces within 48-well plates at a concentration of $4\times10^4$ cells/mL, and maintained at 37° C. and 5% $CO_2$, in 0.5 mL of KGM supplemented with 5% FBS. TCPS was employed as a positive surface control, while photopolymerized PEG hydrogel was used as an additional surface comparison.

D. Cell Adhesion

At 2, 24, and 96 h, all samples were washed twice with culture medium to remove non-adherent cells, and resupplied with fresh culture medium and allowed to incubate further. Adherent cells on all surfaces were imaged using a computer-assisted video analysis system (Metamorph v4.1) coupled to an inverted microscope (Nikon, Eclipse TE300). The adherent cells were quantified and expressed as number of cells/ $mm^2$ surface area. Five images per sample were taken at random fields of view. Adherent cell density was determined per $mm^2$ after normalization to the microscope view field using the image analysis software ImageJ (NIH).

Figure 13:
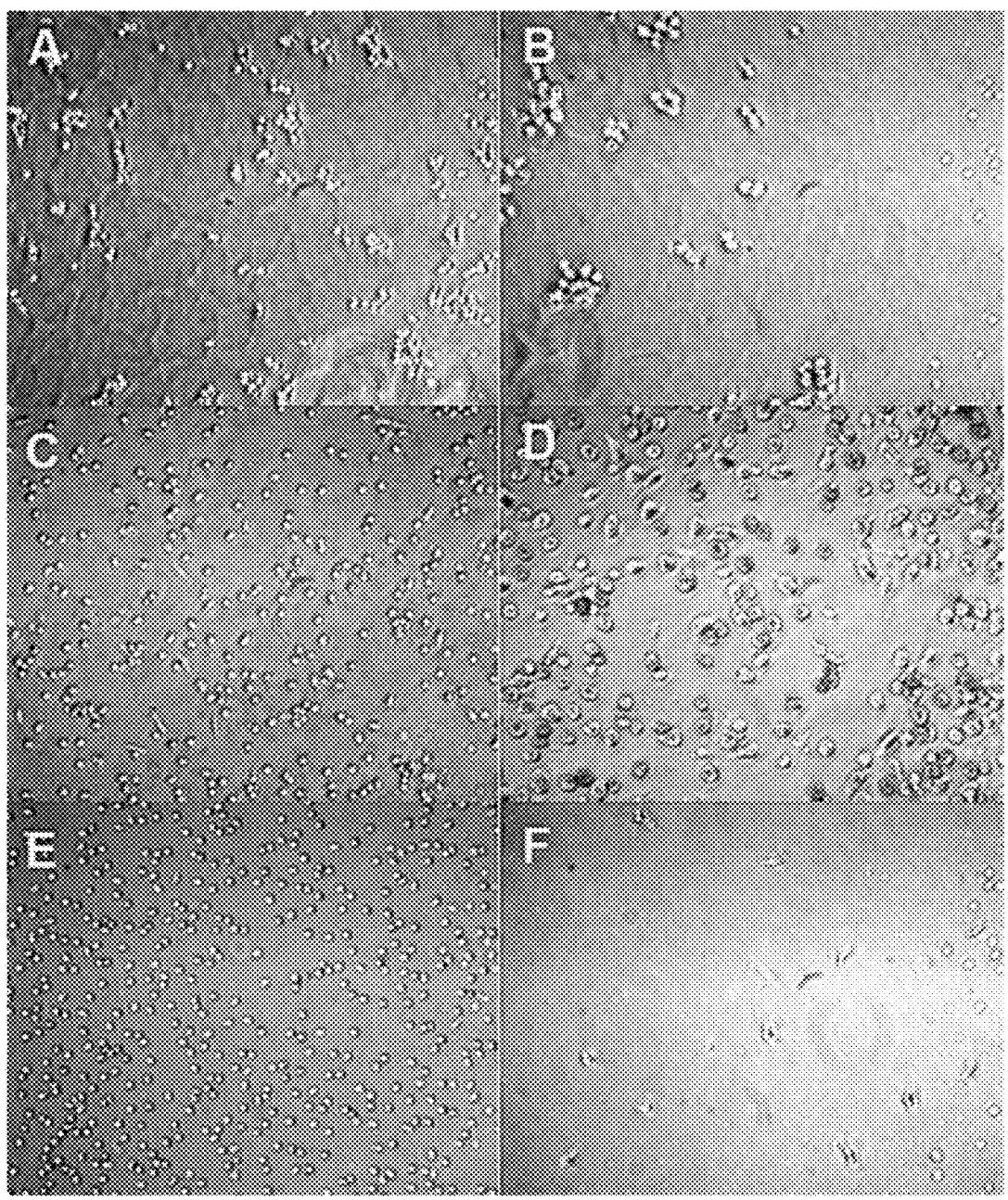
FIG. 13 is a collection of images showing monocyte adhesion on: (i) a thiol-maleimide PEG hydrogel (A, B); (ii) a PEG hydrogel prepared from the photopolymerization of PEG-diacrylate (C, D); and (iii) TCPS (E, F) at 24 hours (A, C, E) and 7 days (B, D, E) at 20× magnification.

Monocyte adhesion results differed significantly between material surfaces over the course of the culture (FIG. 13). The morphology of monocytes on TCPS remained relatively round up through 96 h, but larger with more cytoplasmic spreading by 168 h. Monocytes on thiol-maleimide PEG hydrogels remained round through 168 h with a slightly noticeable increase in size by the end of the culture. Additionally, the monocytes on the thiol-maleimide PEG hydrogel remained in 6-8 cell clusters throughout the culture duration. Monocytes on the photopolymerized PEG hydrogels increased most dramatically in size by 96 h and seemed most phenotypically different. This size increase was still noticeable by 168 h where the cells appeared indented in the middle. By 24 h, monocytes on the photopolymerized PEG hydrogels exhibited a more elongated, thinner shape. With respect to adhesion patterns, adhesion decreased for all substrates over the course of the culture, but to different degrees (Table 8).

TCPS was higher than on photopolymerized PEG hydrogel and thiol-maleimide PEG hydrogel. At the 2 hour point, there were no significant differences in the adherent cell density between photopolymerized PEG hydrogel and thiol-maleimide hydrogel ($p>0.05$). However, at 96 hours, photopolymerized PEG hydrogel showed higher cell density than the thiol-

TABLE 8

Adherent cell densities (cell/mm$^2$) on TCPS, photopolymerized PEG hydrogel, and thiol-maleimide PEG hydrogel surfaces at varying culture times.*

| | | Culture time (h) | | | |
|---|---|---|---|---|---|
| Cell type | Surfaces | 2 | 24 | 96 | 168 |
| Monocyte | TCPS | 1855 ± 515 | 1062 ± 233 | 71 ± 33 | 56 ± 39 |
| | Photopolymerized PEG hydrogel | 1447 ± 226 | 1055 ± 274 | 835 ± 197$^a$ | 708 ± 140$^a$ |
| | Mal-SH hydrogel | 467 ± 115$^{a,b}$ | 468 ± 178$^{a,b}$ | 203 ± 167$^{a,b}$ | 257 ± 284$^{a,b}$ |
| Keratinocyte | TCPS | 28 ± 4 | 74 ± 11 | 166 ± 20 | — |
| | Photopolymerized PEG hydrogel | 17 ± 6$^a$ | 12 ± 6$^a$ | 28 ± 14$^a$ | — |
| | Mal-SH hydrogel | 9 ± 6$^a$ | 3 ± 1$^a$ | 2 ± 1$^{a,b}$ | — |
| Fibroblast | TCPS | 142 ± 28 | 174 ± 53 | 730 ± 62 | — |
| | Photopolymerized PEG hydrogel | 8 ± 6$^a$ | 15 ± 15$^a$ | 34 ± 21$^a$ | — |
| | Mal-SH hydrogel | 13 ± 10$^a$ | 5 ± 4$^a$ | 1 ± 1$^{a,b}$ | — |

*All values expressed as mean ± S.D.; n = 3; "—": data not available.
$^a$p < 0.05 vs. the cell adhesion density on TCPS at the same time point.
$^b$p < 0.05 vs. the cell adhesion density on photopolymerized PEG hydrogel at the same time point.

Adhesion to TCPS decreased most dramatically with the largest decrease between 24 and 96 h. Adhesion to thiol-maleimide PEG hydrogels remained relatively constant through the culture with a slight decrease between 24 and 96 h. The large standard deviation on the thiol-maleimide PEG hydrogels was likely due to the heterogeneous cell distribution on the gel surfaces. Adhesion to photopolymerized PEG hydrogels decreased over time but to a lesser degree than to TCPS. By 24 h, TCPS and photopolymerized PEG hydrogels supported similar levels of adhesion ($p>0.05$) whereas at 96 h and 168 h photopolymerized PEG hydrogels had higher levels of adhesion than either of the other two materials tested ($p<0.05$). This sustained adhesion may be due to the limited and selective protein adsorption exhibited by the hydrophilic hydrogels. Additionally, the monocyte adhesion results, especially at the 2 h point, showed that the adherent cell density followed such trend as TCPS>photopolymerized PEG hydrogel>thiol-maleimide PEG hydrogel. Extensive studies showed that protein molecules selectively adsorb onto hydrophobic surfaces via hydrophobic interactions and as a result, the absorption of adhesion related proteins will potentially promote cell adhesion onto more hydrophobic surfaces. Thus, the adhesion results might imply the relative surface hydrophilicity in the following order: TCPS<photopolymerized PEG hydrogel<thiol-maleimide PEG hydrogel, which is in good agreement with the implications derived from contact angle measurement described in Example 6.

Adherent keratinocyte density on TCPS increased between the 2, 24, and 96 hour time points (Table 8). In contrast, adherent cell density on photopolymerized PEG hydrogel and thiol-maleimide PEG hydrogel surfaces remained lower than on TCPS through the course of the experiment. The low adherent keratinocyte density on photopolymerized PEG hydrogel was also demonstrated in previous studies. Similarly, human dermal fibroblast adhesion density on TCPS showed consistent increase through the course of the experiment (Table 8). At all time points, the adherent cell density on maleimide PEG hydrogel ($p<0.05$) whereas there were almost no noticeable adherent fibroblasts on the thiol-maleimide PEG hydrogel surfaces. Considering keratinocyte and fibroblast adhesion results, it may be possible that PEG within the network minimized certain protein adsorption and, consequently, cell adhesion. However, monocyte adhesion results showed significantly higher level of initial adherent cell density on both photopolymerized PEG hydrogel and thiol-maleimide PEG hydrogel, which implies there might be other driving forces for monocyte adhesion besides generally acknowledged hydrophobic interactions.

Example 8

Synthesis of PEGylated Cysteine Grafted Gelatin (Gel-Peg-Cys)

PEGylated cysteine grafted gelatin (Gel-PEG-Cys) was synthesized following an established procedure. (See Fu, Y., Kao, W. J. *Biomaterials* (2012) 33, 48-58, which is hereby incorporated by reference herein in its entirety and for all purposes.) First, N-hydroxysuccinimide functionalized PEG (bis-NHS-PEG) was synthesized via an established procedure with minor modifications. (See, e.g., Miron, T., Wichek, M. *Bioconjug. Chem.* (1993) 4:568-9.) Briefly, PEG-diol (Mw, 2,000 Da) (5.0 g, 2.5 mmol) was dissolved in 20 mL dry dioxane. Disuccinimidyl carbonate (DSC) powder (6.4 g, 25 mmol) was suspended in another 20 mL dry dioxane and added to the solution. Dimethyl amino pyridine (DMAP) (3.05 g, 25 mmol) was dissolved in 50 mL acetone and added dropwise to the above solution under stirring. The reaction was kept at room temperature for 6 h under argon protection. The activated PEG product was directly precipitated in diethyl ether and dried in vacuo overnight. The crude product was dissolved in 50 mL of dichloromethane (DCM) and washed with 0.5 N HCl solution four times to remove side products. The DCM phase was precipitated in diethyl ether and dried in vacuo to provide 80% yield of product. $^1$H NMR (CDCl$_3$) confirmed the final product: δ 2.8 s, 4H from succinimidyl group; δ 3.65, m, —CH$_1$— from PEG backbone; δ 4.45 t, 2H from —CHOCO—NHS. The product was further analyzed by reverse-phase HPLC (Gilson Model 306 pumps; ELSD-LT2 detector (Shimadzu); C18-DVB, 500 A, 5 µm pore size, 4.6×150 mm (Jordi)) Gradient elution carried out using 30% v/v acetonitrile (ACN)/water for 0-5 minutes, then linearly increased to 70% v/v ACN/water for 5-15 minutes and maintained another 10 minutes. A single peak was observed in the HPLC chromatogram, indicating high purity.

To modify gelatin with L-cysteine, PEG-bis-NHS (1.0 g, 0.43 mmol) was dissolved in 5 mL dry DMF. L-cysteine (0.08 g, 0.66 mmol) was then added into PEG-bis-NHS solution followed by an additional 110 µL DIPEA. The reaction was kept under argon protection for 20 min followed by additional 1% gelatin in PBS solution (60 mL, type A or type B). The reaction was further stirred for 1 hour at R.T. under argon and the pH was maintained at 8.0. The products were dialyzed (6-8 kDa cutoff) for 2 days against ddH$_2$O. The Gel-PEG-Cys solution was then filtered through a 0.22 µm filter, snap frozen and lyophilized. The amount of lysine groups modified on the gelatin macromolecule was estimated by the trinitrobenzene sulfonic acid (TNBS) method and the relative free thiol concentration in the Gel-PEG-Cys solution was calculated base on the Ellman test.

Example 9

Synthesis of Modified Gelatin-PEG Hydrogels

General. Modified Gelatin-PEG hydrogels were prepared according to the synthetic scheme in shown in FIG. 14A and FIG. 14B, by crosslinking PEGdA and Gel-PEG-Cys via photopolymerization. 20% (wt/wt) Gel-PEG-Cys (type A or type B) and 20% (wt/wt) PEGdA solution were prepared with 0.5% Irgacure 2959® in DPBS at 37° C. Gel-PEG-Cys solution was then mixed with PEGdA solution at various concentrations (Table 9). The precursor solution was transferred to a glass bottom petri dish and photo-crosslinked with long-wavelength UV=($\lambda_{max}$=365 nm, 10 mW/cm$^2$) for 90 sec. Hydrogel nomenclature used in this study is defined as "GAXPY" or "GBXPY", where "A" represents type A Gel-PEG-Cys and "B" represents type B Gel-PEG-Cys. "X" is the Gel-PEG-Cys weight percentage and "Y" is the PEGdA weight percentage. For the preparation of collagen hydrogel, rat tail type I collagen was mixed with 10×PBS, 1N NaOH and ice cold ddH$_2$O at 4° C. according to manufacturer's protocol. The final concentration of the collagen was 5 mg/mL. The mixed collagen solution was then allowed to gel at 37° C. for 30 min.

TABLE 9

Formulations of modified gelatin-PEG hydrogels

| Sample formula | PEGdA (wt %) | Gel-PEG-Cys (type A, 300 bloom, wt %) | Gel-PEG-Cys (type B, 75 bloom, wt %) |
|---|---|---|---|
| GA10P5 | 5 | 10 | 0 |
| GA10P7.5 | 7.5 | 10 | 0 |
| GA10P10 | 10 | 10 | 0 |
| GA5P5 | 5 | 5 | 0 |
| GA15P5 | 5 | 15 | 0 |
| GB10P5 | 5 | 0 | 10 |
| GB10P7.5 | 7.5 | 0 | 10 |
| GB10P10 | 10 | 0 | 10 |
| GB5P5 | 5 | 0 | 5 |
| GB15P5 | 5 | 0 | 15 |

Figure 14:
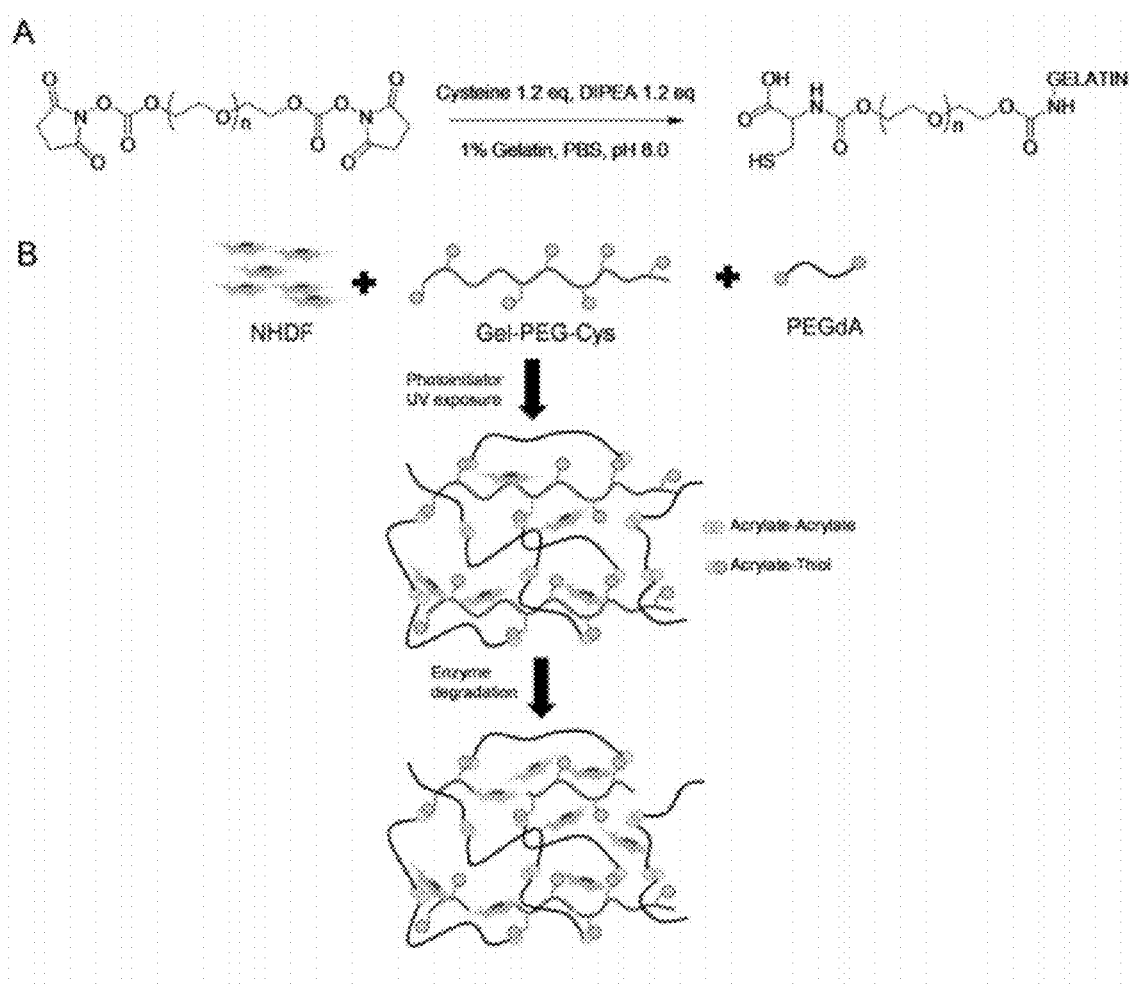
FIGS. 14A and 14B are synthetic schemes for preparation of (a) modified gelatin (Gel-PEG-Cys) via reaction of NHS functionalized PEG L-Cystine and gelatin, and (b) PEG biomaterials via reaction of modified gelatin (Gel-PEG-Cys) with PEG-diacrylate through addition of thiol groups to acrylate carbon-carbon double bonds (i.e., thiol-ene addition) or through addition of the acrylate-acrylate addition.

Proton NMR spectrum of Gel-PEG-Cys in D$_2$O showed: δ1.3, d, 2H, —CH$_2$SH; δ2.90, t, 1H, —CHCH$_2$SH; δ3.65, m, —CH$_2$— from PEG backbone; broad peaks composed of many overlapping small peaks at 1.7, 1.75, 1.92, 3.18, and 4.2 ppm were characteristic gelatin peaks. The introduction of PEG molecule to the gelatin backbone increased solubility of Gel-PEG-Cys and minimized phase separation with PEGdA. The reaction of PEG-bis-NHS, L-cysteine and gelatin resulted in an approximate modification ratio of 70% with type A gelatin and 53% with type B gelatin (Table 10). The average molecular mass of different gelatin products indicated that approximately 17 lysyl residues of each type A gelatin chain and 4 lysyl residues of each type B gelatin chain were modified. Although type A gelatin had a greater degree of lysyl residues modification than type B gelatin, there is no significant difference with the reactive free thiol concentration between two types of Gel-PEG-Cys solutions (Table 10). Both types of gelatin derivatives were further used in gelatin-PEG hydrogel fabrication via thiol-ene photopolymerization with PEGdA. Two concurrent reactions were possible in the mixture containing PEGdA and Gel-PEG-Cys (FIG. 14B). The acrylic radical could either react with another acrylate group or with a thiol functional group via hydrogen abstraction/chain transfer. Changing the polymer concentration and the molar ratio of thiol to acrylate monomers can greatly influence the reaction kinetics, the network structures and physicochemical properties of hydrogel.

TABLE 10

Gelatin modification ratio and free thiol concentration of Gel-PEG-Cys solution

| Samples | Lysyl modification ratio | Free thiol concentration in 20% (wt/wt) Gel-PEG-Cys solution |
|---|---|---|
| Gel-PEG-Cys, type A, bloom 300, Average Molecular Mass: 50,000-100,000 Da | 70.5% ± 4.5% | 11.3% ± 5.3% |
| Gel-PEG-Cys, type B, bloom 75, Average Molecular Mass: 20,000-25,000 Da | 53.3% ± 5.0% | 12.5% ± 1.2% |

Example 10

(A). Bulk Physical Characterization of Gelatin-PEG Hydrogels

Swelling and Degradation Studies

To perform swelling analysis, hydrogel disks were fabricated (diameter=10 mm, thickness=1 mm), incubated in DPBS (3 mL) with 0.1% sodium azide at 37° C. At predetermined time points, samples were carefully removed from DPBS and lightly blotted dry, and the swollen weight ($W_2$) was recorded. After 96 hours, samples were washed with ddH$_2$O, lyophilized and the dried weight ($W_{dry}$) was measured. Equilibrium weight swelling ratio (Qs) was calculated as: $Qs=(W_t-W_{dry})/W_{dry}$. The volume swelling profiles of hydrogel disks were measured according to their surface area change. Hydrogels were allowed to reach equilibrium via incubating in DPBS for 3 days. The surface area of each hydrogel was then recorded and compared with the initial area (10 mm diameter plate). Since the thickness of each sample was not observably changed throughout the swelling experiment, the change in the thickness was not considered.

To evaluate FITC-dextran release profiles, type B gelatin-PEG hydrogels were incorporated with 1 mg/mL FITC-dextran (Mw: 4,000 Da, 70,000 Da and 500,000 Da) right before gelation. The samples were then incubated in DPBS containing 0.1% sodium azide. The supernatant was collected and replaced with fresh DPBS at each time point. The fluorescence intensity of FITC-dextran in the supernatant was detected by microplate reader with excitation at 485 nm and emission at 520 nm (FluoStar Omega, BMG Labtech, Germany). The cumulative dextran amount in the supernatant was calculated and compared with the dextran amount in the initial hydrogel.

To evaluate gelatin dissolution profiles, samples were incubated in DPBS containing 0.1% sodium azide at 37° C. At each time point, the entire volume of supernatant was collected and replaced with fresh DPBS. The gelatin concentration in the supernatant was detected via BCA™ protein assay kit (Thermo Scientific, U.S.A). Gelatin dissolution percentage was calculated as the cumulative gelatin weight in the supernatant ($W_s$) compared with the gelatin weight in the initial hydrogel ($W_h$); percentage of gelatin dissolution=$(W_s)/(W_h)\times100\%$.

To determine the possible effect of collagenase on hydrogel degradation, samples were prepared as described above, placed in glass vials with DPBS containing 0.4 mg/mL type I collagenase and 0.1% sodium azide. Samples were then placed on a platform shaker at 37° C. The collagenase solution was changed every two days to maintain enzyme activity. After 1, 3 and 7 days, samples were washed with ddH$_2$O and lyophilized to obtain the dried weight. The percentage of degradation was calculated by the dried weight of each time point divided by the dried weight of the initial hydrogel. Samples incubated in DPBS without collagenase were used as baseline comparison.

Bulk Rheological characterization of the hydrogel was performed with an ARESLS2 2000ex rheometer (TA Instruments, USA) equipped with 8 mm parallel disk geometry. The frequency-sweep was applied with a range of 0.1 to 10 Hz with 5% strain. Hydrogel samples were un-swollen, swollen (incubated with DPBS for 7 days) or encapsulated with fibroblasts (106 cell/mL hydrogel, culture for 7 days). The magnitude of the complex shear modulus (G*) was calculated as G*=G'+iG".

Figure 15:
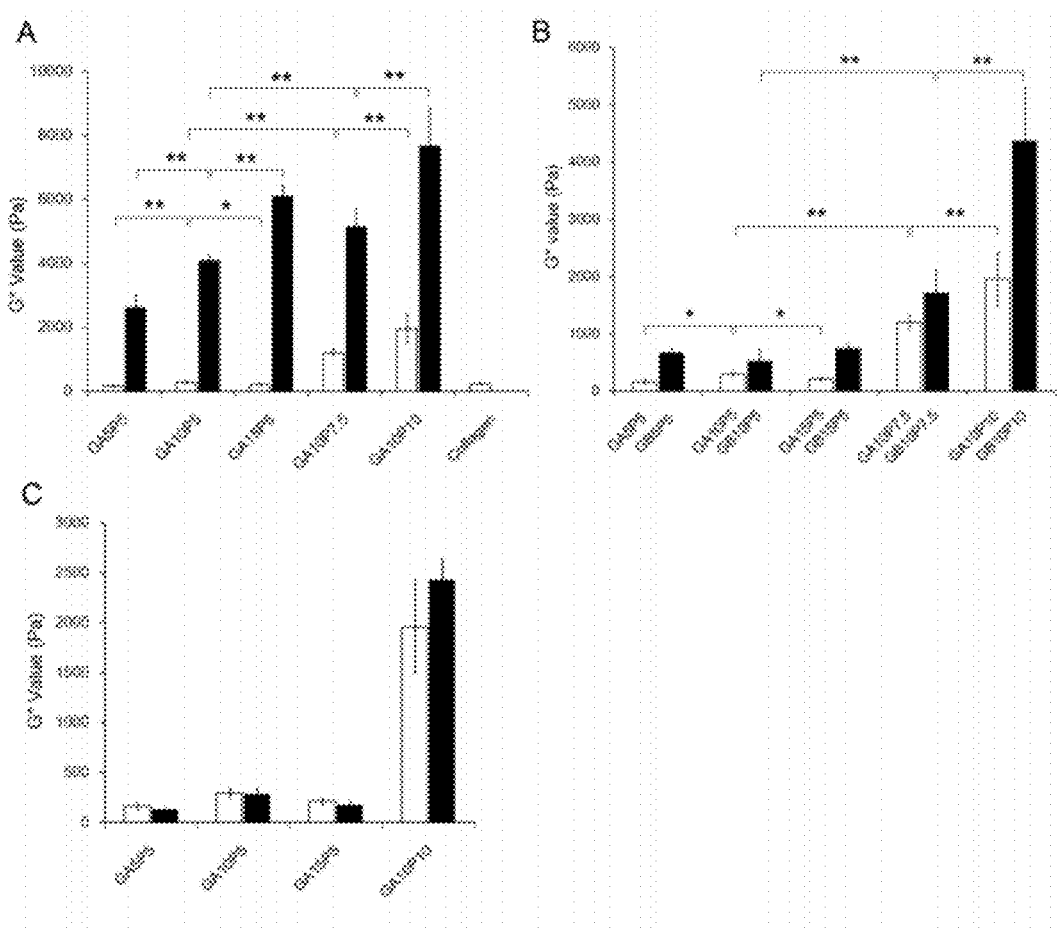
FIGS. 15A, 15B and 15C each represent a graph illustrating the magnitude of the complex shear modulus for various samples and concentrations of modified gelatin-PEGdA hydrogels.

Increasing either PEGdA or Gel-PEG-Cys concentration significantly increased G* value in un-swollen samples (FIG. 15A, black bars). With constant PEGdA concentration (5%), G* value increased from 2610±400 to 6102±399 Pa with increasing Gel-PEGCys content (p<0.01). PEGdA concentration also showed a positive correlation with the hydrogel stiffness. G* values increased from 4073±192 Pa for GA10P5 to 5140±551 Pa for GA10P7.5 and 7627±1200 Pa for GA10P10 (p<0.01). These phenomena, however, were quite different when using fully hydrated samples (FIG. 15A, white bars). All five swollen samples had significantly lower G* value than respective un-swollen samples, especially those containing 5% PEGdA. When completely swelled, hydrogels containing different gelatin concentrations exhibited similar G* value (FIG. 15A, white bars). The PEGdA concentration in the swollen hydrogels remained positively correlated with G* (i.e., 294±47 Pa for GA10P5 to 1203±129 Pa for GA10P7.5 and 1959±469 Pa for GA10P10, FIG. 15A, white bars, p<0.01). Similar trends were also observed in hydrogels fabricated with type B Gel-PEG-Cys (FIG. 15B, black bars). When compared with hydrogels formed with type A Gel-PEG-Cys, hydrogels containing type B Gel-PEG-Cys generally had higher G* values (FIG. 15B). With the same polymer composition under=swollen status, the storage modulus was directly dependent on the crosslink density of the network. Higher PEGdA or Gel-PEG-Cys concentration increased the crosslink density and thus resulted in a higher G* value. Swollen gels had significantly lower G* values than un-swollen gels due mainly to the higher water content and more relaxed state of the polymer chains. The bulk properties of the hydrogels could also be influenced by the presence of encapsulated cells. However, there were no statistical differences between cell-containing and cell-free PEG-gelatin hydrogel samples (FIG. 15C). The results showed that water content and PEGdA concentration played a significant role in the bulk viscoelasticity of the hydrogels.

Figure 16:
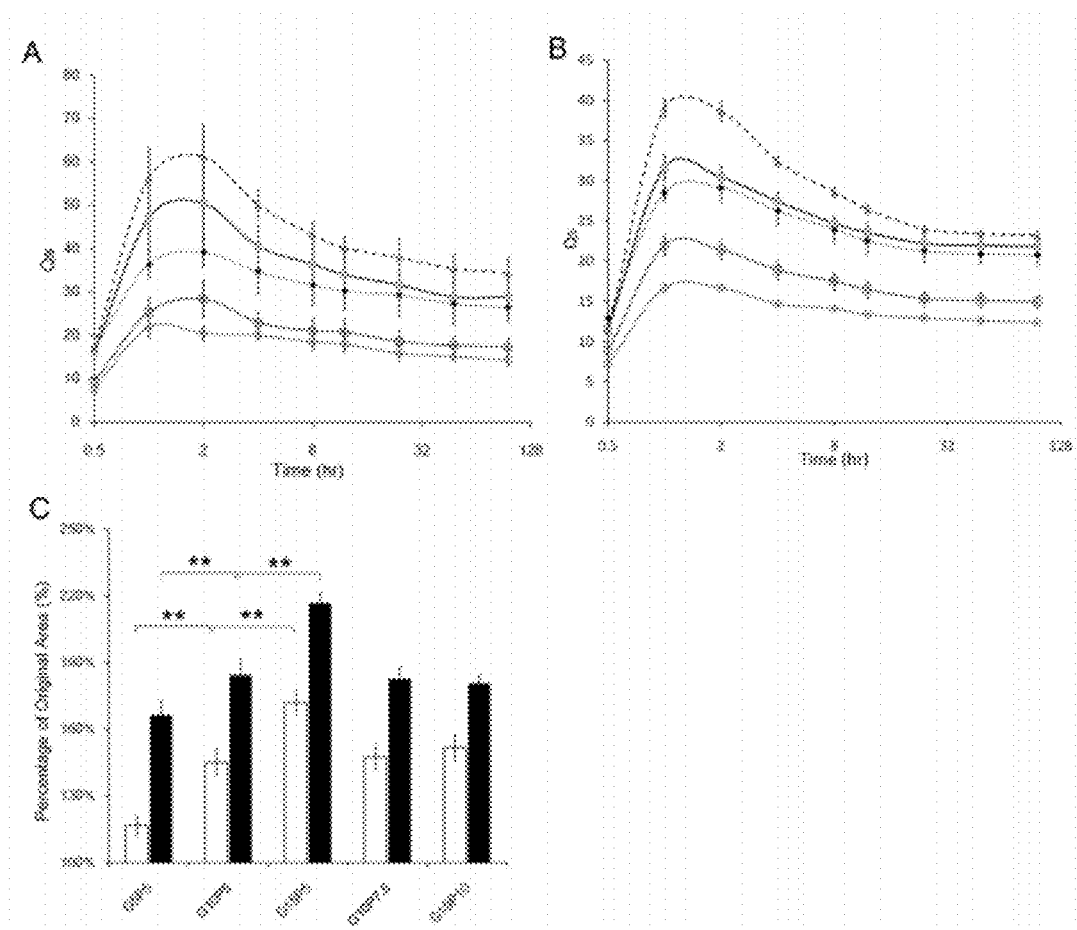
FIGS. 16A and 16B are graphs illustrating the equilibrium weight swelling ratio of various modified gelatin-PEGdA hydrogel as a function of time.
FIG. 16C: relative surface area change of type A gelatin-PEG hydrogels (white bars) and type B gelatin-PEG hydrogels (black bars). ** $p<0.01$.

Both PEGdA and Gel-PEG-Cys concentrations significantly affected the mass swelling characteristics of the hydrogel (FIG. 16A). Increasing PEGdA concentration resulted in lower mass swelling ratio. GA10P5 ($Q_{max}$=50.4±8.3 at 2 hour) displayed about twofold larger $Q_{max}$ value than GA10P7.5 ($Q_{max}$=28.4±4.3 at 2 hour) and GA10P10 ($Q_{max}$=21.9±2.4 at 1 hour). The negative effect of PEG concentration on mass swelling profiles of hydrogels had been well studied and characterized.

Increasing PEGdA concentration resulted in higher crosslink density and led to a lower mass swelling ratio. Gelatin concentration had a reverse effect on the hydrogel mass swelling profile (FIG. 16A). Hydrogels containing 5% PEGdA with 5%, 10% and 15% Gel-PEG-Cys had $Q_{max}$ values of 39.1±3.4, 50.4±8.3 and 61.2±7.6 respectively (p<0.01).

Hydrogels composed of type B Gel-PEG-Cys also showed similar mass swelling trends as hydrogels with type A Gel-PEG-Cys (FIG. 16B). Only Gel-PEG-Cys concentration had a positive correlation with the area change profile of the hydrogels (FIG. 16C). The swelling area increased significantly with increasing Gel-PEG-Cys concentration. Since Gel-PEGCys could react with PEGdA via thiol-acrylate reaction and compete with the acrylateacrylate reaction, increasing Gel-PEG-Cys concentration increased the probability of thiol-acrylate reaction while decreased the acrylate-acrylate reaction. Since the thiolacrylate cross-linker involves larger macromolecules that are more flexible than acrylate-acrylate cross-linker, hydrogels containing more Gel-PEG-Cys would be expected to have less chain rigidity and higher water content, mass swelling and larger final area.

Figure 17:
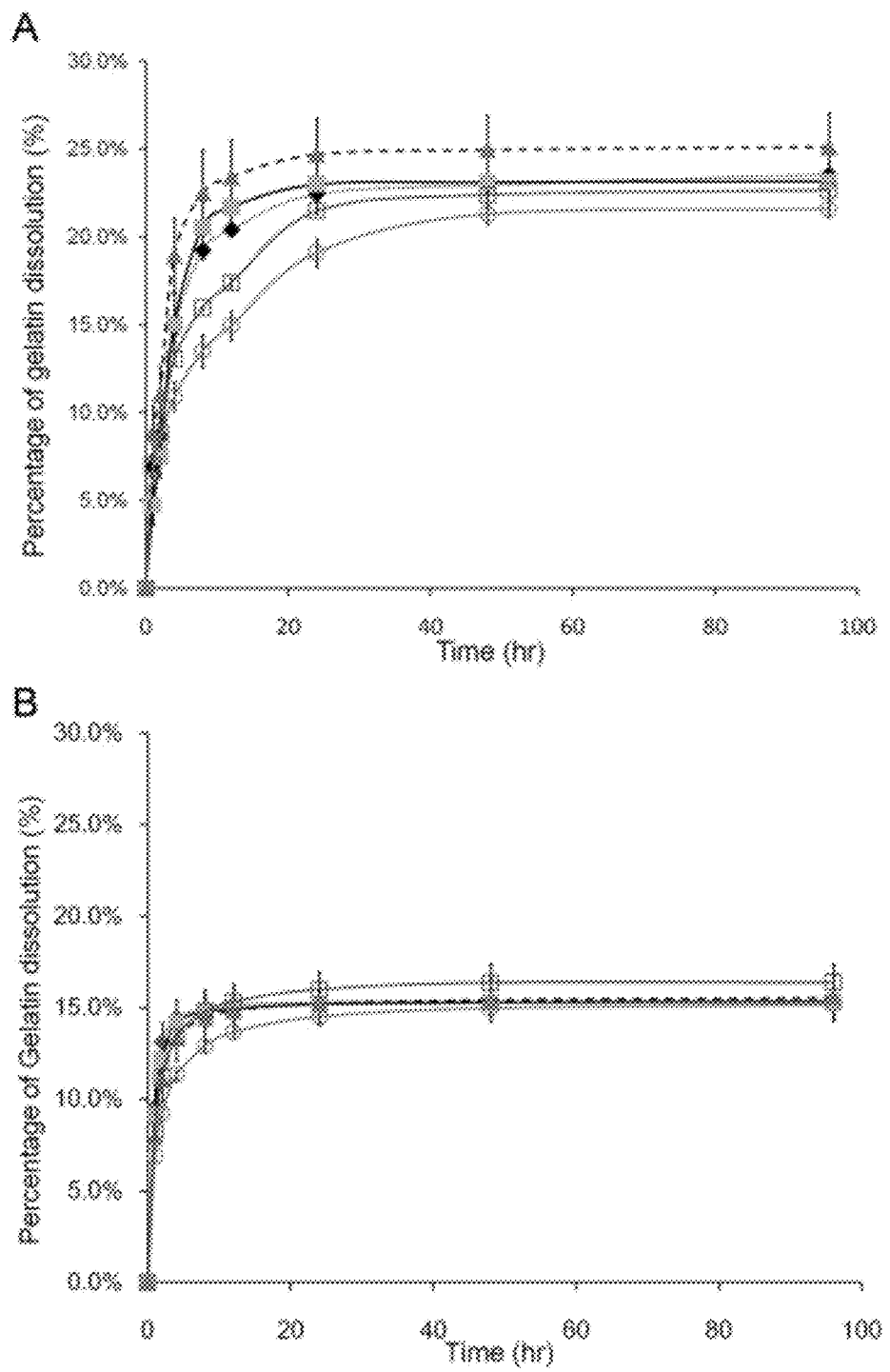
FIGS. 17A and 17B are graphs illustrating the percentage of gelatin dissolution for various modified gelatin-PEGdA hydrogels as a function of time.

Gelatin-PEG hydrogels showed a rapid initial gelatin dissolution that equilibrated within 24 hour (FIG. 17) indicating most of the Gel-PEG-Cys was stably crosslinked within the hydrogel network. There was no significant difference in the gelatin dissolution profile in all five formulations with either type A or type B gelatins (FIGS. 17A and 17B).

Figure 18:
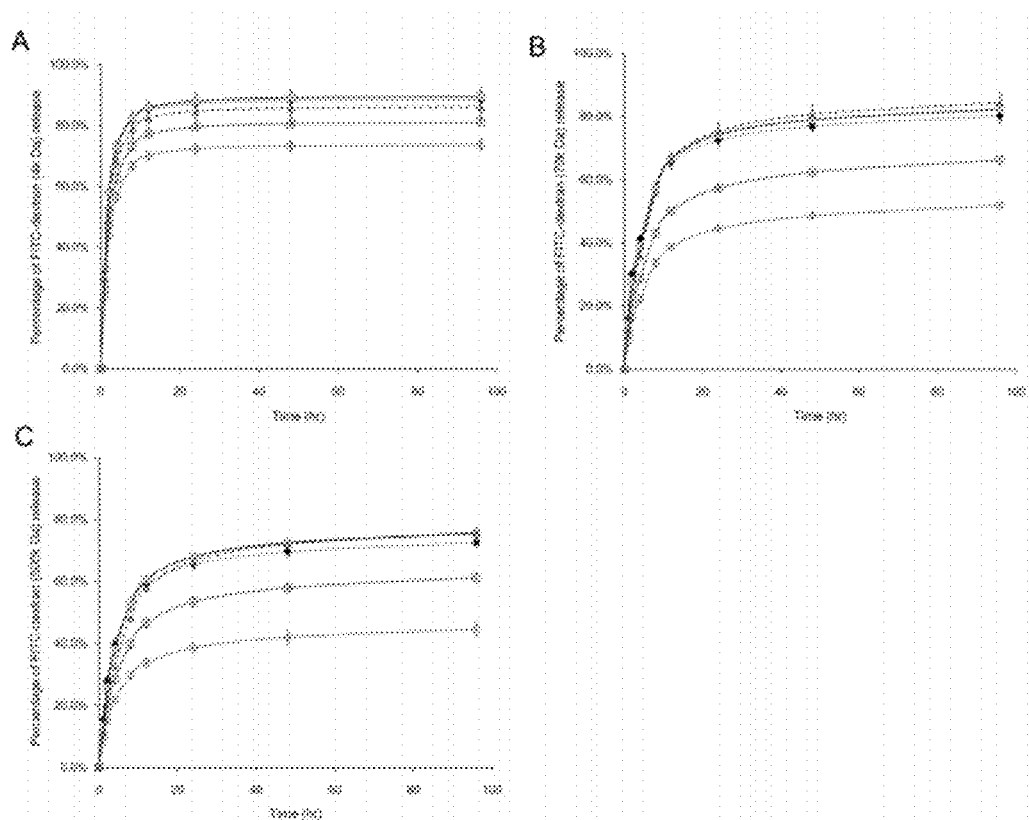
FIGS. 18A, 18B and 18C are graphs illustrating the percentage of FITC-dextran release as a function of time from type B gelatin-PEG hydrogels (◆:GB5P5, ■: GB10P5, ▲: GB15P5, □: GB10P7.5, ○: GB10P10). Release kinetics of FITC-dextran with a different molecular weight are shown in each graph.

Different with gelatin dissolution, non-covalently incorporated FITC-dextran displayed significantly different release profiles. As shown in FIG. 18, FITC-dextran with lower molecular weight (4,000 Da, FIG. 18A) rapidly diffused out of the hydrogel within 24 hours while FITC-dextran with higher molecular weight (70,000 Da, FIG. 18B and 500,000 Da FIG. 18C) diffused much slower. The variation of gelatin concentration has no effect on the FITC-dextran release profile while the higher PEG concentration significantly retarded the release of dextran. These results indicated the hydrogels with higher PEG concentration had more tightly structure which impeded the diffusion of large molecule.

Figure 19:
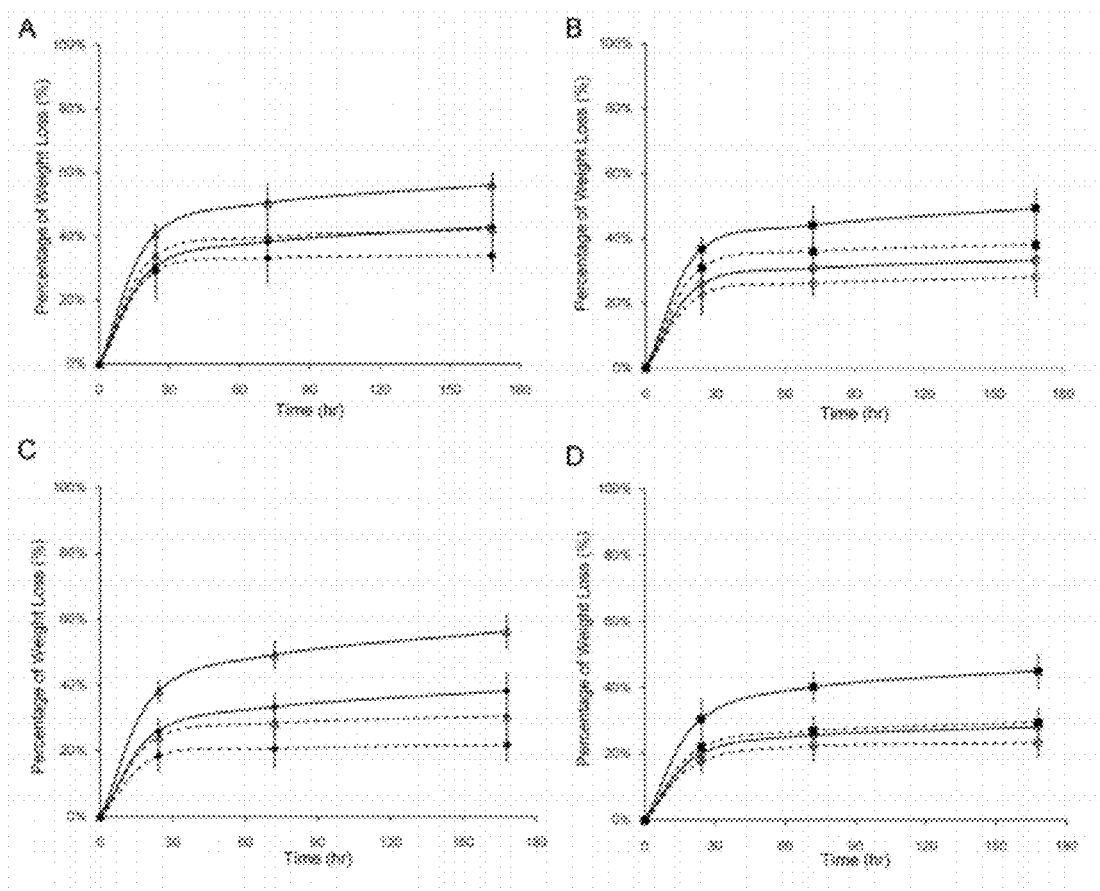
FIGS. 19A, 19B, 19C and 19D are graphs illustrating the percentage of weight loss for various modified gelatin-PEGdA hydrogel as a function of time. Enzymatic degradation profiles of type A gelatin-PEG hydrogels (FIG. 19A: GA5P5 (◆) versus GA15P5 (□) and FIG. 19B: GA10P5 (■) versus GA10P10 (○)) and type B gelatin-PEG hydrogels (FIG. 19C: GB5P5 (◆) versus GB15P5 (□) and FIG. 19D: GB10P5 (■) versus GB10P10 (○)). The degradation profile of each formulation incubated with type I collagenase (solid line) was compared with hydrogel incubated in PBS (dash line).

Hydrogels incubated with collagenase displayed larger mass loss than those incubated in the DPBS at 3 and 7 days (FIG. 19), indicating that the modified gelatin could be recognized and digested by collagenase I. The mass loss was more pronounced in hydrogels with higher gelatin concentration (FIGS. 19A and C) and lower PEG concentration (FIGS. 19B and D). Contrasting with unmodified gelatin or collagen hydrogels which could be completely degraded by collagenase, all gelatin-PEG hybrid hydrogels maintained structural integrity after 7 days. This could be due to the polymerization of PEGdA-PEGdA formulated the robust PEG network which would not be affected by collagenase, thus maintained the overall structure. Similar observations were reported when PEGdA was introduced into methacrylated gelatin hydrogels.

Example 11

Micro-Rheological Properties of Modified Gelatin-PEG Hydrogels

Figure 20:
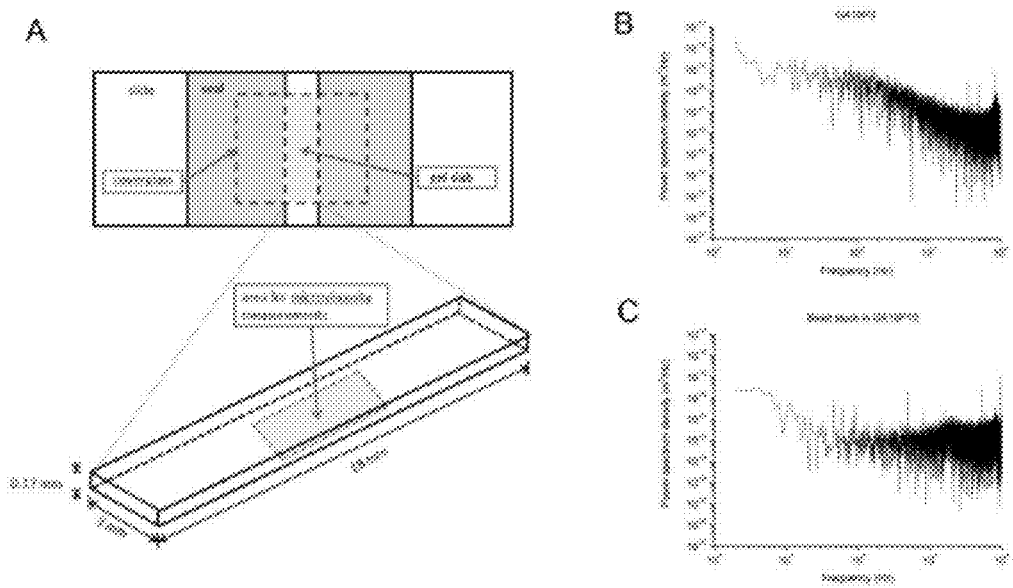
FIG. 20A is a diagram illustrating the set-up for measuring the micro-rheological properties of the modified gelatin-PEG hydrogels.
FIGS. 20B and 20C are graphs illustrating the power spectrum density of the hydrogels GA10P3 and GA10P10 (respectively) as a function of frequency.

The micro-rheological properties of hydrogels were determined by measuring the Brownian motion of polystyrene beads embedded in gelatin-PEG hydrogels and trapped by optical tweezers. The hydrogel precursor solutions were prepared according to 2.3 before a 20% vol/vol bead solution (0.005% wt/vol in PBS) was added. The solution was then injected into a glass micro-chamber with a cover glass bottom and a glass slide top (FIG. 20A). The entire assembly was subsequently sealed and exposed to UVC (~4 mW/cm$^2$) for 60 seconds to set the gel. A single beam from a Nd:YVO4 laser (1064 nm, Spectra-Physics Lasers) was used as trapping laser and another wavelength (830 nm, Point Source) was used as the detection laser. The bead position was recorded by a QPD sensor with resolution down to nanometer at 20 kHz. The time domain data was then Fourier transformed and analyzed in frequency domain. Equation 1 describes the position power spectrum, Sx(f), of a trapped bead, where is the Boltzmann's constant; is absolute temperature; is the drag coefficient, which relates to local viscosity and the radius of bead as shown in eq. 2; $f_c$ is the corner frequency, which relates to drag coefficient and the trapping stiffness of optical tweezers as shown in eq. 3. The local viscosity, η, of the hydrogel was obtained from the power spectrum of the bead (FIGS. 20B and C). Due to the short working distance of the high NA oil immersion lens used for optical trapping and imaging, only the layer within 10 μm of the cover glass was clearly visible. Beads that moved on the camera feed from a camera attached to the microscope were deemed to have Brownian motion (FIG. 20B). Those that did not move were considered as stuck (FIG. 20C). Experiments for each formula were repeated at least once, and ten beads from various locations in each micro-chamber were observed. Only samples with beads showing Brownian motion consistently throughout the observable region were used to determine local viscosity. All measurements were done at a temperature of 23.5±0.5° C., in the central region of the gel slab 5 μm above the cover glass.

$$S_x(f) = \frac{\kappa_B T}{\gamma \pi^2 (f_C^2 + f^2)} \quad \text{(eq. 1)}$$

$$\gamma = 6\pi\eta a \quad \text{(eq. 2)}$$

$$f_C = \kappa / 2\pi\gamma \quad \text{(eq. 3)}$$

The diameters of the polystyrene beads used in this experiment were 1.09 μm and 1.87 μm, which were much smaller than mammalian cells. Thus, the local viscosity represented the viscoelastic properties of hydrogels on a sub-cellular scale. The surface modification of the polystyrene beads did not affect their Brownian motion within the hydrogel. Both types of beads behaved similarly in all formulae. Visible Brownian motion of the beads was observed in GA10P3 (FIG. 20B) with different viscosity values at different locations (Table 11), which indicated that the micro-viscosity in gelatin-PEG hydrgoel was not homogeneous. When the PEGdA concentration was raised to 5% and 7.5% in the precursor solutions (GA5P5, GA10P5, GA15P5, and GA10P7.5), the Brownian motion of the beads was only obtained in the boundary area (60-100 μm from the sides of the gel slabs) while not measurable in the middle of the hydrogels (FIG. 20C). All the beads appeared stuck when the PEGdA concentration was raised to 10% (GA10P10). Different with PEGdA concentration, the Gel-PEG-Cys concentration did not have significant effect on the behavior of the beads. The local viscosity properties are mainly dependent on the close proximity of the cavity walls formed by PEGdA and Gel-PEG-Cys fiber networks and the extra drag from the long, flexible gelatin-PEG polymers present inside the cavity. Individual pores in one hydrogel may have different sizes and different distribution of free polymer ends, thus producing different local viscosities for each bead. Increasing the concentration of PEGdA in the hydrogels will increase the density of crosslinking and decrease pore size, thus directly restrict the movement of the beads.

TABLE 11

Micro-viscosity detection of modified gelatin-PEG hydrogels by optical tweezers

| Sample formula | Local viscosity at different locations (0.001 × Pa-sec)[#] | | | | Beads stuck in hydrogel |
|---|---|---|---|---|---|
| | Location 1 | Location 1 | Location 1 | Location 1 | |
| GA10P3 | 2.71 ± 0.18 | 1.05 ± 0.08 | 2.78 ± 0.05 | 2.29 ± 0.36 | No |
| GA5P5 | N/A | N/A | N/A | N/A | Yes |
| GA10P5 | N/A | N/A | N/A | N/A | Yes |
| GA15P5 | N/A | N/A | N/A | N/A | Yes |
| GA10P7.5 | N/A | N/A | N/A | N/A | Yes |
| GA10P10 | N/A | N/A | N/A | N/A | Yes |

[#]At each location the same trapped bead was used to measure local viscosity 3 times.
N/A: Not measurable because no bead movement was observed in central region.

Example 12

(A). In Vitro Cell Culture

Neonatal human dermal fibroblasts (NHDF) and neonatal human dermal keratinocytes (NHEK) were purchased from Lonza (Lonza, N.J., USA). NHDF was cultured in fibroblast basic medium (FBM) supplemented with 10% fetal bovine serum (FBS). Fibroblasts were passaged every three days and cells between passages 5 to 10 were used for all experiments. Human keratinocytes were cultured in KGM-Gold® keratinocyte growth medium (Lonza, N.J., USA). Keratinocytes between passages 2 to 5 were used. 2D cell adhesion was performed on hydrogel samples prepared as described above. Samples were transferred into a 24 well culture plate and incubated with respective culture medium for 2 hours at 37° C. to reach equilibration. NHDF or NHEK was trypsinized and resuspended to single cell suspension at $1\times10^5$ cells/mL. 1 mL of cell suspension was added on each hydrogel sample and after 3 days, live/dead staining (Invitrogen, N.J., U.S.A) was used to evaluate cell viability and adhesion on the hydrogel surfaces.

(B). 2D Cell Adhesion and 3D Cell Encapsulation

For 3D cell encapsulation, precursor solutions of various PEGdA and Gel-PEG-Cys concentrations were prepared. The NHDF was trypsinized, resuspended and mixed with hydrogel precursor solutions at a final concentration of $2\times10^6$ cells/mL. Mixed precursor solutions were gently agitated and transferred to glass bottom petri dishes and subjected to UV exposure for 90 seconds (10 mW/cm$^2$). Subsequently, cell encapsulated hydrogels were detached from the mold and incubated in culture medium. After 14 days, cell entrapped hydrogels were washed with DPBS and fixed in 4% paraformaldehyde for 4 hours at room temperature followed with incubation in 0.25% Triton X-100 plus 1% BSA in PBS solution for 2 hours. Cytoskeletal F-actin was stained with 1 U/mL Alexfluo 488 conjugated phalloidin (Invitrogen, N.J., U.S.A) at 4° C. overnight. Fluorescence images of the F-actin distribution were acquired by confocal microscope (F1000, Olympus, Japan).

Figure 21:
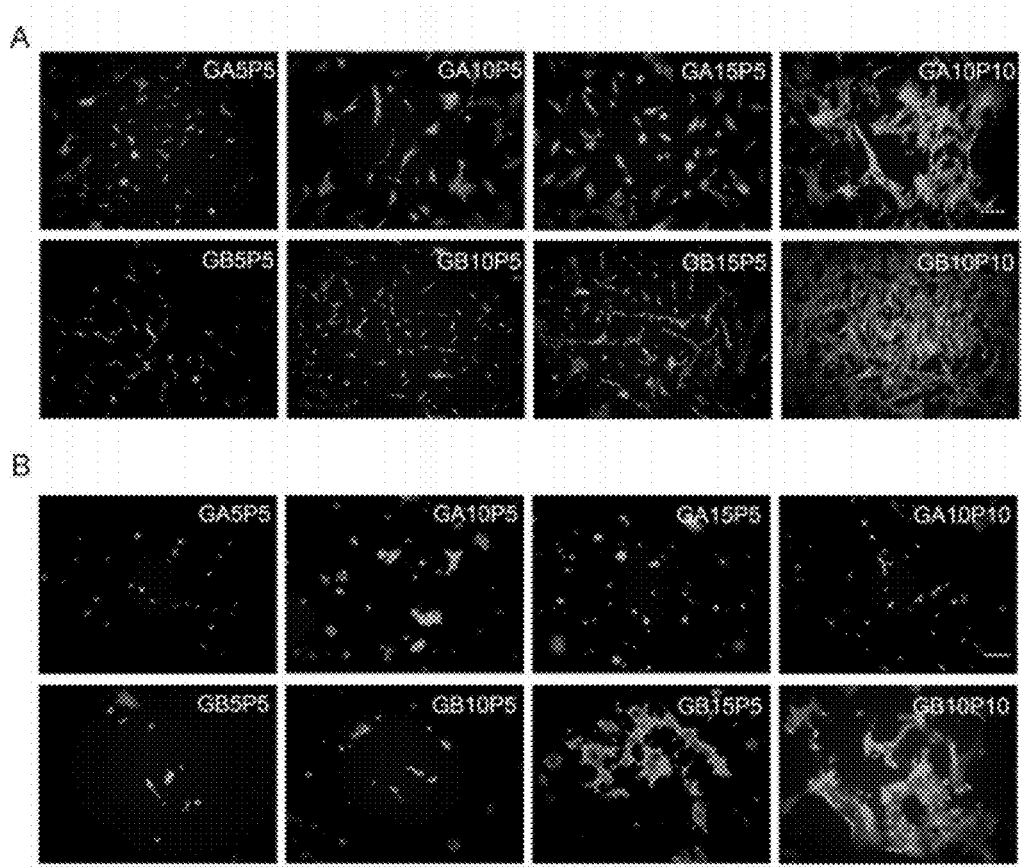
FIGS. 21A and 21B are a collection of images showing fibroblast (FIG. 21A) and keratinocyte (FIG. 21B) adhesion for various 2D cell culture samples of modified gelatin-PEG hydrogels.

G5P5, G10P5 and G15P5 were selected for 2D cell culture since these formulations exhibited similar bulk rheological properties but different degree of biofunctionality from various gelatin concentrations. G10P10 had the highest gel stiffness and was employed as a comparison. NHDF adhered to all surfaces but with different cell morphologies by 3 days (FIG. 21A). On hydrogels containing 5% PEG, most cells exhibited elongated morphology with few interconnections. More adherent cells were observed on GA15P5 and GB15P5 (FIG. 21A). Fibroblasts displayed spindle-like shape on the rigid surface (G10P10) than on softer samples. On GA10P10 and GB10P10, fibroblasts covered most of the hydrogel surface after 3 days; with morphology similar to those on TCPS. Most of the hydrogels only supported minimal keratinocyte adhesion with round morphology (FIG. 21B). Although higher adherent density could be observed on GB15P5, keratinocytes formed extensive cell clusters which indicated insufficient cell spreading and the likelihood for apoptosis. Whereas keratinocytes spread out, exhibited flatten morphology and formed intercellular networks on GB10P10. Cell interaction with the extracellular matrix (ECM) depends on ligation induced and traction-induced signaling pathways. Higher gelatin concentration provided more cell binding motifs thus promoted cell adhesion. Similarly, smooth muscle cells formed more focal adhesion and stretched F-actin fibers on substrates with increasing stiffness. Thus, the increased cell density on GA10P10 and GB10P10 is due to higher initial adherent density and higher rate of cell proliferation.

Figure 22:
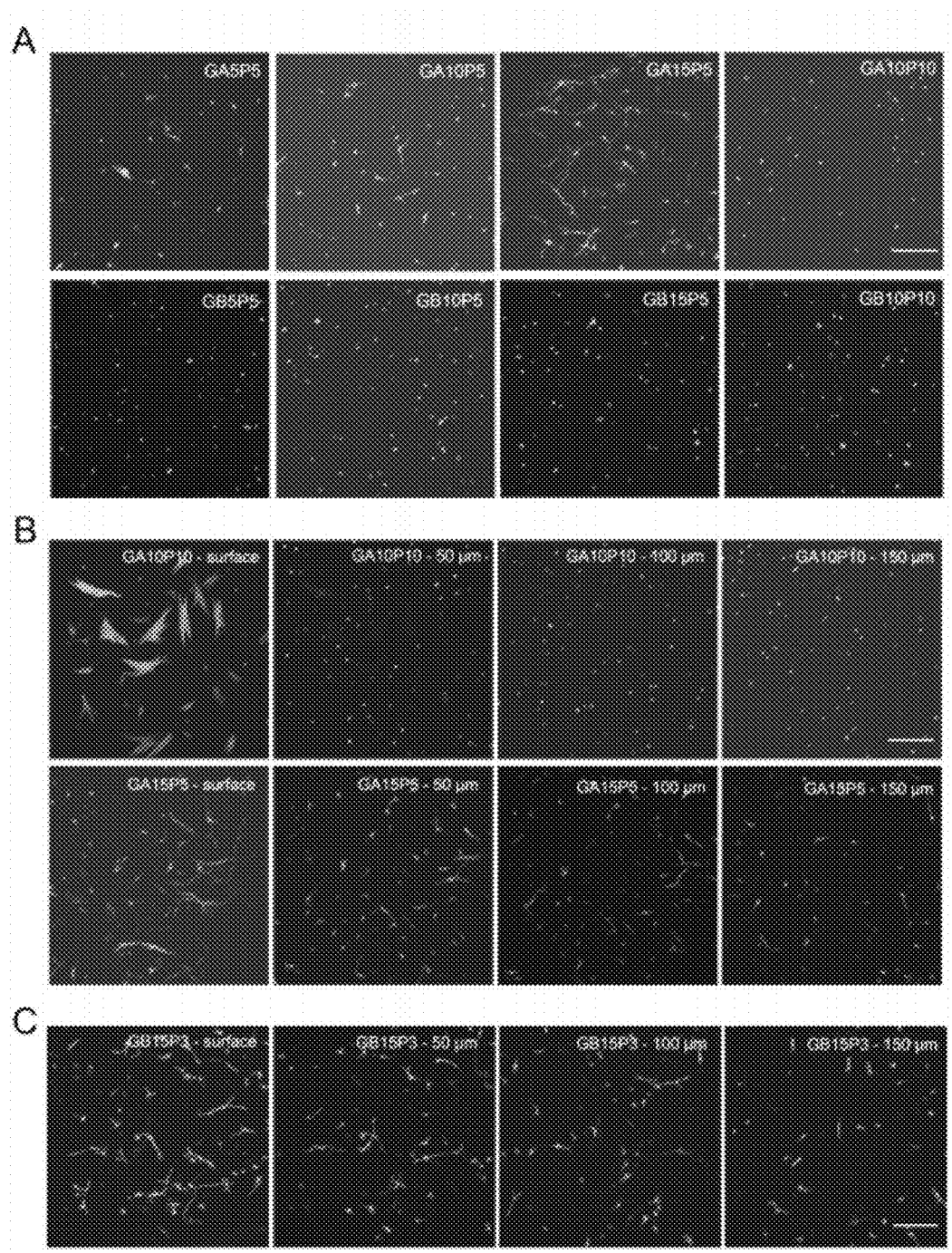
FIGS. 22A, 22B and 22C are a collection of images showing fibroblast adhesion for various cell culture samples of three-dimensional cell encapsulation in gelatin-PEG hydrogels. Fibroblasts were photoencapsulated in Gel-PEG-Cys hydrogels and cultured for 14 days. The cell cytoskeletons were stained with Alex-488 conjugated phalloidin.

When entrapped in the hydrogel, cell behavior was markedly different from that on a two-dimensional surface. After cultured for 2 weeks, fibroblasts started to spread and formed extensions in softer type A gelatin-PEG hydroge (FIG. 22A, upper panel). Although elongated cell phenotype could be found in GA5P5, GA10P5 and GA15P5 (all have similar G* values), extensive cell spreading and intracellular network formation were only observed in GA15P5 which had the highest gelatin concentration. The higher gelatin concentration likely provided more cell binding sites to support cell spreading and proliferation. With the same gelatin concentration, GA10P5 and GA10P10, well spread cells were found within the softer hydrogel. GA15P5 and GA10P10 were then imaged at four different depths. As shown in FIG. 22B, cell spreading and network formation could be observed in all four depths in G15P5. In contrast, fibroblasts were round in three depths within the bulk of G10P10. The extensively spread cells in the first layer of G10P10, are believed to be cells on the hydrogel surface thus behaved similarly as those in the 2D culture. No cell spreading was observed in hydrogels fabricated with type B Gel-PEG-Cys of the same formulation as type A Gel-PEG-Cys (FIG. 22A, lower panel). Since hydrogels fabricated with typeB Gel-PEG-Cys had higher G* value than those with type A (FIG. 15B), these hydrogels might be too rigid for cells to spread. To test this hypothesis, hydrogel with 15% type B Gel-PEG-Cys and 3% PEGdA (GB15P3) which had lower stiffness and higher swelling profile were fabricated. After 7 days, fibroblasts exhibited well-spread morphology and formed intercellular connections, indicating that GB15P3 had the optimal mechanical stiffness to facilitate this type of cell behavior (FIG. 22C).

Figure 23:
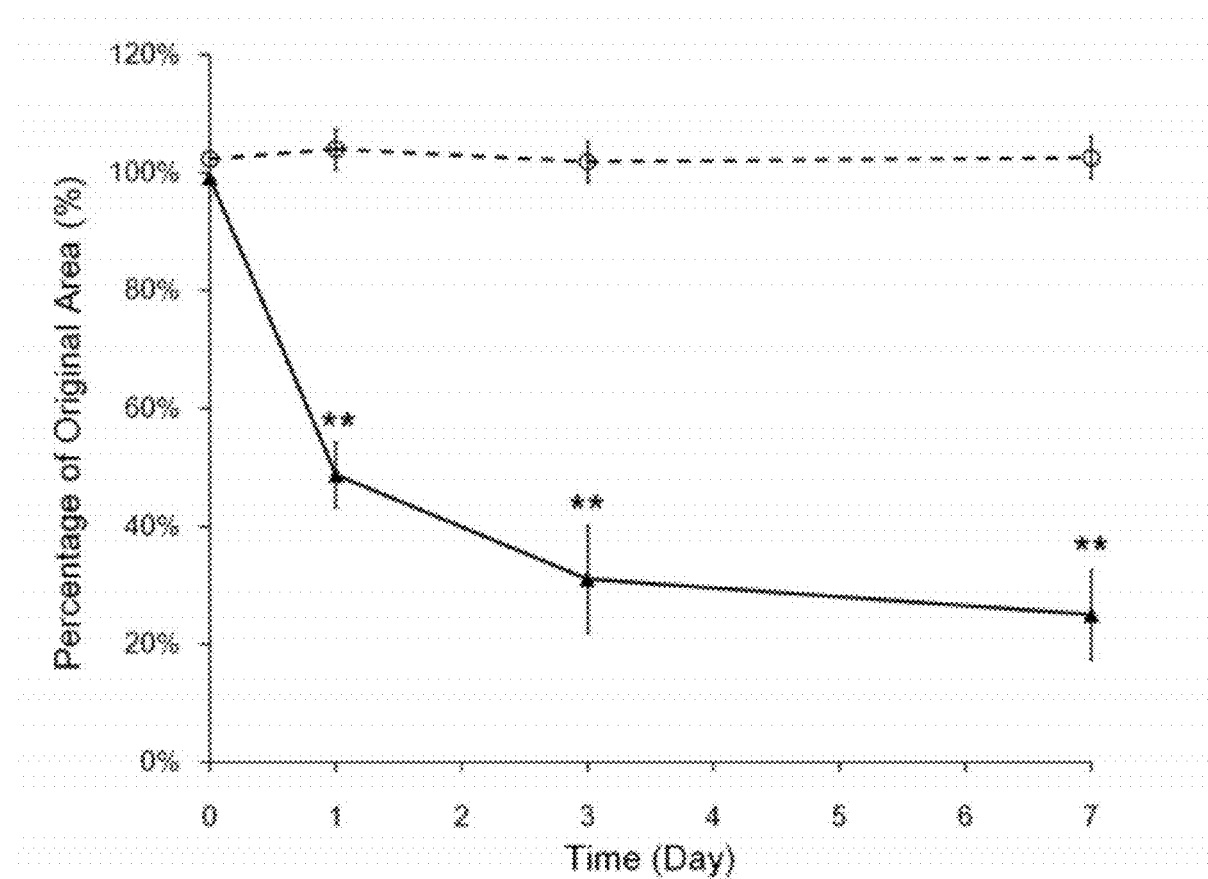
FIG. 23 is a graph illustrating the change over time in percentage of area covered by cultured fibroblasts encapsulated within a collagen hydrogel and Gel-PEG-Cys hydrogel. Fibroblasts were encapsulated in 5 mg/mL collagen gel (solid line) and GA15P5 hydrogel (dashed line). The area covered by the fibroblasts were determined at various tune points and resistance to gel contraction was calculated by the percentage of original gel area at day 0. ** $p<0.01$, compared with GA15P5.

Hydrogel based on gelatin or collagen has long been used for cell encapsulation. Two major disadvantages of collagen-based scaffolds are their limited physical integrity to match soft tissue structure and extensive contraction when encapsulated with contracting cells. For this study, the fibroblasts were encapsulated in 5 mg/mL collagen hydrogel and compared with GA15P5. These two hydrogels had similar complex shear modulus and both supported cell adhesion and spreading in 3D environment. As shown in the graph of FIG. 23, unmodified collagen hydrogel underwent rapid contraction and curling (i.e., contracted in area). In contrast, the bulk volume of GA15P5 was comparable as the initial after 14 days of culture. The significant difference in contraction might be due to the different extent of cell proliferation as well as the enhanced hydrogel rigidity from the covalently crosslinked gelatin-PEG matrix.

Example 13

(A) Cell Culture and Media

Neonatal human dermal fibroblasts (NHDF) were obtained from Lonza (NJ, USA) and cultured in 75 cm$^2$ T-flask using fibroblast basic medium-2 (FBM-2, Lonza) supplemented with 10% fetal bovine serum (FBS, Atlanta Biologicals, Lawrenceville, Ga., USA). Fibroblasts with passage 5-10 were used in the following experiments. Unmodified NIKS keratinocytes (NIKS) were obtained from existing cell stocks (Allen-Hoffmann, B. L. *J. Invest. Dermatol.* (2007) 127: 998-1008.) NIKS$^{VEGF}$ keratinocytes (Statatech Corp, Madison, Wis.) were generated nonvirally from the unmodified NIKS cell stocks. Both cell types were cultivated in standard keratinocyte. culture medium composed of a mixture of Ham's F-12 medium:Dulbecco's modified Eagle's medium, (3:1, final calcium concentration 0.66 mM) supplemented with 2.5% Fetal Clone II (Hyclone, Logan, Utah), 0.4 µg/ml hydrocortisone, 8.4 ng/ml cholera toxin, 5 µg/ml insulin, 24 µg/ml adenine, and 5-10 ng/ml epidermal growth factor. The keratinocytes were sub-cultured at weekly intervals onto mitomycin C-treated Swiss 3T3 fibroblasts (mito-C 3T3) as previously described Id. Keratinocyte monolayer cultures used in experimental conditions harvested for experiments at subconfluence. For encapsulation experiments, cells were fed differentiation media after exposing to air-liquid interface culture, StrataLife 3 (Stratatech Corp., Madison, Wis.). All cell cultures were maintained at 37° C. and 5% $CO_2$.

(B) Hydrogel Fabrication, 3D Cell Encapsulation and 2D Cell Adhesion

Covalently-crosslinked gelatin hydrogels were prepared by photo-crosslinking thiolated gelatin (Gel-PEG-Cys) with PEGdA (Mw 3400 Da). Gel-PEG-Cys was synthesized from type B gelatin (75 bloom, Sigma-Aldrich, USA) in accordance with Example 9, above. PEGdA was prepared following the method of Example 2, above. In brief, 20% w/w Gel-PEG-Cys stock solution was prepared in 0.5% (w/v) Irgacure 2959 (I-2959) solution at 37° C. PEGdA was accurately weighed, dissolved in 0.5% (w/v) I-2959 solution, and sterile filtered through 0.22 μm membrane filter. Gel-PEG-Cys solution was mixed with PEGdA solution via vortexing to give formulations such as $G_{cys}15P_{3400}5$, and $G_{cys}10P_{3400}10$. Cell suspensions at $2 \times 10^7$/mL were prepared in corresponding culture medium. Equal to 1/10 of gel precursor volume, cell suspension was added and mixed gently with gel precursor solution. 80 μL of hydrogel precursor solution was transferred to glass bottom petri dish molds (8 mm in diameter, 0.8 mm in thickness, In Vitro Scientific, USA) and subjected to photo-crosslinking with LED long-wavelength UV ($\lambda_{max}$=365 nm, intensity at 100 in W/cm²) for 90 s (Clearstone technology Inc., USA).

For 2D cell adhesion, $G_{cys}10P_{3400}10$ hydrogels were prepared as described above and allowed to reach equilibrium swelling in keratinocyte growth media for 24 h. $2 \times 10^5$ cell/mL NIKS or NIKS$^{VEGF}$ suspension was added to each well containing pre-Swollen hydrogel disks. Adherent cell viability and morphology were characterized using Live & Dead assay (Invitrogen, US) on day 1, 3, and 7. 3D NIKS and NIKS$^{VEGF}$ viabilities encapsulated in covalently crosslinked gelatin hydrogels were also determined via Live/dead stain.

(C) 3D NHDF and 3D NIKS Coculture

Neonatal human dermal fibroblast (NHDF, Lonza, USA) were encapsulated as described above in covalently crosslinked gelatin hydrogels ($G_{cys}15P_{3400}5$) at a density of $2 \times 10^6$/mL 7 days prior to NIKS and NIKS$^{VEGF}$ encapsulation. As control, NHDF were encapsulated in type I rat tail collagen gels (4 mg/mL, BD Bioscience, Franklin Lakes, N.J.) at a density of $1 \times 10^5$/mL 5 days prior to NIKS/NIKS$^{VEGF}$ encapsulation. NHDF entrapped hydrogels were placed in 12 mm Transwell® inserts (Costar® 3460, Corning, US) and cultured in FBM-2 with 10% FBS. NIKS and NIKS NIKS$^{VEGF}$ were encapsulated similarly in either covalently crosslinked gelatin hydrogels ($G_{cys}15P_{3400}5$) or collagen gels, and the NIKS or NIKS NIKS$^{VEGF}$ entrapped gels were layered on top of NHDF entrapped gels to conduct the coculture study. Keratinocyte growth media was used from day 1 to day 3 since coculture started. 3D coculture constructs were exposed to the air-liquid interface on Day 4 when switching media to StrataLife 3. During coculture period, cell supernatants were assayed for VEGF expression on day 1, 3, 7, and 14 using an enzyme-linked immunosorbent assay (ELISA, Human VEGF ELISA Kit, Pierce Biotechnology, Rockford, Ill.).

(D) NHDF and 2D NIKS Coculture

NHDF entrapped hydrogels ($G_{cys}10P_{3400}$ 10) were prepared as aforementioned, and cultured in FBM-2 for 6 days. NHDF entrapped gels were subjected to culturing in keratinocyte growth media for 24 h prior to keratinocyte seeding. NIKS and NIKS$^{VEGF}$ cell suspensions in keratinocyte growth media were seeded on top of NHDF entrapped hydrogels ($5 \times 10^5$ cell per well) using 12 well Transwell® inserts. Keratinocyte growth media was used prior to air-liquid interface culture. When adherent NIKS cells reached near confluence, the coculture constructs were subjected to air-liquid interface culture using StrataLife 3 as culture medium. Similarly, cell supernatants were assayed for VEGF on day 1, 3, 7, and 14 via ELISA assay. For comparison, cell supernatants from monoculture of NIKS, NIKS$^{VEGF}$, and NHDF entrapped gels were assayed similarly.

(E) Immunofluorescence and Tissue Sectioning

Cell entrapped hydrogels were washed with DPBS and fixed in 4% paraformaldehyde for 4 h at room temperature followed with incubation in 0.25% Triton X-100 plus 1% BSA in PBS solution for 2 h as described in Example 12, above. Cytoskeletal F-actin was stained with 1 U/mL Alexfluo 488 conjugated phalloidin (Invitrogen, N.J., U.S.A) at 4° C. overnight. Fluorescence images of the F-actin distribution were acquired by confocal microscope (F1000, Olympus, Japan). Cell entrapped hydrogel samples were fixed in 10% neutral buffered formalin for 3 d, and in a 1:1 v/v mixture of 20% w/w sucrose and Tissue-Tek® (Sakura Finetek, Japan) at 4° C. for 48 h. Cell entrapped hydrogel samples were then embedded in Tissue-Tee and snap-frozen in liquid nitrogen. The frozen samples were sectioned using a cryostat (LEICA, Germany) to a thickness of 10 μm, and stained with hematoxylin and eosin. Stained sections were viewed and photographed using a Nikon eclipse E400 microscope equipped with a Nikon digital camera.

(F) Statistics

Quantitative ELISA data are represented as a mean plus or minus (±) a standard deviation (S.D.) of samples in at least three independent experiments. VEGF expression levels from NIKS and NIKS$^{VEGF}$ were analyzed via impaired student's t-test. A value of $p<0.05$ was considered statistically significant.

(G) 2D Cell Adhesion

Figure 24:
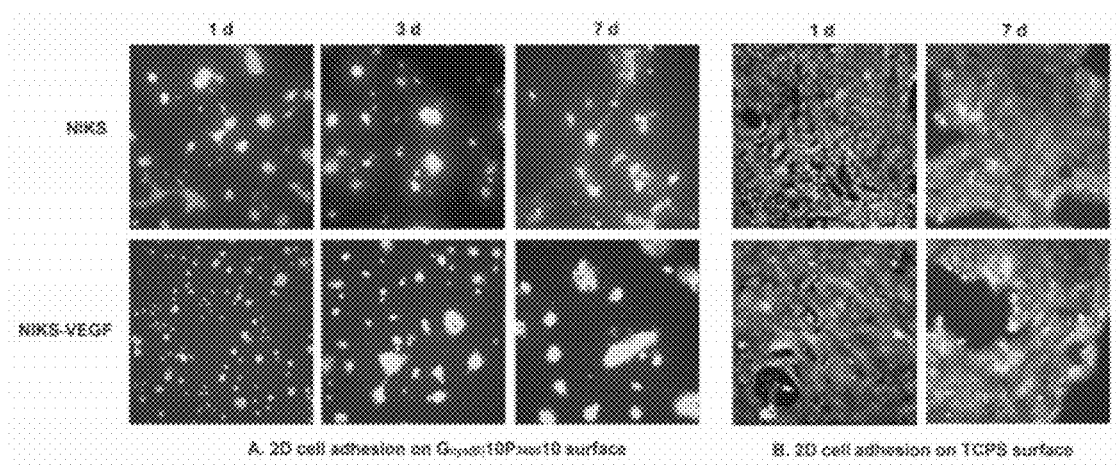
FIGS. 24A and B are images of 2D cell adhesion of NIKS and NIKS$^{VEGF}$ on covalently crosslinked thiolated gelatin hydrogel $G_{cys}10P_{3400}10$ (FIG. 24A), and TCPS surface (FIG. 24B). Cells were stained with calcein-AM for live cell (green) and EthD for dead cell (red). (Magnification, 10$^x$)

Based on the above Examples, $G_{cys}10P_{3400}10$ was selected to conduct a 2D cell adhesion study of NIKS and NIKS$^{VEGF}$ cells due to relatively higher gel surface stiffness than $G_{cys}15P_{3400}5$. Both NIKS and NIKS$^{VEGF}$ adhered to the $G_{cys}10P_{3400}10$ hydrogel surface 24 h after initial seeding (FIGS. 24A and 24B). Unlike cell morphology on the tissue culture polystyrene surface (TCPS), local cluster formations and only some cell spreading were observed on the $G_{cys}10P_{3400}10$ hydrogel surface. This could be due to much stronger cell-cell adhesion in comparison to cell-matrix interaction that led to cell cluster formation. With respect to cell adhesion onto TCPS, NIKS cells formed a sheet-like monolayer which indicated both cell-cell and cell-matrix interactions were strong to maintain such morphological characteristics. Moreover, the number of dead cells on hydrogel surfaces increased over time (FIGS. 24A and 24B). The NIKS and NIKS$^{VEGF}$ culture condition requires the presence of mito-$C_3T3$, which provides necessary functional extracellular matrix and matrix-associated factors such as cytokines into the conditioned medium. Thus, adherent NIKS and NIKS$^{VEGF}$ cells might not proliferate or differentiate on the hydrogel surface due to insufficient culture conditions, but proceed to cell death instead.

(H) NIKS and NIKS$^{VEGF}$ Viability and Morphology

Figure 25:
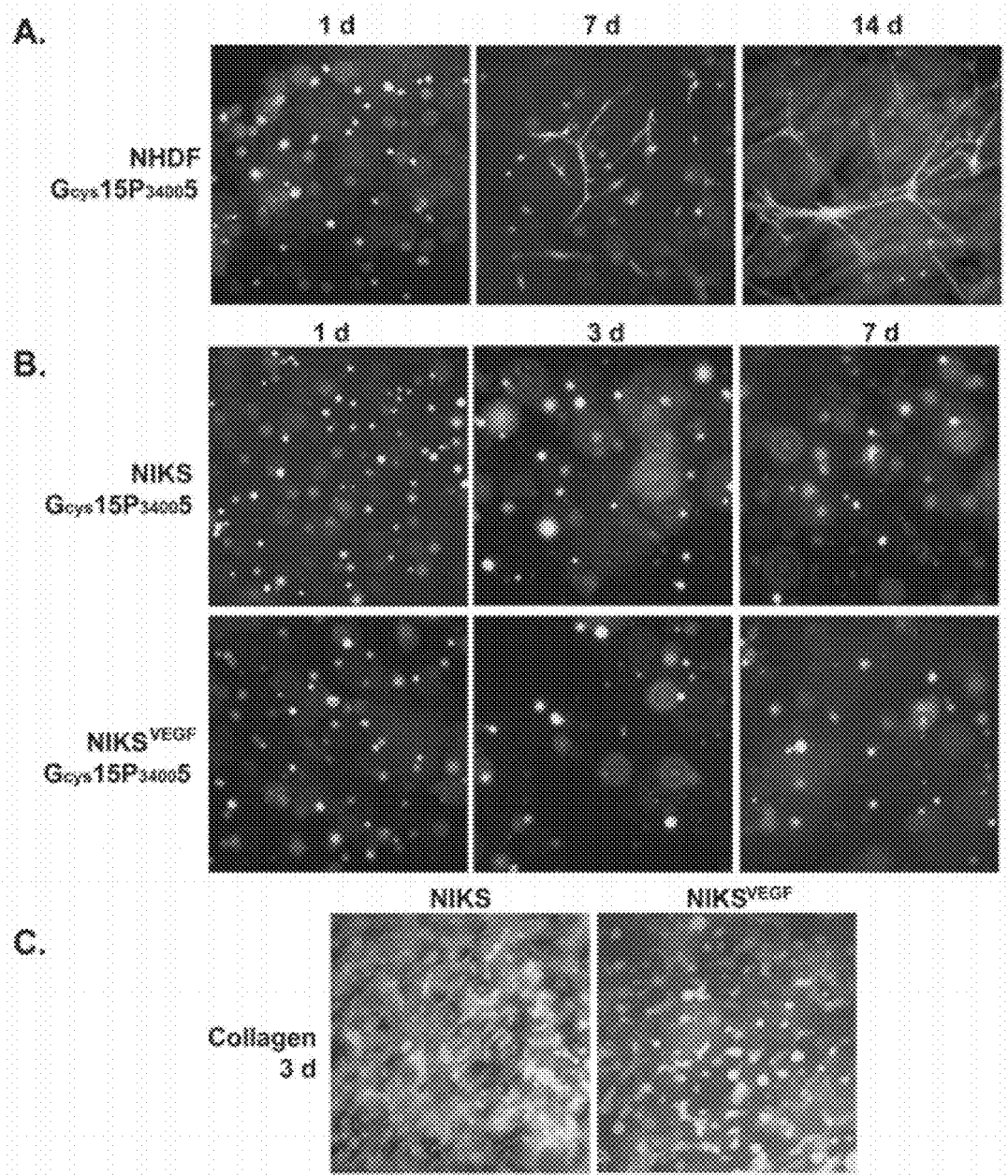
FIGS. 25A, 25B and 25C are images of NHDF encapsulated in $G_{cys}15P_{3400}5$ hydrogels with well-spread morphology and the formation of cellular networks on day 14 (FIG. 25A), NIKS and NIKS$^{VEGF}$ encapsulated in $G_{cys}15P_{3400}5$ hydrogels displaying spheroid morphology (FIG. 25B), and NIKS and NIKS$^{VEGF}$ encapsulated in 4 mg/mL collagen gels on Day 3 displaying formation of intercellular networks (FIG. 25C). Cells were stained with calcein-AM for live cell (green) and EthD for dead cell (red). (Magnification, 10$^x$)

To address the feasibility of 3D encapsulation of NIKS and NIKS$^{VEGF}$, both cell types were encapsulated in $G_{cys}15P_{3400}5$ hydrogels and 4 mg/mL collagen gels and subjected to coculture with encapsulated NHDF cells for over 14 d. $G_{cys}15P_{3400}5$ hydrogel was selected because fibroblasts displayed well spread morphology using this formulation (FIG. 25A). It is speculated that decreasing PEGdA content would result in lower hydrogel stiffness and higher water content thus mechanical properties comparable to collagen. Both NIKS and NIKS$^{VEGF}$ displayed high fraction of viable cells (>80%) 24 h after 3D encapsulation in $G_{cys}15P_{3400}5$ hydrogel (FIG. 25B), indicating the photopolymerization-based encapsulation process was of minimum toxicity to NIKS and NIKS$^{VEGF}$. Unlike well-spread fibroblasts encapsulated in these covalently crosslinked hydrogels, NIKS and NIKS$^{VEGF}$ remained in the spheroid shape and did not show cytoplasmic spreading over 7-d period. In contrast, NIKS and NIKS$^{VEGF}$ encapsulated in collagen gels displayed small round or polygonal morphology and the rapid formation of intercellular networks in 3D environment (FIG. 25C), thus demonstrating NIKS and NIKS$^{VEGF}$ cells could survive in a 3D-environment under suitable conditions. However, collagen based coculture samples showed dramatic matrix contraction after 5-7 d consistent with prior reports, most likely due to NHDF induced gel shrinkage. In comparison, the crosslinked gelatin hydrogel cocultured constructs showed well-maintained physical structure throughout the culture period.

(I) 3D NHDF and 3D NIKS/NIKS$^{VEGF}$ Coculture

Figure 26:
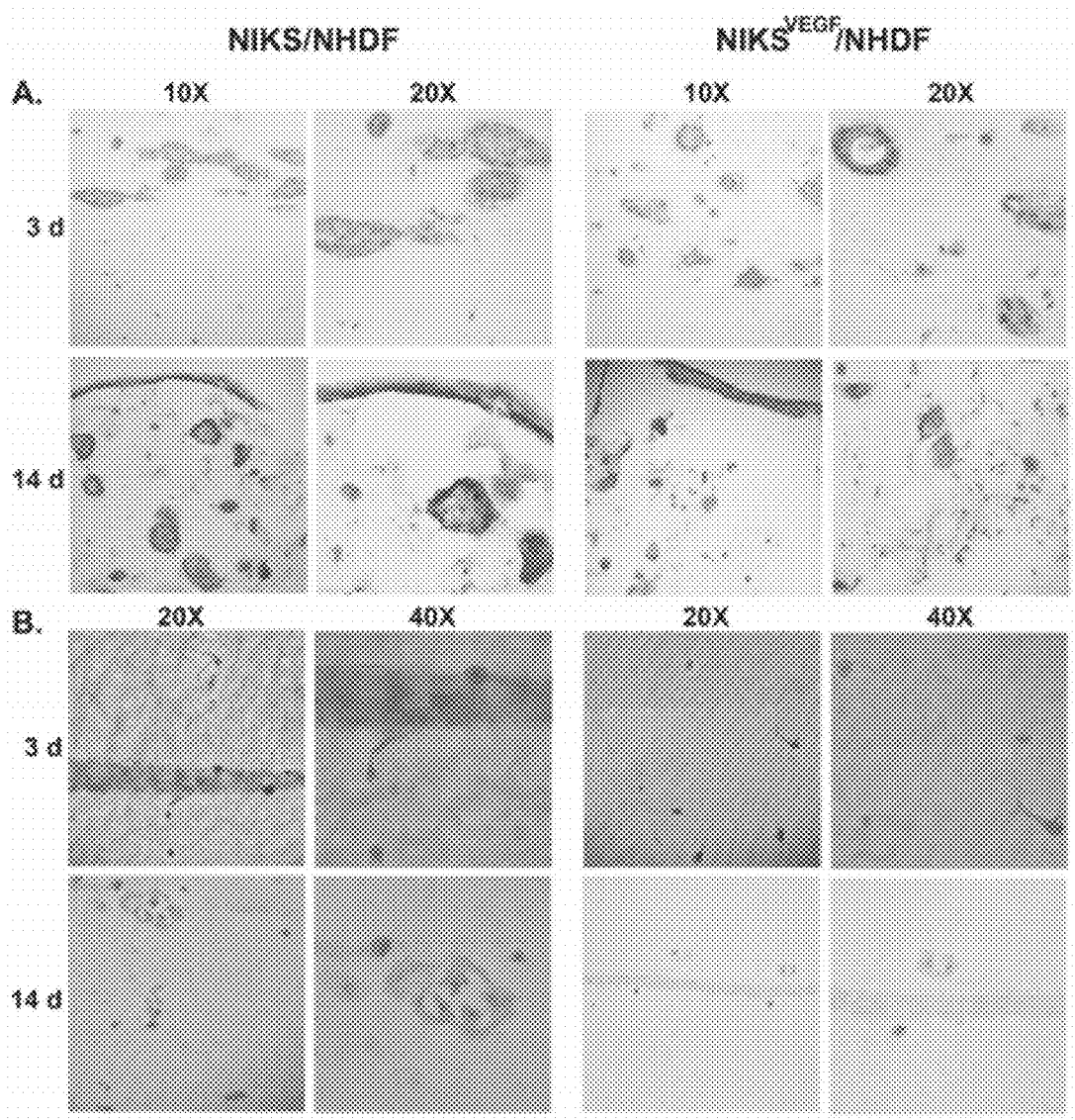
FIGS. 26A and 26B Representative histologic sections of 3D NIKS/NIKS$^{VEGF}$ in coculture with 3D NHDF in collagen gels (FIG. 26A), and 3D NIKS/NIKS$^{VEGF}$ in coculture with 3D NHDF in $G_{cys}15P_{3400}5$ hydrogel (FIG. 26B). Samples were fixed, sectioned and stained with hematoxylin and eosin. Sections were viewed and photographed.

The hydrogel matrix can be explored as a cell delivery vehicle for short term applications. Thus, a 3D coculture model was developed to efficiently present therapeutic cells such as fibroblasts and keratinocytes to the wound site in facilitating the healing process. The present biomaterials may also be used as a platform to deliver biological cues that does not require long-term in vitro culture before application. In this study, 3D coculture samples using collagen gels showed a perfect contact between the two gel layers, i.e. there was no observable boundary line in between the two layers (FIG. 26A). NHDF encapsulated in the collagen matrix displayed well-spread morphology, and tended to migrate into the keratinocyte layer. In comparison, NIKS and NIKS$^{VEGF}$ remained in the cluster forms within the bulk of the gel (FIG. 26B). However, NIKS and NIKS$^{VEGF}$ keratinocytes close to the gel surface appeared to migrate upward and formed a continuous cell layer on top of the collagen gel surface. When subjected to air-liquid interface culture, keratinocytes proliferated and differentiated into an acellular keratinized layer on Day 14 (FIG. 26A). With respect to the thiolated gelatin-PEGdA hydrogel matrix, a clear boundary line was observed between the two gel layers, but the two gel layers were in close contact. Similar to collagen gels, NIKS and NIKS$^{VEGF}$ keratinocytes remained in the cluster form as shown in FIG. 26B.

(J) NHDF vs. 2D NIKS/NIKS$^{VEGF}$ Coculture

Figure 27:
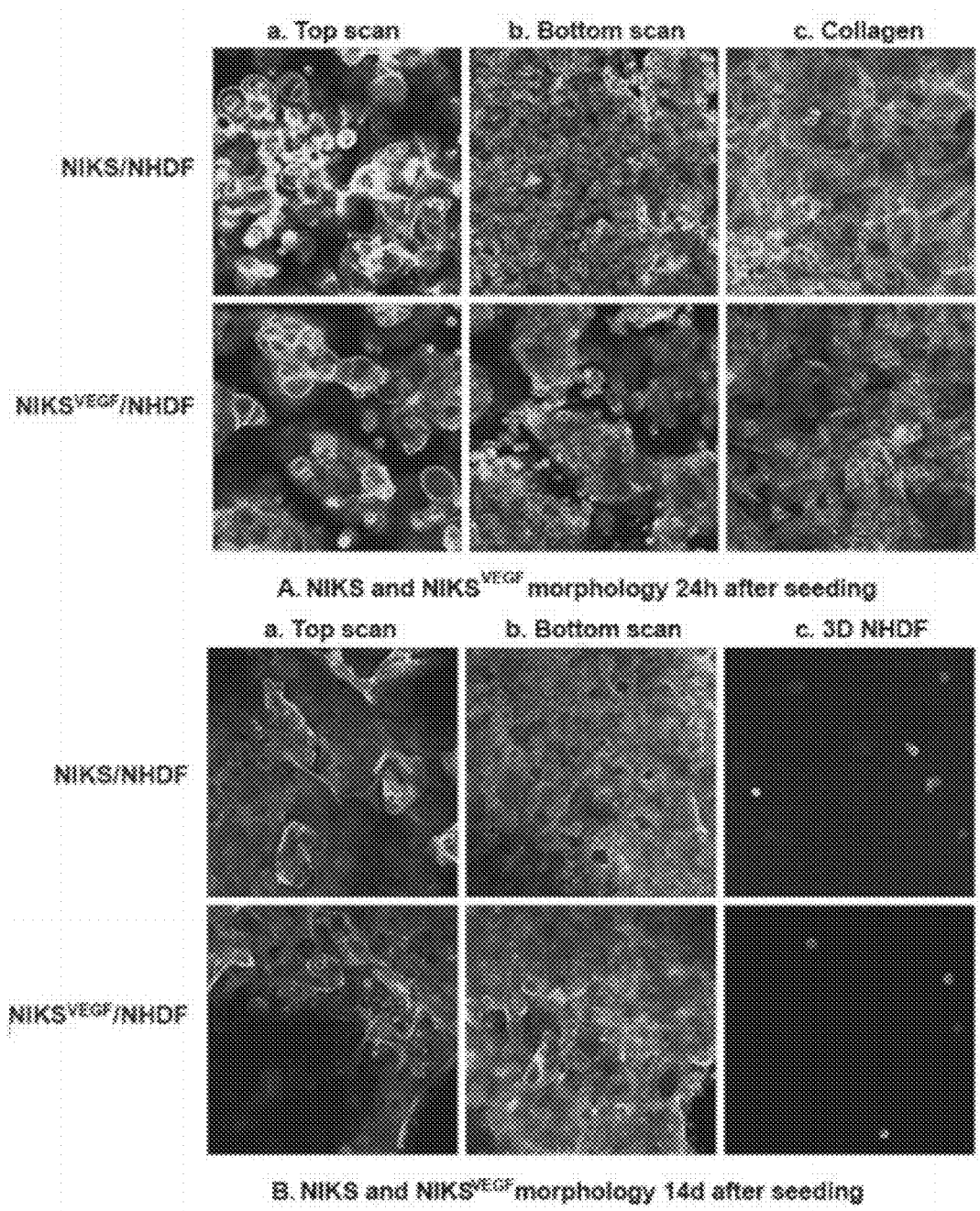
FIGS. 27A and 27B are images of (FIG. 27A) 2D NIKS and NIKS$^{VEGF}$ morphology on 3D cocultured NHDF encapsulated matrices 24 h after seeding: (a) $G_{cys}10P_{3400}10$, top scan; $G_{cys}10P_{3400}10$, bottom scan; (c) Collagen.

Based on observations with 3D coculture of NIKS and NHDF cells, keratinocytes did not show evidence of proliferation and differentiation within the 3D thiolated gelatin-PEGdA hydrogel matrix. Therefore, a different design was used to study keratinocyte differentiation during 3D NHDF and 2D NIKS/NIKS$^{VEGF}$ coculture. Instead of encapsulating keratinocytes in the hydrogel matrix, NIKS and NIKS$^{VEGF}$ keratinocytes were seeded on hydrogel surfaces with pre-encapsulated fibroblasts. $G_{cys}10P_{3400}10$ formulation was selected due to high 3D fibroblast viability and necessary stiffness for 2D cell adhesion. As shown in FIG. 27, both NIKS and NIKS$^{VEGF}$ reached subconfluence 24 h after initial seeding with similar basal morphologies as compared to collagen gels. Some keratinocytes from the top layer displayed keratinized structure, a sign of early maturation (FIGS. 27A AND 27B top scan). NIKS and NIKS$^{VEGF}$ keratinocytes remained adherent and showed normal morphology for up to 14 d (FIG. 27B bottom scan). Using collagen as the matrix, NIKS and NIKS$^{VEGF}$ keratinocytes in organotypic culture exhibited stratification and differentiation 14 d since coculture started. A single layer of cuboidal basal cells was observed at the epidermis and the dermal junction (FIG. 28A) consistent with previous reports. The basal cells divided into daughter cells that migrate upwards with flattened and squamous morphology, and cells gradually became enucleated and formed cornified, keratinized structures. In contrast, NIKS and NIKS$^{VEGF}$ showed a thin layer of cell and cell cluster formation on $G_{cys}10P_{3400}10$ hydrogel surface (FIG. 28B) on day 14 after coculture, but different degrees of stratification and differentiation of NIKS and NIKS$^{VEGF}$ on synthetic hydrogel surface were observed on day 21 (FIG. 28C). Similar to differentiated cell morphology on collagen gels on day 14, near cuboidal NIKS keratinocytes on the synthetic hydrogel surface were observed near the basal layer. Above the basal layer, differentiated cells with flattened morphology, and flattened cells with no clear nucleus structures were observed (FIG. 28C). Therefore, the current thiolated gelatin and PEGdA-based synthetic biomatrix was proven to be able to support 2D NIKS and NIKS$^{VEGF}$ kerationcytes growth and differentiation under coculture with encapsulated NHDF cells.

(K) VEGF Expression

Angiogenesis plays a crucial role during wound healing process, because the formation of new blood vessels allows nutrients, oxygen, mediators and regulators to reach the healing center. Viable skin equivalents comprised of keratinocytes, and fibroblasts in ECM-derived matrix have been successfully developed. However, skin equivalents lack a vascular plexus, and were found to have slower vascularization as compared to autografts. Vascularization of skin equivalents occurs through the process of neovascularization alone, which contributes to the failure of cultured skin grafts by increasing time for reperfusion, ischemia, and nutrient deprivation of grafted cells. Thus, keratinocytes were modified via genetic engineering approaches to express high levels of growth factors that can facilitate vascularization during the healing process. Vascular endothelial growth factor (VEGF) is a specific mitogen for microvascular endothelial cells that can stimulate vascularization and angiogenesis. Studies showed VEGF secreted by epidermal keratinocytes had a mitogenic effect on dermal microvascular endothelial cells, modulation of VEGF levels in the epidermis could potentially lead to enhanced skin vascularization. Normal VEGF levels are critical for regulating blood vessel development. Normal ranges of VEGF were 62-707 pg/in L for serum and 0-115 pg/mL for plasma, while patients with myeloid metaplasia had significantly higher circulating VEGF concentrations ranging from 74-4000 ng/mL. The up-regulation of VEGF expression was observed during wound healing, and pathological tissue states such as tumors and carcinomas. Therefore, the controlled local over expression of VEGF from genetically engineered keratinocytes may effectively improve vascularization of viable cultured skin equivalents. However, the expression level of VEGF needs to be carefully controlled so as not to induce VEGF-related risks such as cancer and tumor.

Using the present biomaterials in a coculture model, VEGF expression levels were compared between unmodified NIKS and genetically modified NIKS$^{VEGF}$. Within each formulation group, VEGF expression from NIKS$^{VEGF}$ showed significantly higher VEGF expression levels than regular NIKS at all time points (FIGS. 29A AND 29B) (p<0.05). Irrespective of culturing conditions, VEGF expression from NIKS-$^{VEGF}$ ranges from 500-3500 pg/mL from Day 3 to Day 14. For both NIKS and NIKS$^{VEGF}$ keratinocytes, VEGF expression increased over time from day 1 to day 7, and usually reached peak on day 7 or 14. The continuous VEGF expression from 3D encapsulated NIKS and NIKS$^{VEGF}$ indicated the encapsulated cells remained active for up to 14 d in the synthetic hydrogel matrix, and cells were able to secret a significant amount of VEGF upon stimulation. Thus, VEGF results provided strong evidence for using thiolated gelatin-PEGdA hydrogel in keratinocyte 3D encapsulation. Moreover, VEGF expression from 3D encapsulated NIKS and NIKS$^{VEGF}$ in synthetic matrix showed comparable levels as from collagen matrix in early time points, i.e. Day 1 and 3, but synthetic matrix showed lower VEGF expression levels on Day 7 and 14. This is probably due to the lower number of viable cells entrapped within the matrices. However, no significant differences in VEGF expression from NIKS$^{VEGF}$ were observed between synthetic and collagen matrices in 3D NHDF and 2D NIKS$^{VEGF}$ coculture (FIG. 28B) on day 7 and 14, indicating the potential of using synthetic matrix to develop novel dermal equivalences.

In monoculture, both NIKS and NIKS$^{VEGF}$ showed an increasing VEGF expression over time through 14-d period. NIKS$^{VEGF}$ exhibited much higher VEGF expression at all time points than regular NIKS. 3-14 d VEGF expression levels from Gcys-NIKS$^{VEGF}$ displayed comparable values compared to those from Col-NIKS$^{VEGF}$/NHDF coculture. In coculture, NIKS and NIKS$^{VEGF}$ encapsulated in G$_{cys}$15P$_{3400}$5 hydrogels showed similar VEGF expression trend from 1-7 d except that VEGF expression from Gcys-NIKS$^{VEGF}$/NHDF decreased on 14 d. Monoculture results seemed to display higher VEGF expression at later tune points than coculture, which remains to be addressed in future works. Moreover, protein expression is directly related to the number of active cells that have been encapsulated. Therefore, a high cell encapsulation density is likely to produce high protein expression level.

EQUIVALENTS

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A biomaterial comprising:
   at least one biopolymer comprising
      naturally occurring amino groups and
      at least two bifunctional modifiers wherein each bifunctional modifier has the formula:

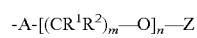
   -A-[(CR$^1$R$^2$)$_m$—O]$_n$—Z

A is a divalent moiety covalently bonded to the naturally occurring amino group of the biopolymer and
      Z is a monovalent moiety comprising a thiol group;
   at least one poly(alkylene oxide) cross-linked to at least two of the thiol groups of the biopolymer;
   wherein;
      the divalent moiety is selected from the group consisting of —O—, —S—, C$_{1-24}$-alkyl, C$_{2-24}$-alkenyl, C$_{2-24}$-alkynyl, C$_{1-24}$-alkoxy, C$_{1-24}$-heteroalkyl, C$_{2-24}$-heteroalkenyl, C$_{2-24}$-heteroalkynyl, cyano-C$_{1-24}$-alkyl, C$_{3-10}$-cycloalkyl, C$_{3-10}$-cycloalkenyl, C$_{3-10}$-cycloheteroalkyl, C$_{3-10}$-cycloheteroalkenyl, acyl, acyl-C$_{1-24}$-alkyl, acyl-C$_{2-24}$-alkenyl, acyl-C$_{2-24}$-alkynyl, carboxy, C$_{1-24}$-alkylcarboxy, C$_{2-24}$-alkenylcarboxy, C$_{2-24}$-alkynylcarboxy, carboxy-C$_{1-24}$-alkyl, carboxy-C$_{2-24}$-alkenyl, carboxy-C$_{2-24}$-alkynyl, aryl, aryl- C$_{1-24}$-alkyl, aryl-C$_{2-24}$-alkenyl, aryl-C$_{2-24}$-alkynyl, heteroaryl, heteroaryl-C$_{1-24}$-alkyl, heteroaryl-C$_{2-24}$-alkenyl, heteroaryl-C$_{2-24}$-alkynyl, sulfonate, arylsulfonate, and heteroarylsulfonate;

at each occurrence R$^1$ and R$^2$ is independently selected from the group consisting of H, methyl, and ethyl;

m is an integer from 2 to 8; and n is an integer ranging from 1 to 20,000.

2. The biomaterial of claim 1 wherein the biopolymer comprises gelatin, collagen, whey protein, chitosan, or combinations of any two or more thereof.

3. The biomaterial of claim 1 wherein the biopolymer comprises gelatin and/or collagen.

4. The biomaterial of claim 1 wherein the biopolymer comprises Type A gelatin, Type B gelatin or both.

5. The biomaterial of claim 1 wherein the monovalent moiety is selected from the group consisting of thiol, cysteine, carbonyl cysteine, homocysteine, cysteamine, cystamine, C$_{1-24}$-alkylthiol, C$_{2-24}$-alkenylthiol, C$_{2-24}$-alkynylthiol, —O—C$_{1-24}$-alkylthiol, C$_{1-24}$-heteroalkylthiol, C$_{2-24}$-heteroalkenylthiol, C$_{2-24}$-heteroalkynylthiol, C$_{3-10}$-cycloalkylthiol, C$_{3-10}$-cycloalkenylthiol, C$_{3-10}$-cycloheteroalkylthiol, C$_{3-10}$-cycloheteroalkenylthiol, —C(O)—C$_{1-24}$-alkylthiol, —C(O)—C$_{2-24}$-alkenylthiol, —C(O)—C$_{2-24}$-alkynylthiol, —OC(O)—C$_{1-24}$-alkylthiol, —OC(O)—C$_{2-24}$-alkenylthiol, —OC(O)—C$_{2-24}$-alkynylthiol, arylthiol, C$_{1-24}$-alkyl-arylthiol, C$_{2-24}$-alkenyl-arylthiol, C$_{2-24}$-alkynyl-arylthiol, heteroarylthiol, C$_{1-24}$-alkyl-heteroarylthiol, C$_{2-24}$-alkenyl-heteroarylthiol, and C$_{2-24}$-alkynyl-heteroarylthiol.

6. The biomaterial of claim 1 wherein n is an integer from 1 to 2,000.

7. The biomaterial of claim 1 wherein n is an integer from 1 to 200.

8. The biomaterial of claim 1 wherein n is an integer from 1 to 100.

9. The biomaterial of claim 1 wherein the poly(alkylene oxide) is selected from the group consisting of poly(ethylene glycol), polypropylene glycol), and mixtures thereof.

10. The biomaterial of claim 9 wherein the biopolymer comprises gelatin, poly(ethylene glycol) and cysteine.

11. The biomaterial of claim 1, further comprising a pharmacologically active agent entrained within the biomaterial or covalently attached to the biopolymer.

12. The biomaterial of claim 11 wherein the pharmacologically active agent is selected from the group consisting of vulnerary agents, hemostatic agents, antibiotics, antithelmintics, anti-fungal agents, hormones, anti-inflammatory agents, proteins, polypeptides, oligonucleotides, cytokines, and enzymes.

13. A method comprising administering a biomaterial of claim 11 to a patient in need of said pharmacologically active agent.

14. The biomaterial of claim 1, further comprising living cells entrained within the biomaterial.

15. A method comprising administering a biomaterial of claim 14 to a patient in need of said living cells.

16. The method of claim 15 wherein the biomaterial comprises at least two layers, each layer comprising a different cell type.

17. A method comprising reacting a poly(alkylene oxide)-diacrylate with at least one biopolymer comprising naturally occurring amino groups and at least two bifunctional modifiers wherein each bifunctional modifier is of the formula -A-[(CR$^1$R$^2$)$_m$—O]$_n$—Z A is a divalent moiety covalently bonded to the naturally occurring amino groups of the biopolymer and Z is a monovalent moiety comprising a thiol group, to provide a biomaterial in which the at least one poly(alkylene oxide) is cross-linked to at least two of the thiol groups of the biopolymer;

wherein the divalent moiety is selected from the group consisting of —O—, —S—, C$_{1-24}$-alkyl, C$_{2-24}$-alkenyl, C$_{2-24}$-alkynyl, C$_{1-24}$-alkoxy, C$_{1-24}$-heteroalkyl, C$_{2-24}$-heteroalkenyl, C$_{2-24}$-heteroalkynyl, cyano-C$_{1-24}$-alkyl, C$_{3-10}$-cycloalkyl, C$_{3-10}$-cycloalkenyl, C$_{3-10}$-cycloheteroalkyl, C$_{3-10}$-cycloheteroalkenyl, acyl, acyl-C$_{1-24}$-alkyl, acyl-C$_{2-24}$-alkenyl, acyl-C$_{2-24}$-alkynyl, carboxy, C$_{1-24}$-alkylcarboxy, C$_{2-24}$-alkenylcarboxy, C$_{2-24}$-alkynylcarboxy, carboxy-C$_{1-24}$-alkyl, carboxy-C$_{2-24}$-alkenyl, carboxy-C$_{2-24}$-alkynyl, aryl, aryl-C$_{1-24}$-alkyl, aryl-C$_{2-24}$-alkenyl, aryl-C$_{2-24}$-alkynyl, heteroaryl, heteroaryl-C$_{1-24}$-alkyl, heteroaryl-C$_{2-24}$-alkenyl, heteroaryl-C$_{2-24}$-alkynyl, sulfonate, arylsulfonate, and heteroarylsulfonate;

at each occurrence R$^1$ and R$^2$ is independently selected from the group consisting of H, methyl, and ethyl;

m is an integer from 2 to 8;

n is an integer ranging from 1 to 20,000.

18. The method of claim 17, further comprising crosslinking the biopolymer and the poly(alkylene oxide) by photopolymerization or Michael addition.

19. The biomaterial of claim 1, wherein the monovalent moiety is

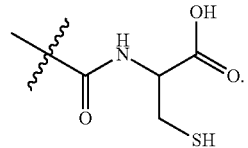 [SMILES: *C(=O)NC(CS)C(=O)O]

20. The biomaterial of claim 2, wherein the biomaterial further comprises calcium alginate, calcium/sodium alginate, oxidized regenerated cellulose, carboxymethylcellulose, amino-modified cellulose, or combinations of any two or more thereof.

* * * * *

UNITED STATES PATENT AND TRADEMARK OFFICE
CERTIFICATE OF CORRECTION

| | |
|---|---|
| PATENT NO. | : 8,980,295 B2 |
| APPLICATION NO. | : 13/411387 |
| DATED | : March 17, 2015 |
| INVENTOR(S) | : Weiyuan J. Kao and Yao Fu |

It is certified that error appears in the above-identified patent and that said Letters Patent is hereby corrected as shown below:

In the Claims

In Column 43, Claim 9, Line 38, remove "polypropylene glycol)" and replace with -- poly(propylene glycol) --.

Signed and Sealed this
Eighth Day of September, 2015

Michelle K. Lee
*Director of the United States Patent and Trademark Office*